(12) United States Patent
Shitagaki et al.

(10) Patent No.: US 8,231,942 B2
(45) Date of Patent: Jul. 31, 2012

(54) COMPOSITION, METHOD FOR MANUFACTURING THIN FILM, AND METHOD FOR MANUFACTURING LIGHT-EMITTING ELEMENT

(75) Inventors: Satoko Shitagaki, Kanagawa (JP); Satoshi Seo, Kanagawa (JP); Tsunenori Suzuki, Kanagawa (JP); Sachiko Kawakami, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 425 days.

(21) Appl. No.: 12/466,910

(22) Filed: May 15, 2009

(65) Prior Publication Data

US 2009/0317539 A1 Dec. 24, 2009

(30) Foreign Application Priority Data

May 16, 2008 (JP) ................... 2008-130159

(51) Int. Cl.
 *H01L 51/54* (2006.01)
 *C07D 209/56* (2006.01)
(52) U.S. Cl. ............ 427/384; 564/304; 252/301.31; 548/440; 548/445; 313/504
(58) Field of Classification Search .......... 427/384; 564/304; 252/301.31; 548/440, 445; 313/504
See application file for complete search history.

(56) References Cited

U.S. PATENT DOCUMENTS

| | | | |
|---|---|---|---|
| 5,635,308 A | 6/1997 | Inoue et al. | |
| 5,811,834 A | 9/1998 | Tamano et al. | |
| 6,143,201 A | 11/2000 | Mano | |
| 6,815,094 B2 | 11/2004 | Lee et al. | |
| 7,674,914 B2 | 3/2010 | Egawa et al. | |
| 7,723,722 B2 | 5/2010 | Kawakami et al. | |
| 7,732,064 B2 | 6/2010 | Kawakami et al. | |
| 7,842,945 B2 | 11/2010 | Egawa et al. | |
| 7,879,464 B2 | 2/2011 | Kawakami et al. | |
| 7,880,019 B2 | 2/2011 | Egawa et al. | |
| 8,039,122 B2 | 10/2011 | Kawakami et al. | |
| 2004/0146746 A1 | 7/2004 | Lee et al. | |
| 2004/0161632 A1 | 8/2004 | Seo et al. | |

(Continued)

FOREIGN PATENT DOCUMENTS

EP 0 681 019 A2 11/1995

(Continued)

OTHER PUBLICATIONS

PCT International Search Report for application PCT/JP2009/058113, Jun. 2, 2009.

(Continued)

*Primary Examiner* — Gregory Delcotto
(74) *Attorney, Agent, or Firm* — Husch Blackwell LLP

(57) ABSTRACT

It is an object to provide a composition in which an anthracene derivative is dissolved and a technique in which a thin film that has a favorable film quality is formed by a wet process using the composition. In addition, it is another object to manufacture a highly reliable light-emitting element using the composition at low cost with high productivity. A composition having a solvent and an anthracene derivative having one anthracene structure and one carbazolyl group which is bonded to the anthracene structure directly or through a phenyl group is formed. A thin film with a favorable film quality can be formed by a wet process using the composition. Accordingly, a highly reliable light-emitting element can be manufactured using such a thin film.

15 Claims, 30 Drawing Sheets

U.S. PATENT DOCUMENTS

| | | |
|---|---|---|
| 2005/0095455 A1 | 5/2005 | Nomura et al. |
| 2005/0116633 A1 | 6/2005 | Yamazaki et al. |
| 2005/0214565 A1 | 9/2005 | Ikeda et al. |
| 2005/0244670 A1 | 11/2005 | Saitoh et al. |
| 2006/0068221 A1 | 3/2006 | Saitoh et al. |
| 2006/0292394 A1 | 12/2006 | Iwaki et al. |
| 2007/0049778 A1 | 3/2007 | Nomura et al. |
| 2007/0059556 A1 | 3/2007 | Kim et al. |
| 2007/0075632 A1 | 4/2007 | Kawakami et al. |
| 2007/0152572 A1 | 7/2007 | Kawakami et al. |
| 2007/0205412 A1 | 9/2007 | Bae et al. |
| 2008/0001123 A1 | 1/2008 | Inoue et al. |
| 2008/0017853 A1 | 1/2008 | Egawa et al. |
| 2008/0107918 A1 | 5/2008 | Egawa et al. |
| 2008/0114178 A1 | 5/2008 | Kawakami et al. |
| 2008/0268284 A1 | 10/2008 | Kawakami et al. |
| 2008/0286445 A1 | 11/2008 | Suzuki et al. |
| 2009/0004506 A1 | 1/2009 | Nomura et al. |
| 2009/0058278 A1 | 3/2009 | Ushikubo et al. |
| 2009/0085479 A1 | 4/2009 | Ushikubo |
| 2009/0102366 A1 | 4/2009 | Ushikubo et al. |
| 2009/0146139 A1 | 6/2009 | Stoessel et al. |
| 2009/0174321 A1 | 7/2009 | Osaka et al. |
| 2009/0247795 A1 | 10/2009 | Kawakami |
| 2009/0253916 A1 | 10/2009 | Kawakami et al. |
| 2009/0267497 A1 | 10/2009 | Kawakami et al. |
| 2009/0267498 A1* | 10/2009 | Kawakami et al. ........... 313/504 |

FOREIGN PATENT DOCUMENTS

| | | |
|---|---|---|
| EP | 0 786 926 A2 | 7/1997 |
| EP | 1 496 041 A1 | 1/2005 |
| EP | 1 695 952 A1 | 8/2006 |
| EP | 2 031 036 A | 3/2009 |
| EP | 2 051 310 A1 | 4/2009 |
| JP | 61-296085 | 12/1986 |
| JP | 1-204991 | 8/1989 |
| JP | 6-330035 | 11/1994 |
| JP | 8-12600 | 1/1996 |
| JP | 11-193378 | 7/1999 |
| JP | 2003-31371 | 1/2003 |
| JP | 2003-146951 | 5/2003 |
| JP | 2003-229273 | 8/2003 |
| JP | 2004-095850 | 3/2004 |
| JP | 2006-041103 | 2/2006 |
| JP | 2007-15933 | 1/2007 |
| JP | 2009-076450 | 4/2009 |
| JP | 2009-099966 | 5/2009 |
| WO | WO 2004/020388 A1 | 3/2004 |
| WO | WO 2004/020548 A1 | 3/2004 |
| WO | WO 2004/075603 A2 | 9/2004 |
| WO | WO 2004/075604 A2 | 9/2004 |
| WO | WO 2006/070712 A1 | 7/2006 |
| WO | WO 2007/102683 A1 | 9/2007 |
| WO | WO 2007/110129 A1 | 10/2007 |

OTHER PUBLICATIONS

PCT Written Opinion of the International Searching Authority for application PCT/JP2009/058113, Jun. 2, 2009.

European Search Report for application EP 09 00 4366, Mar. 16, 2010.

Kim et al. (2007): STN International HCAPLUS database, (Columbus, Ohio), Accession No. 2007:286997.

* cited by examiner

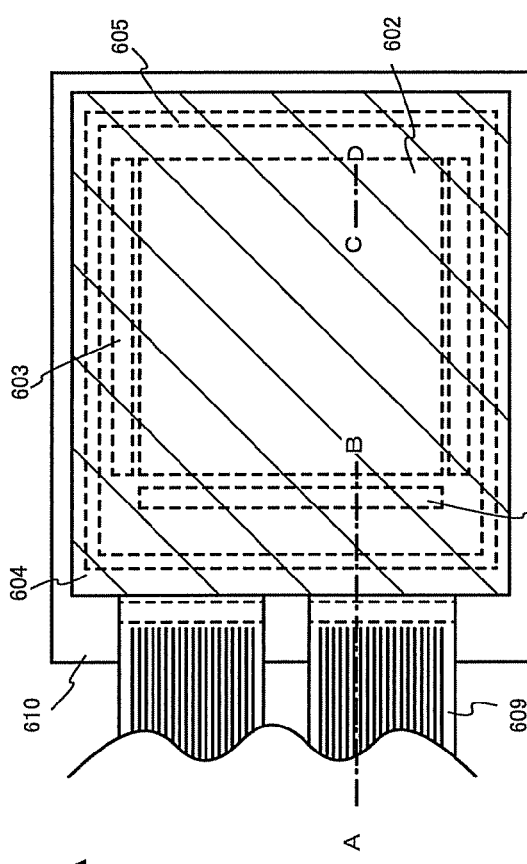
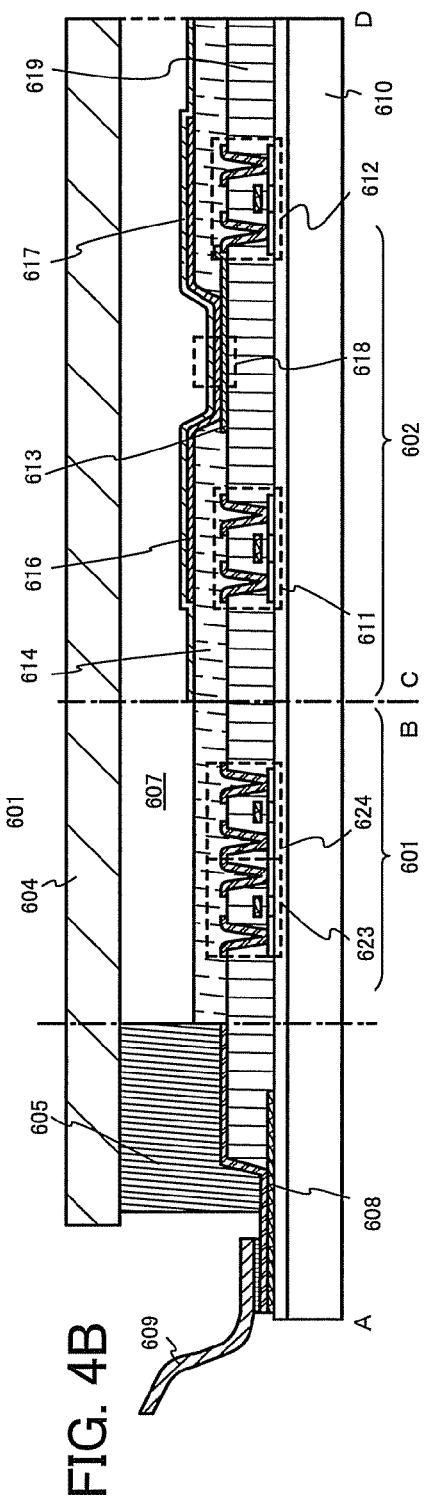
FIG. 4A
FIG. 4B

COMPOSITION, METHOD FOR MANUFACTURING THIN FILM, AND METHOD FOR MANUFACTURING LIGHT-EMITTING ELEMENT

BACKGROUND OF THE INVENTION

1. Field of the Invention

The present invention relates to a composition having an anthracene derivative and a method for forming a thin film in which the composition is used. In addition, the present invention relates to a method for manufacturing a light-emitting element in which electroluminescence is used.

2. Description of the Related Art

As for organic compounds, there are a wider variety of materials and more possibilities to synthesize materials having various functions depending on the molecular design, compared with inorganic compounds. Because of these advantages, photo electronics and electronics using functional organic materials have been attracting attention in recent years.

Examples of electronic devices in which organic compounds are used as functional organic materials include solar cells, light-emitting elements, organic transistors, and the like. These are devices in which electric properties and optical properties of organic compounds are utilized. In particular, tremendous progress in light-emitting elements has been made.

It is said that light emission mechanism of a light-emitting element is as follows: when a voltage is applied between a pair of electrodes with a light-emitting layer interposed therebetween, electrons injected from a cathode and holes injected from an anode are recombined in the light emission center of the light-emitting layer to form a molecular excitons, and energy is released to emit light when the molecular excitons return to a ground state. A singlet excited state and a triplet excited state are known as excited states, and it is considered that light can be emitted through either excited state.

Such light-emitting elements have a lot of material-dependant problems for improvement in element characteristics. In order to solve the problems, improvement in element structures, development of materials, or the like have been carried out.

As a problem of light-emitting elements, improvement in reliability can be given. In particular, it has been difficult to obtain a highly reliable element with the use of a blue light-emitting material that generally has high crystallinity. For example, diphenylanthracene with high fluorescence quantum efficiency has high crystallinity and can not provide a favorable film quality; accordingly, reliability of a light-emitting element that contains diphenylanthracene is low. In order to obtain a material having lower crystallinity and higher stability, a phenylanthracene derivative as an anthracene derivative has been studied (for example, see Patent Document 1).

[References]
[Patent Document]
Patent Document 1: Japanese Published Patent Application No. H8-12600

SUMMARY OF THE INVENTION

A thin film of the above anthracene derivative is typically formed by a vacuum evaporation method that is a dry process and used for a light-emitting element. The vacuum evaporation method, however, has problems, such as low material use efficiency and limitation on the size of a substrate, and thus is unsuitable for industrialization in which high productivity at low cost is required.

As a method that is capable of film formation on a large substrate at relatively low cost, wet processes in which a solution prepared by dissolution of a material in a solvent is used for film formation (a droplet discharging method (also referred to as an ink-jet method) and a coating method (e.g., a spin coating method)) have been proposed.

However, it has been difficult to obtain, using a material such as an anthracene derivative, a thin film that has stability and a favorable film quality by a wet process due to solubility in a solvent and the above problem such as high crystallinity.

Accordingly, an object of an embodiment of the present invention is to provide a composition in which an anthracene derivative is dissolved and a technique in which a thin film that has a favorable film quality is formed using the composition by a wet process. Further, another object of an embodiment of the present invention is to manufacture a highly reliable light-emitting element using the composition at low cost with high productivity.

The present inventors have found that using a composition in which an anthracene derivative having one anthracene structure and one carbazolyl group which is bonded to the anthracene structure directly or through a phenyl group is dissolved in a solvent, a thin film which has no defect in shape and has a favorable film quality can be formed by a wet process. Detailed description is made below.

One embodiment of the present invention is a composition having a solvent and an anthracene derivative represented by a general forlnula (G31-1).

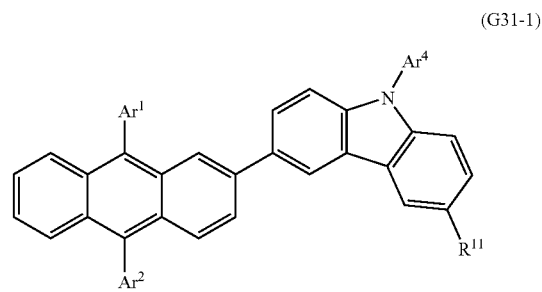

(G31-1)

In the formula, $Ar^1$ and $Ar^2$ each represent a substituted or unsubstituted aryl group having 6 to 13 carbon atoms, $Ar^4$ represents a substituted or unsubstituted aryl group having 6 to 13 carbon atoms, and $R^{11}$ represents hydrogen, an alkyl group having 1 to 4 carbon atoms, or a substituted or unsubstituted aryl group having 6 to 13 carbon atoms.

One mode of the present invention is a composition having a solvent and an anthracene derivative represented by a general formula (G31-2).

(G31-2)

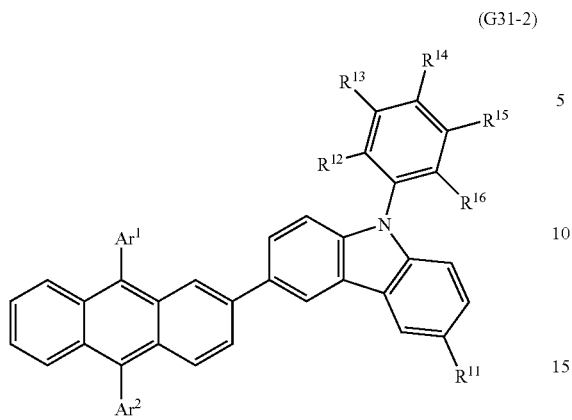

(G32-1)

In the formula, Ar$^1$ and Ar$^2$ each represent a substituted or unsubstituted aryl group having 6 to 13 carbon atoms, Ar$^4$ represents a substituted or unsubstituted aryl group having 6 to 13 carbon atoms, and R$^{11}$ represents hydrogen, an alkyl group having 1 to 4 carbon atoms, or a substituted or unsubstituted aryl group having 6 to 13 carbon atoms.

One mode of the present invention is a composition having a solvent and an anthracene derivative represented by a general formula (G31-3).

In the formula, Ar$^1$ and Ar$^2$ each represent a substituted or unsubstituted aryl group having 6 to 13 carbon atoms, and R$^1$ and R$^2$ each represent hydrogen, an alkyl group having 1 to 4 carbon atoms, or a substituted or unsubstituted aryl group having 6 to 13 carbon atoms.

One mode of the present invention is a composition having a solvent and an anthracene derivative represented by a general formula (G33-1).

(G31-3)

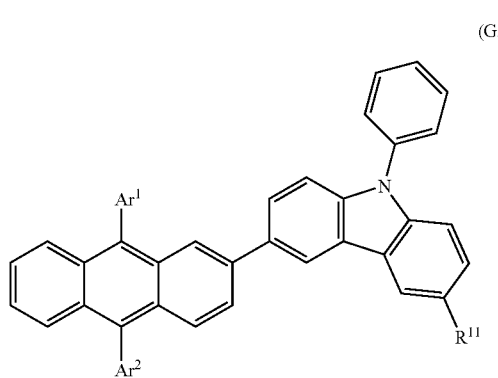

(G33-1)

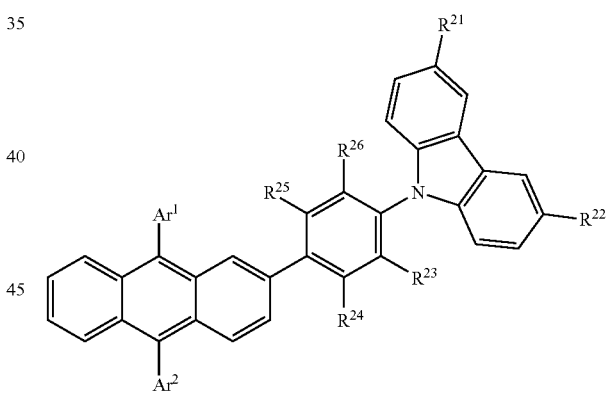

In the formula, Ar$^1$ and Ar$^2$ each represent a substituted or unsubstituted aryl group having 6 to 13 carbon atoms, Ar$^4$ represents a substituted or unsubstituted aryl group having 6 to 13 carbon atoms, and R$^{11}$ represents hydrogen, an alkyl group having 1 to 4 carbon atoms, or a substituted or unsubstituted aryl group having 6 to 13 carbon atoms.

One mode of the present invention is a composition having a solvent and an anthracene derivative represented by a general formula (G32-1).

In the formula, Ar$^1$ and Ar$^2$ each represent a substituted or unsubstituted aryl group having 6 to 13 carbon atoms, R$^2$ and 122 each represent hydrogen, an alkyl group having 1 to 4 carbon atoms, or a substituted or unsubstituted aryl group having 6 to 13 carbon atoms, and R$^{23}$ to R$^{26}$ each represent hydrogen, an alkyl group having 1 to 4 carbon atoms, or a substituted or unsubstituted phenyl group.

One mode of the present invention is a composition having a solvent and an anthracene derivative represented by a general formula (G33-2).

(G33-2)

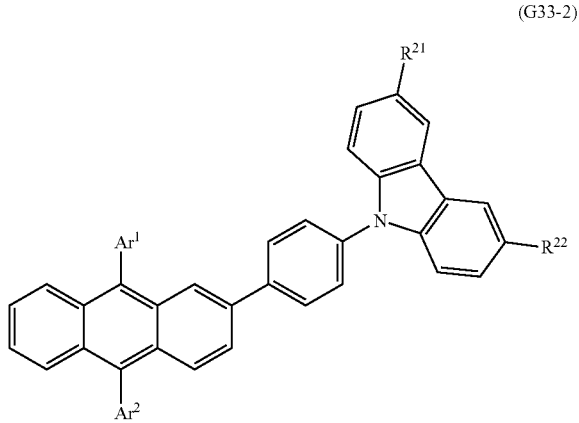

In the formula, $Ar^1$ and $Ar^2$ each represent a substituted or unsubstituted aryl group having 6 to 13 carbon atoms, and $R^{21}$ and $R^{22}$ each represent hydrogen, an alkyl group having 1 to 4 carbon atoms, or a substituted or unsubstituted aryl group having 6 to 13 carbon atoms.

In the above-described compositions, a variety of solvents can be used. For example, the anthracene derivatives can be dissolved in solvents that have aromatic rings (e.g., a benzene ring), such as toluene, xylene, methoxybenzene (anisole), dodecylbenzene, or a mixed solvent of dodecylbenzene and tetralin. The above-described anthracene derivatives can also be dissolved in organic solvents that do not have aromatic rings, such as dimethylsulfoxide (DMSO), dimethylformamide (DMF), or chloroform.

As other solvents, ketone solvents such as acetone, methyl ethyl ketone, diethyl ketone, n-propyl methyl ketone, and cyclohexanone; ester solvents such as ethyl acetate, n-propyl acetate, n-butyl acetate, ethyl propionate, γ-butyrolactone, and diethyl carbonate; ether solvents such as diethylether, tetrahydrofuran and dioxane; alcohol solvents such as ethanol, isopropanol, 2-methoxyethanol, and 2-ethoxyethanol; and the like can be given.

Further, the present invention also includes a method for forming a thin film using any of the above compositions. In one mode of a method for forming a thin film of the present invention, any of the compositions is applied to a substrate, and the solvent is removed.

In one mode of a method for forming a thin film of the present invention, any of the compositions is applied to a substrate, and the solvent is removed by heat treatment.

Furthermore, the present invention also includes a method for manufacturing a light-emitting element using any of the above compositions. According to one mode of a method for manufacturing a light-emitting element of the present invention, a first electrode is formed; a layer containing a light-emitting substance is formed by application of any of the compositions to the first electrode and then removal of the solvent; and a second electrode is formed over the layer containing a light-emitting substance. The light-emitting element may be manufactured so that it includes functional layers, which can be formed by a wet process or a dry process on the first electrode side and/or second electrode side of the layer containing a light-emitting substance.

A light-emitting device of the present invention can be manufactured using the light-emitting element of the present invention. The light-emitting device can be made to have a light-emitting element that includes a thin film formed using any of the above compositions and a control unit configured to control light emission of the light-emitting element. The light-emitting device in this specification includes an image display device, a light-emitting device, and a light source (including a lighting apparatus). Further, the light-emitting devices include all of the following modules: modules in which a connector such as an FPC (flexible printed circuit), TAB (tape automated bonding) tape, or a TCP (tape carrier package) is attached to a panel; modules having TAB tape or a TCP provided with a printed wiring board at the end thereof; and modules having an IC (integrated circuit) directly mounted on a panel provided with a light-emitting element by a COG (chip on glass) method.

Furthermore, an electronic device in which the light-emitting element is used for its display portion according to the present invention can be manufactured. Accordingly, one mode of the present invention is an electronic device that includes a display portion, and the display portion can be made to have the above-described light-emitting element and a control unit configured to control light emission of the light-emitting element.

A thin film formed by a wet process with the use of the composition of the present invention in which one mode of anthracene derivatives is dissolved in a solvent can be made to have a favorable film quality without defects or the like. Thus, with the use of such a composition and a thin film, a highly reliable light-emitting element can be manufactured.

Further, since a wet process is employed for manufacture of a thin film and a light-emitting element, high material use efficiency and a reduction in expensive facilities such as a large vacuum apparatus can be achieved, resulting in low cost and high productivity. Thus, by use of the present invention, a light-emitting device and an electronic device that are highly reliable can be manufactured at low cost with high productivity.

BRIEF DESCRIPTION OF DRAWINGS

In the accompanying drawings:
FIGS. 4A and 4B are views illustrating a light-emitting device.

DETAILED DESCRIPTION OF THE INVENTION

Figure 1A:
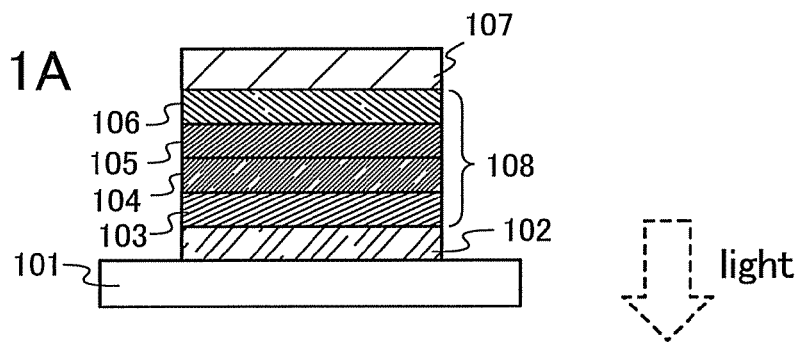
FIGS. 1A to 1C are views each illustrating a light emitting element.

Hereinafter, embodiments of the present invention will be described in detail with reference to the drawings. The present invention is not limited to the following description, and it is easily understood by those skilled in the art that modes and details herein disclosed can be modified in various ways without departing from the spirit and the scope of the present invention. Therefore, the present invention should not be construed as being limited to the description of the following embodiments and examples.

In one embodiment of an anthracene derivative contained in any of the compositions of the present invention, the anthracene derivative has one anthracene structre and one carbazolyl group which is bonded to the anthracene structure directly or through a phenyl group. A thin film formed by a wet process with the use of any of the compositions, in which the anthracene derivative is dissolved in a solvent, can be made to have a favorable film quality without defects or the like. Hereinafter, embodiments of the present invention is specifically described.

[Embodiment 1]

In this embodiment, compositions of the present invention and an example of a method for forming a thin film using any of the compositions are described.

An anthracene derivative contained in any of the compositions of this embodiment has a feature that it has one anthracene structure and one carbazolyl group, and the carbazolyl group and the anthracence structure are bonded through a phenyl group.

An anthracene derivative contained in any of the compositions of this embodiment, as described above, is specifically represented by any of the following general formulae (G33-1) and (G33-2).

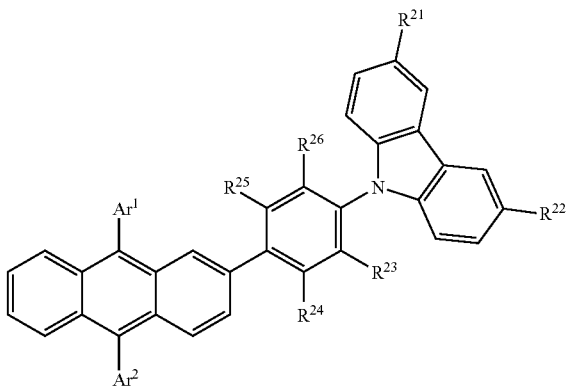

(G33-1)

In the formula, $Ar^1$ and $Ar^2$ each represent a substituted or unsubstituted aryl group having 6 to 13 carbon atoms, $R^{21}$ and $R^{22}$ each represent hydrogen, an alkyl group having 1 to 4 carbon atoms, or a substituted or unsubstituted aryl group having 6 to 13 carbon atoms, and $R^{23}$ to $R^{26}$ each represent hydrogen, an alkyl group having 1 to 4 carbon atoms, or a substituted or unsubstituted phenyl group.

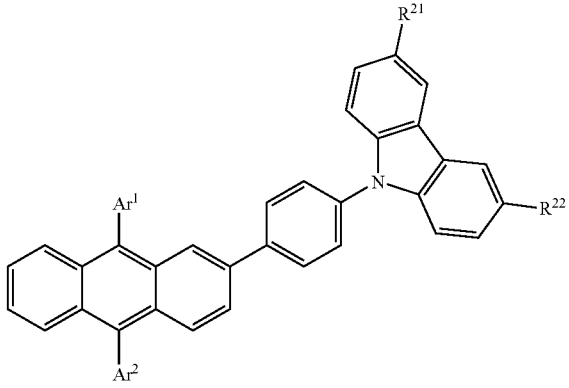

(G33-2)

In the formula, $Ar^1$ and $Ar^2$ each represent a substituted or unsubstituted aryl group having 6 to 13 carbon atoms, and $R^{21}$ and $R^{22}$ each represent hydrogen, an alkyl group having 1 to 4 carbon atoms, or a substituted or unsubstituted aryl group having 6 to 13 carbon atoms.

Note that the carbon atoms of the aryl group described in this specification refer to carbon atoms that form a ring of the main skeleton, and carbon atoms of a substituent bonded thereto are not included therein. As examples of a substituent bonded to the aryl group, there are an alkyl group having 1 to 4 carbon atoms and an aryl group having 6 to 13 carbon atoms; specifically, there are a methyl group, an ethyl group, a propyl group, a butyl group, a phenyl group, a naphthyl group, a fluorenyl group, and the like. Further, the aryl group may have one or more substituents. If the aryl group has two substituents, the substituents may be bonded to each other to form a ring. For example, in the case where an aryl group is a fluorenyl group, carbon at a 9-position may include two phenyl groups, and the two phenyl groups may be bonded to each other to form a spiro ring structure.

In each of the general formulae (G33-1) and (G33-2), an aryl group having 6 to 13 carbon atoms may have a substituent. If the aryl group having 6 to 13 carbon atoms has a plurality of substituents, the substituents may be bonded to form a ring. Further, if a carbon atom has two substituents, the substituents may be bonded to each other to form a spiro ring. For example, there are substituents represented by structural formulae (11-1) to (11-16).

(11-1)

(11-2)

(11-3)

(11-4)

(11-5)

(11-6)

(11-7)
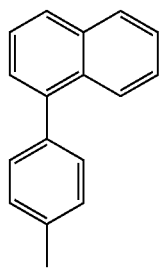

(11-8)
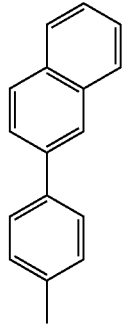

(11-9)
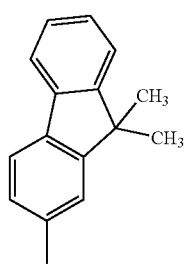

(11-10)
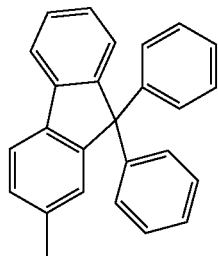

(11-11)
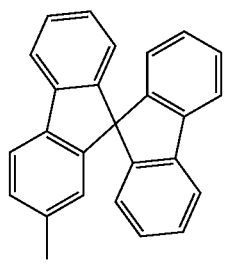

(11-12)
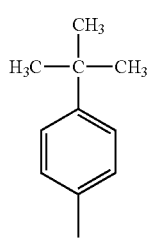

(11-13)
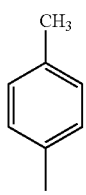

(11-14)
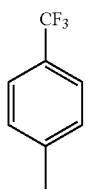

(11-15)
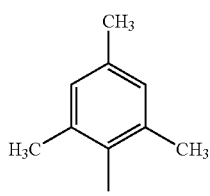

(11-16)
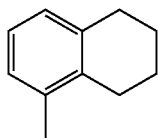

Further, in the anthracene derivative represented by any of the general formulae (G33-1) and (G33-2), Ar¹ and Ar² are preferably substituents having the same structure, for ease of synthesis and purification.

As specific examples of the anthracene derivatives represented by the general formulae (G33-1) and (G33-2), anthracene derivatives represented by structural formulae (201) to (220) can be given. However, the present invention is not limited thereto.

(201)
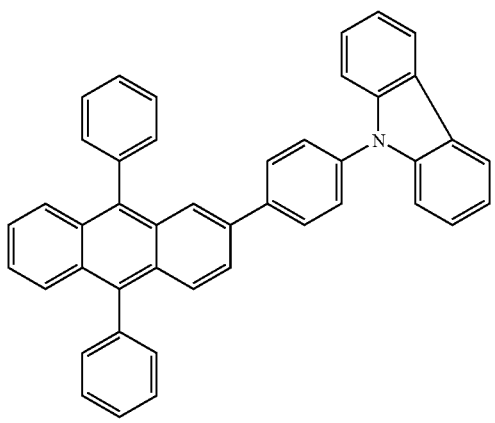

(202)
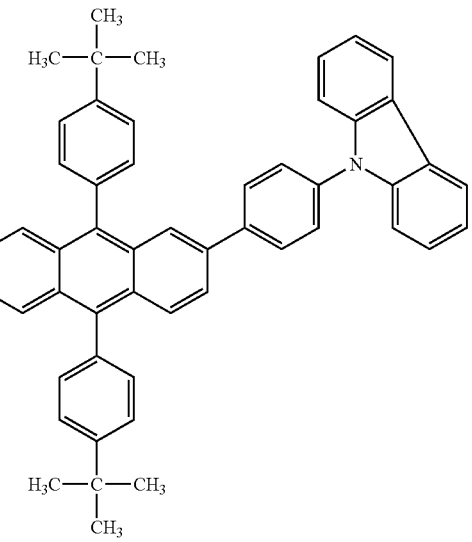

(203)
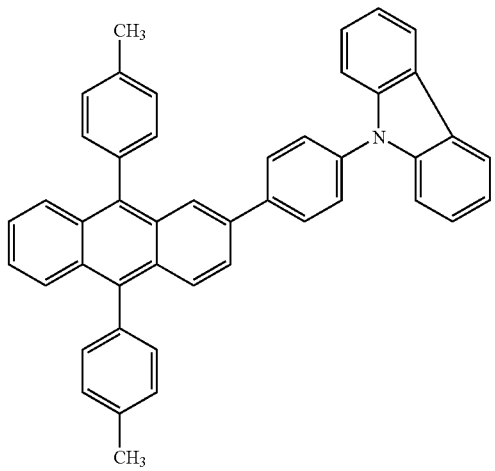

(204)
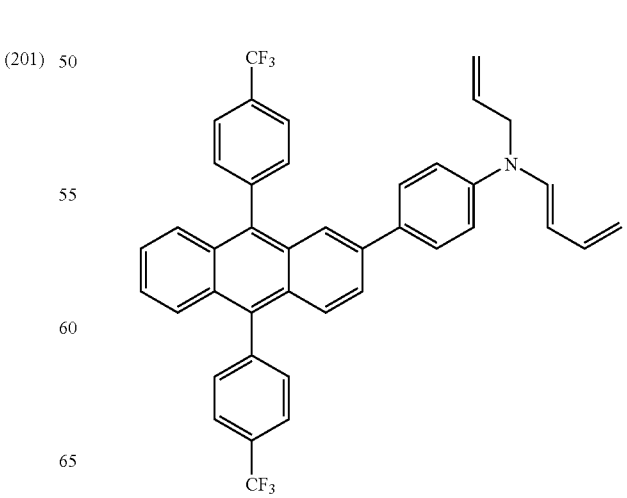

(205)
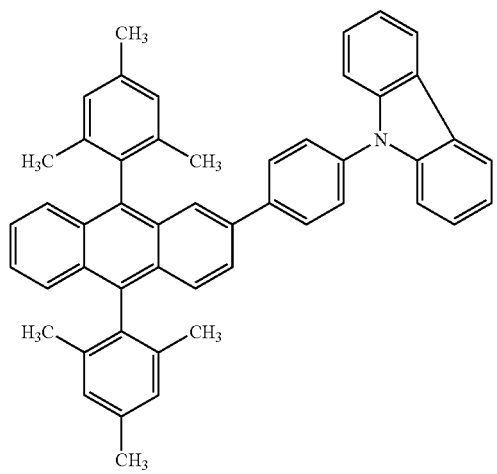
(206)
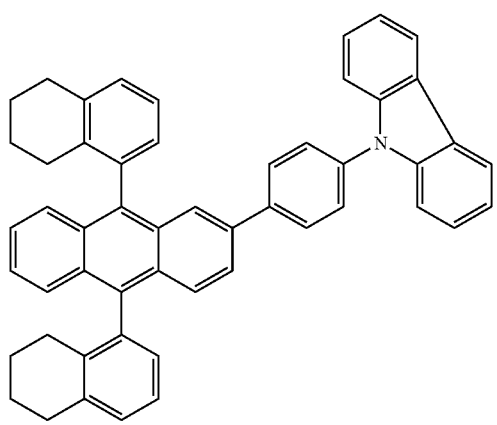
(207)
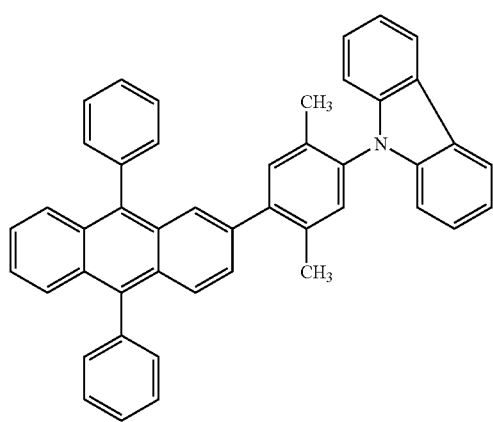
(208)
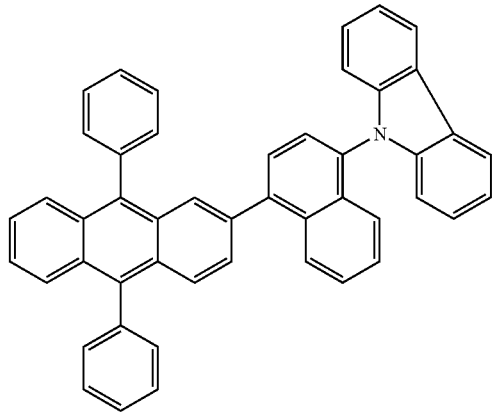
(209)
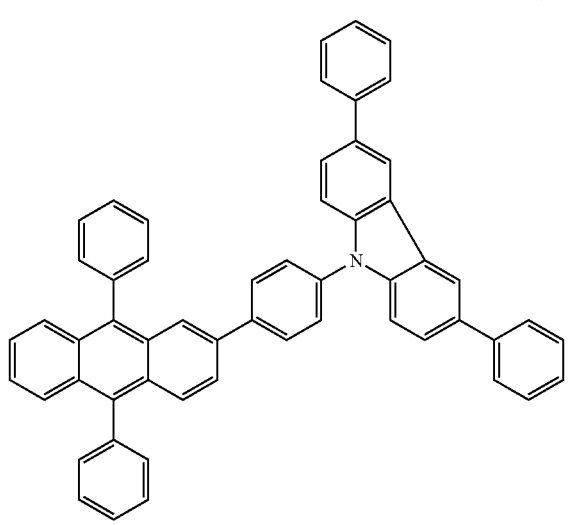
(210)
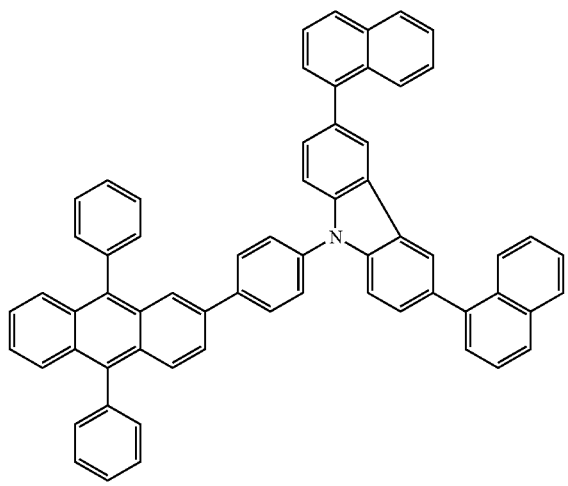

(211)
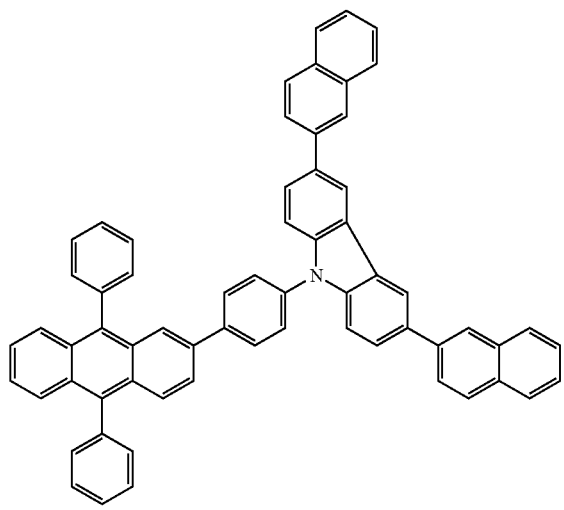
(212)
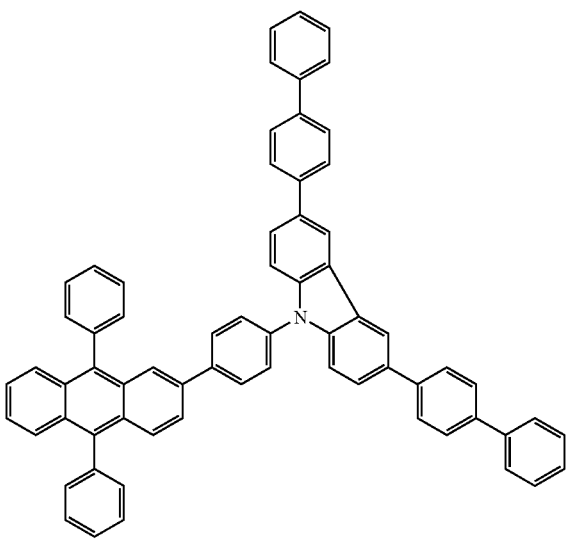
(213)
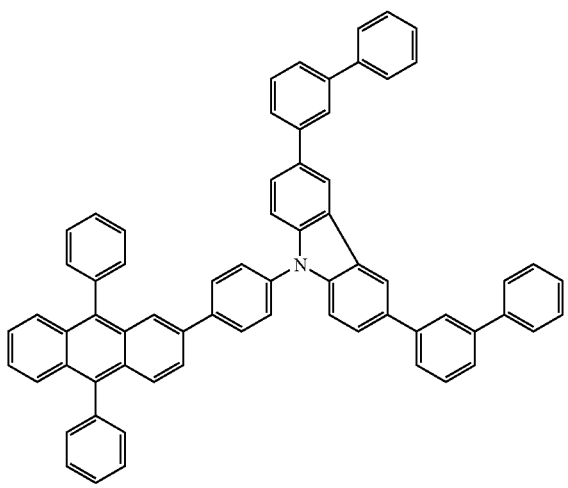
(214)
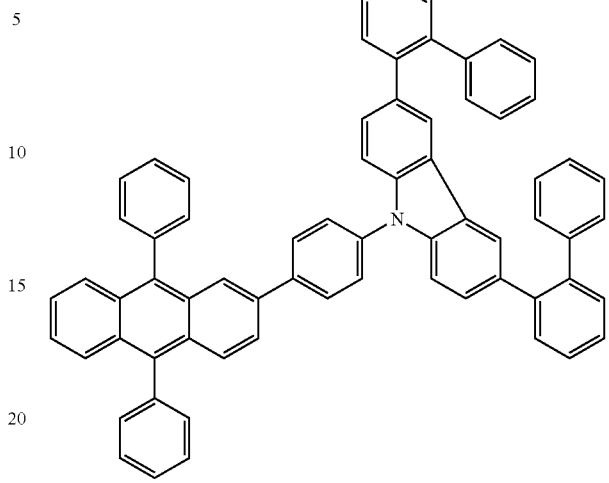
(215)
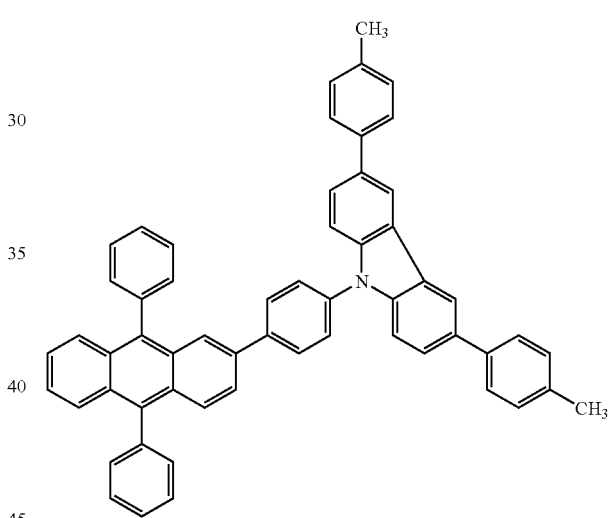
(216)
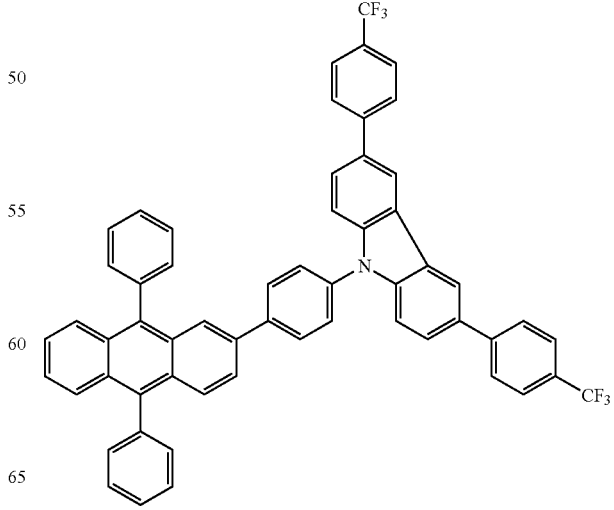

(217)

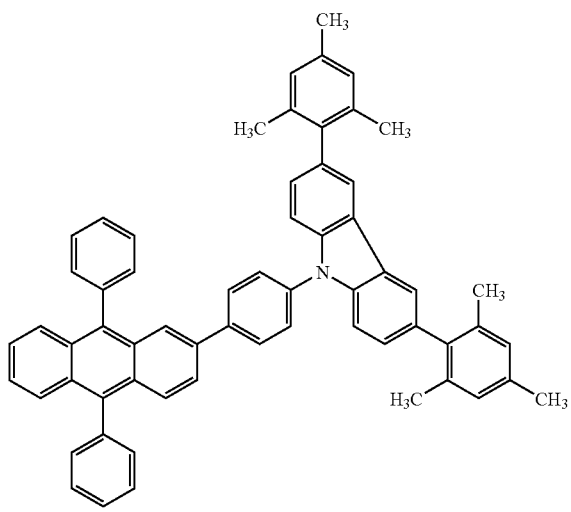

(218)

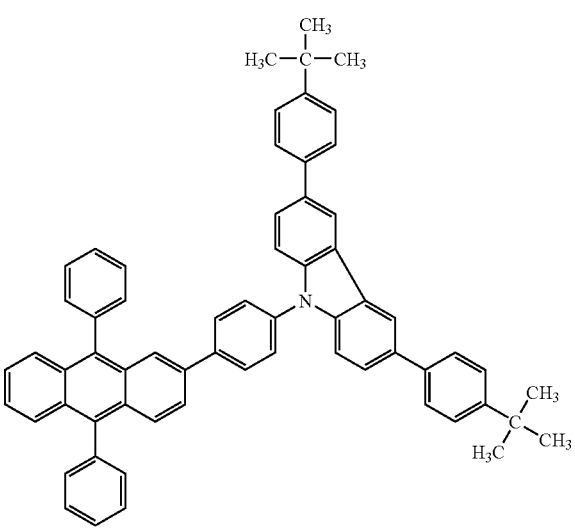

(219)

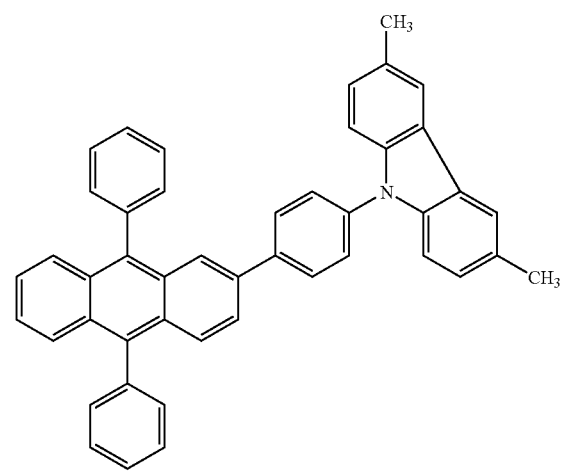

(220)

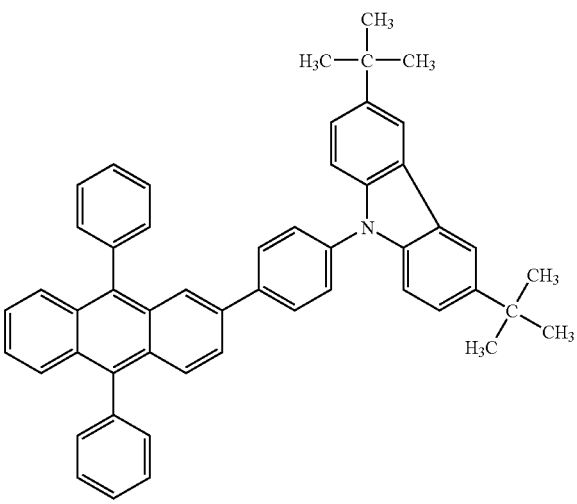

The anthracene derivative contained in any of the compositions of this embodiment may have one anthracene structure and one carbazolyl group, and the carbazolyl group may be bonded to the 9-position or the 10-position of the anthracene structure through a phenyl group. As specific examples of the anthracene derivative, anthracene derivatives represented by structural formulae (311) to (399) can be given. Of course, the present invention is not limited thereto. In structural formulae of this specification, t-Bu indicates a tert-butyl group and Ph indicates a phenyl group.

(311)

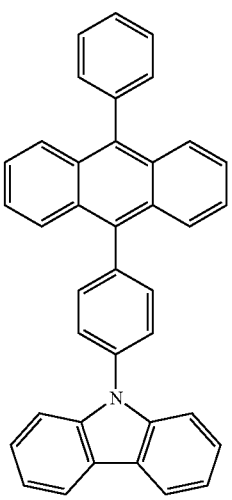

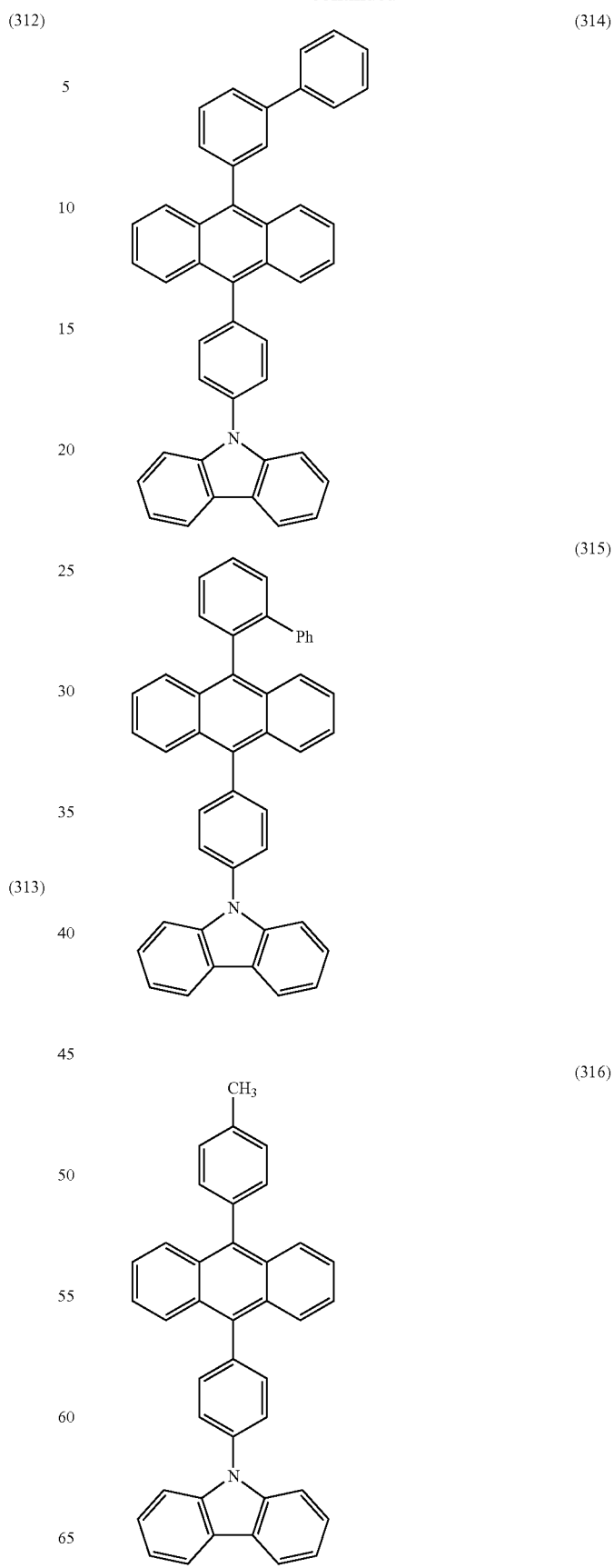

(317)
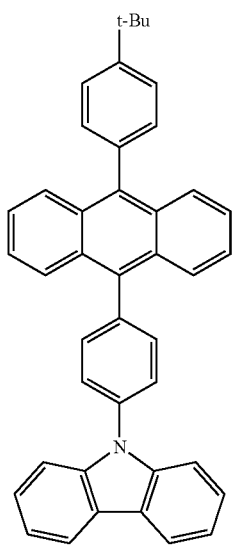
(318)
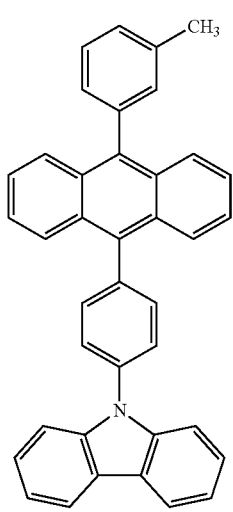
(319)
(320)
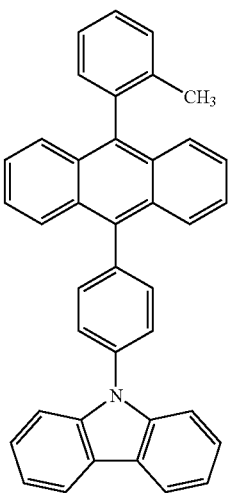
(321)
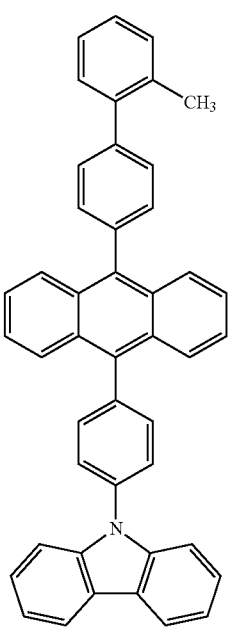

(322)
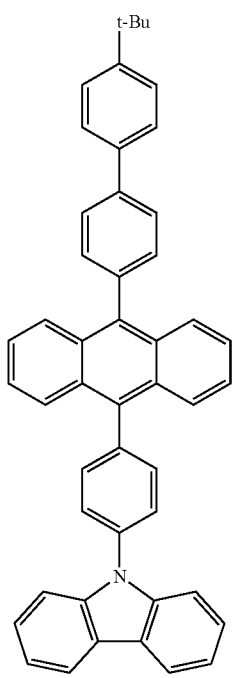
(324)
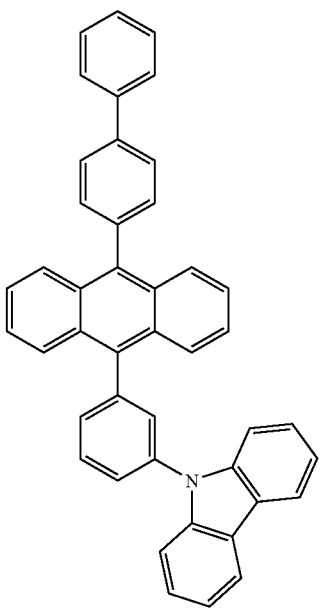
(323)
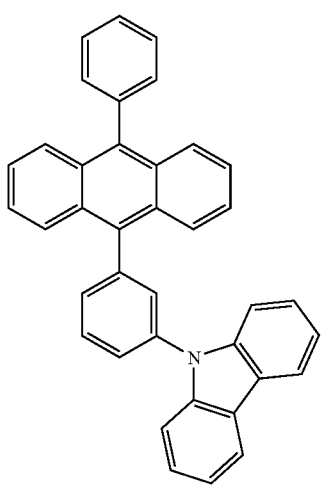
(325)

(326)
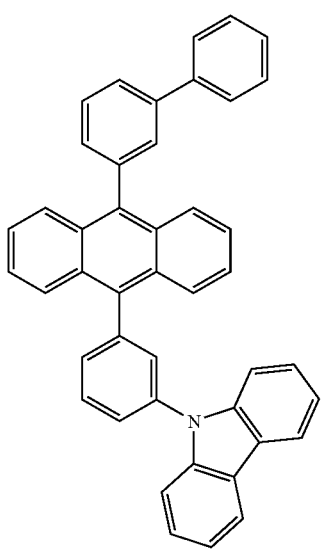
(327)
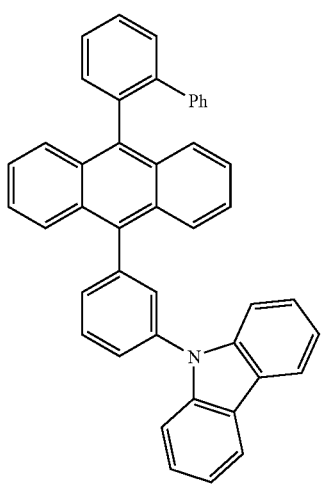
(328)
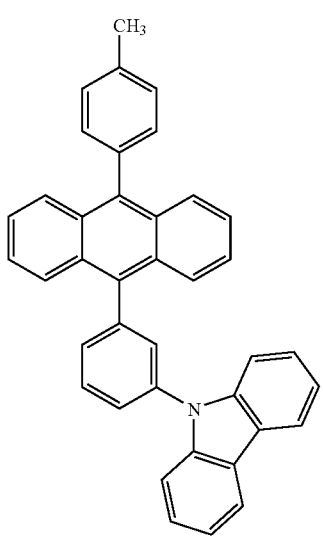
(329)
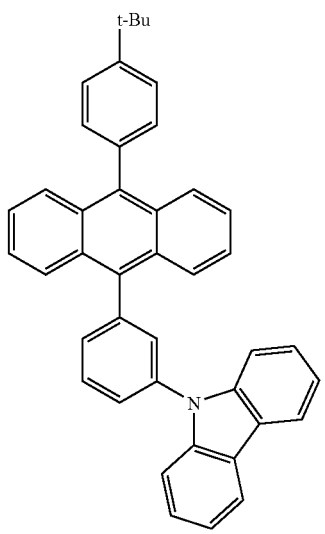
(330)
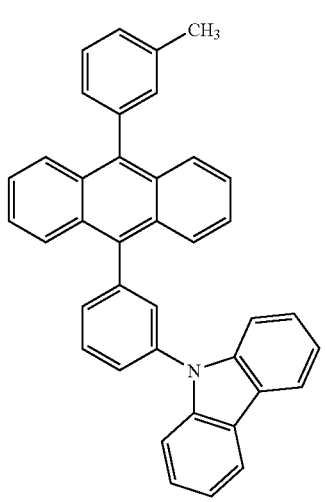
(331)
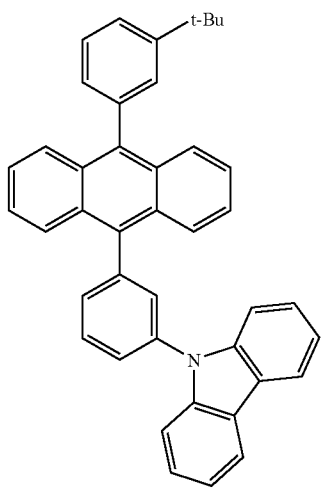

(332)
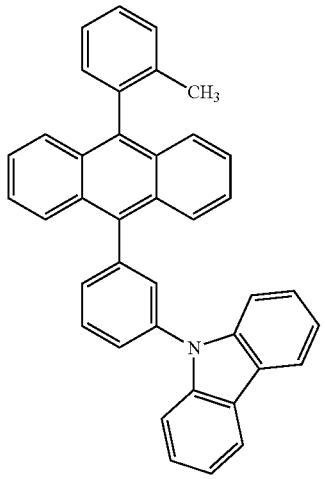
(333)
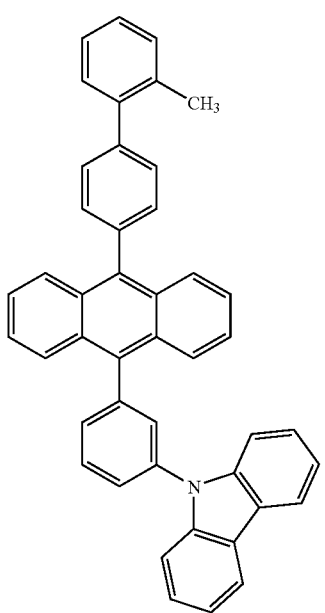
(334)
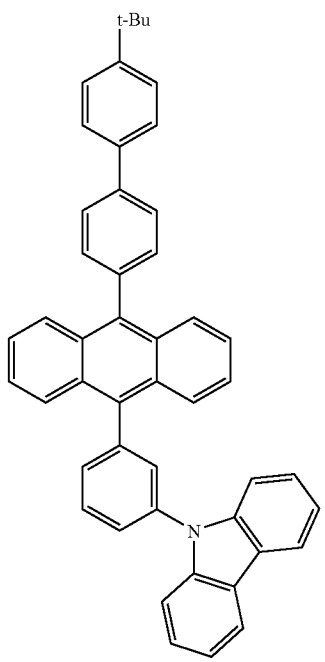
(335)
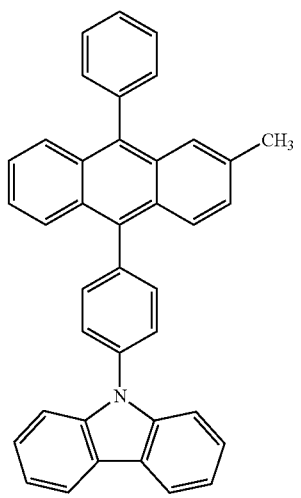
(336)

(337)
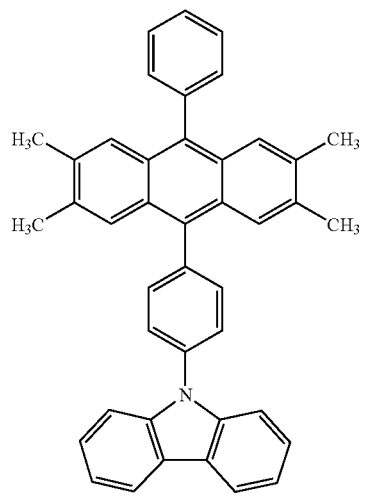
(338)
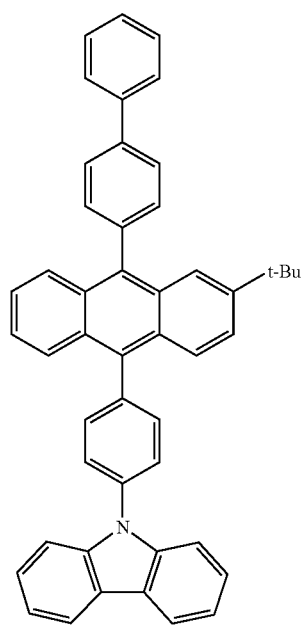
(339)
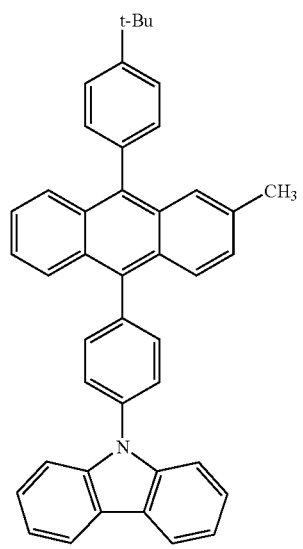
(340)
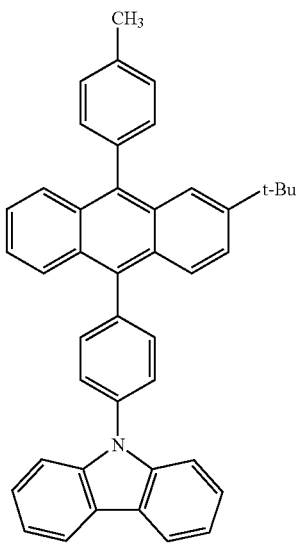
(341)
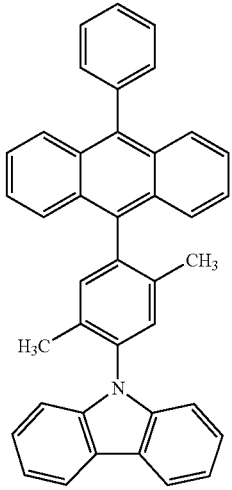
(342)
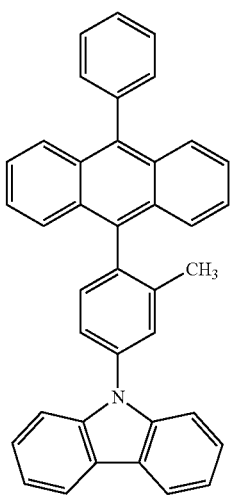

(343)
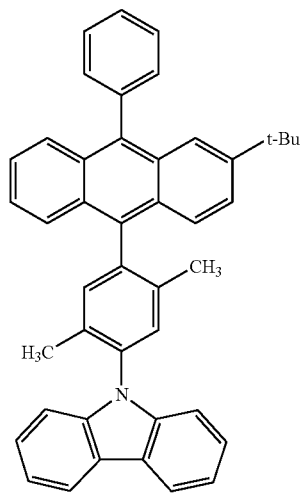
(344)
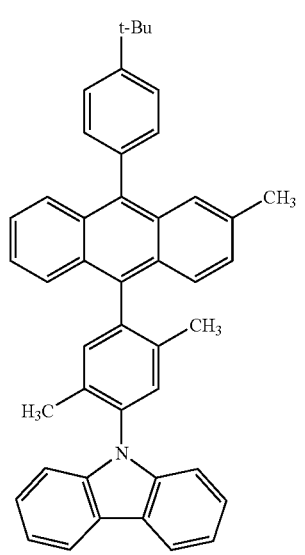
(345)
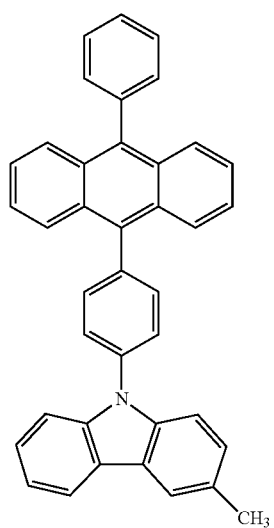
(346)
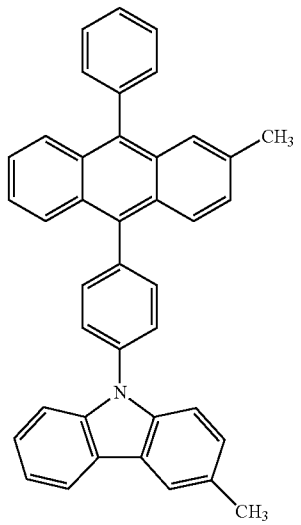
(347)
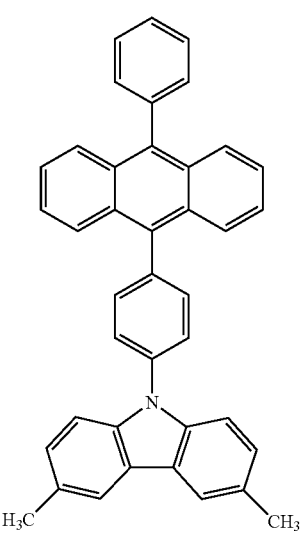
(348)
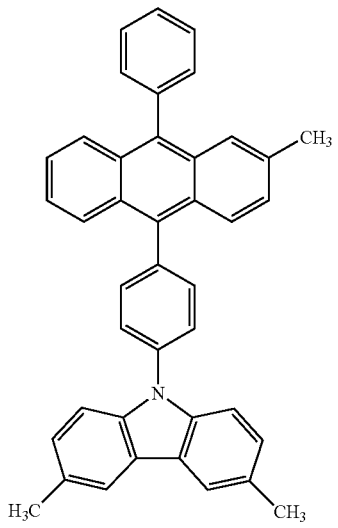

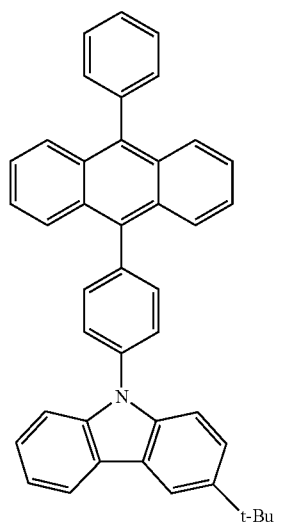
(349)
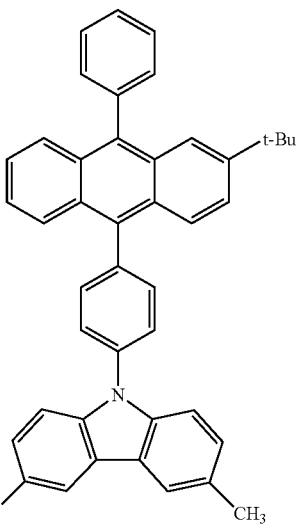
(352)
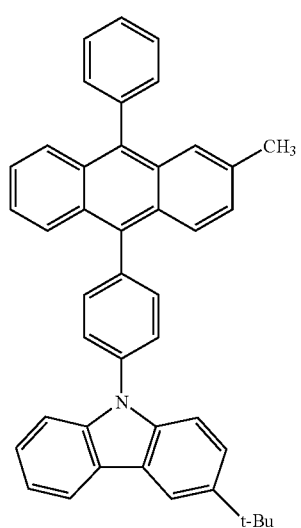
(350)
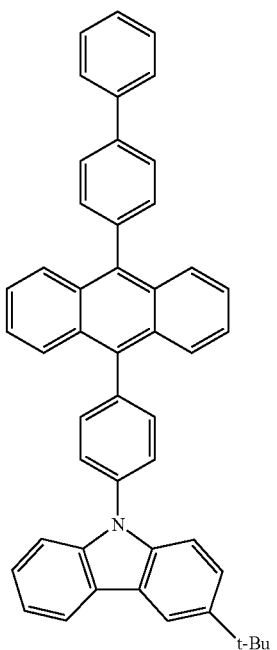
(353)
(351)

(354)
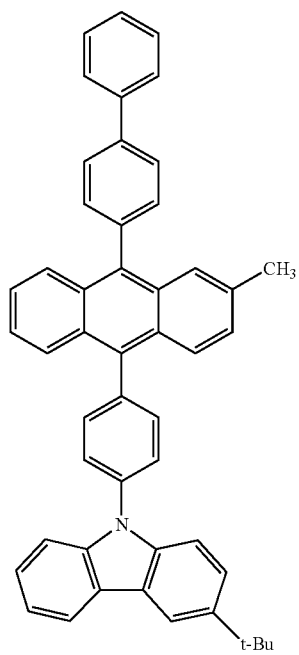
(356)
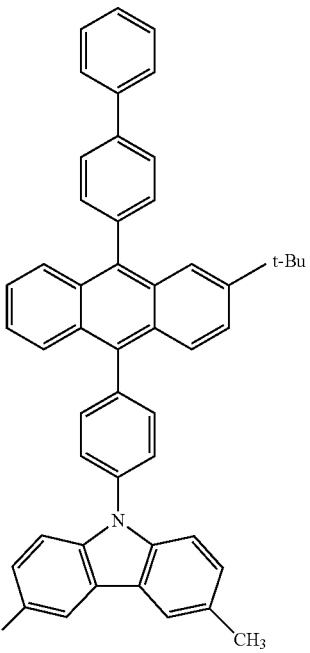
(355)
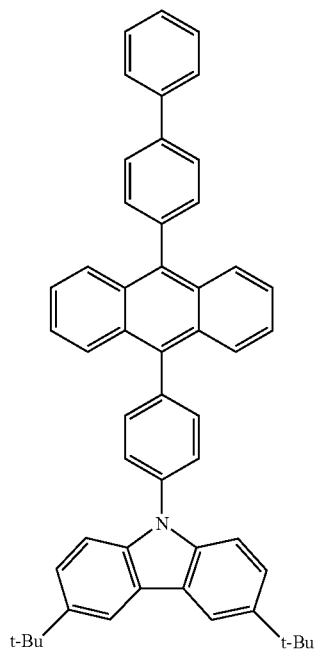
(357)
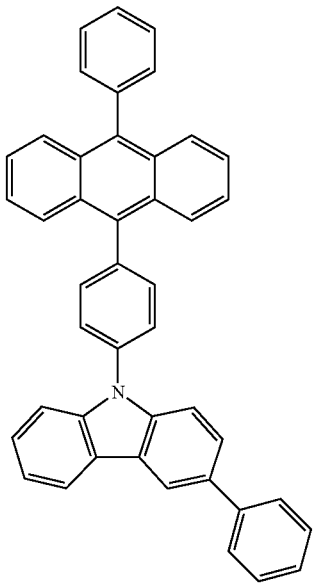

(358)
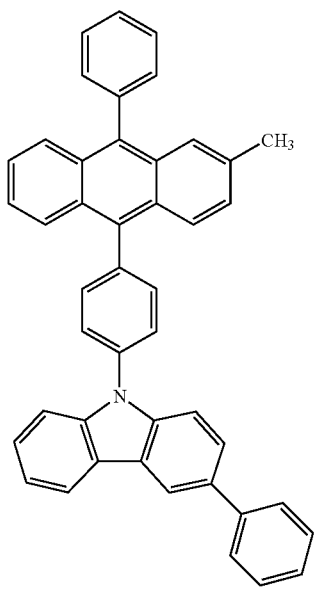
(360)
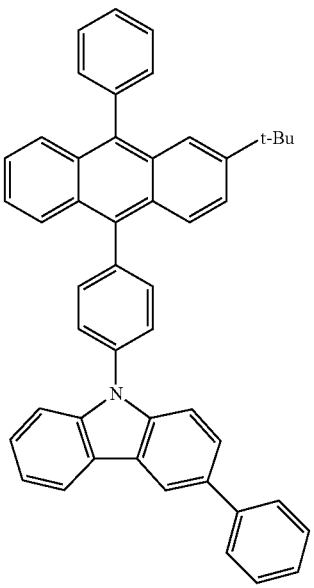
(359)
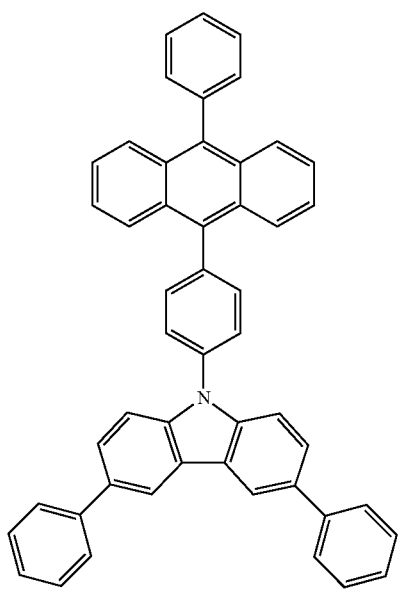
(361)
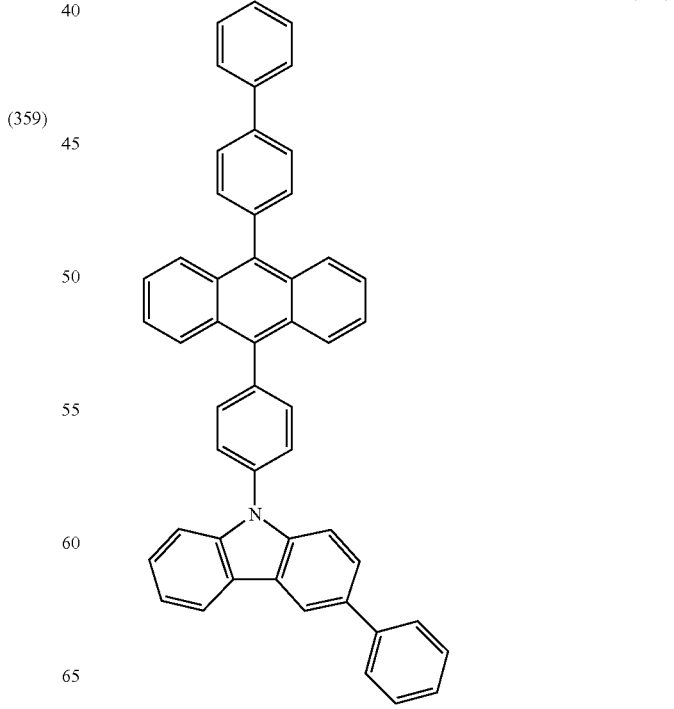

(362)
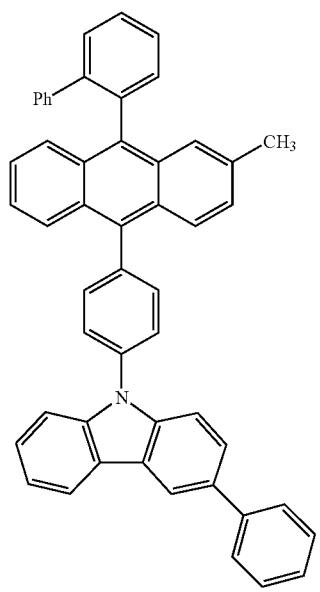
(363)
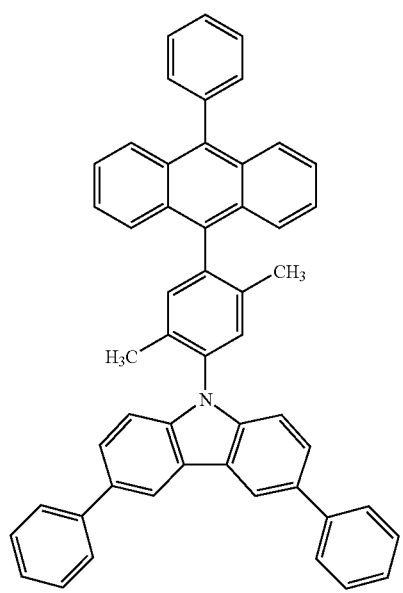
(364)
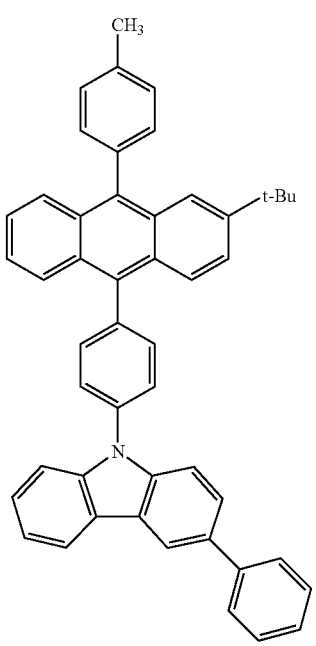
(365)
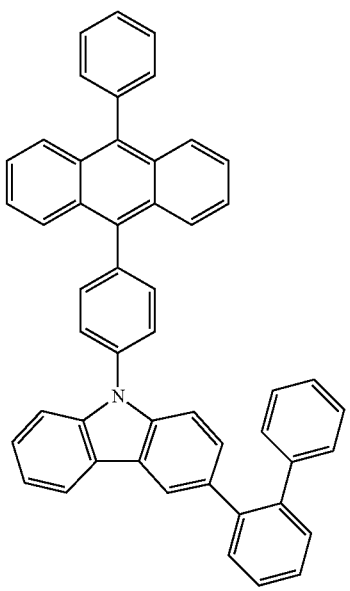

-continued
(366)
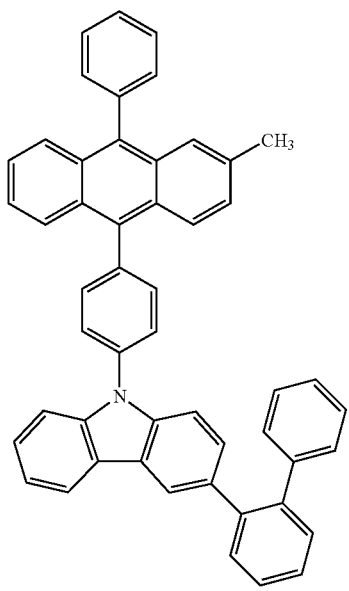
(367)
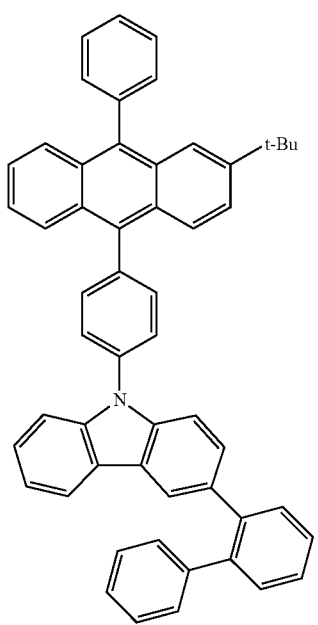
(368)
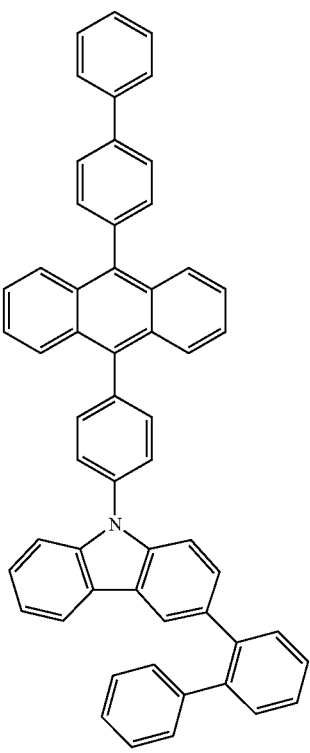
(369)
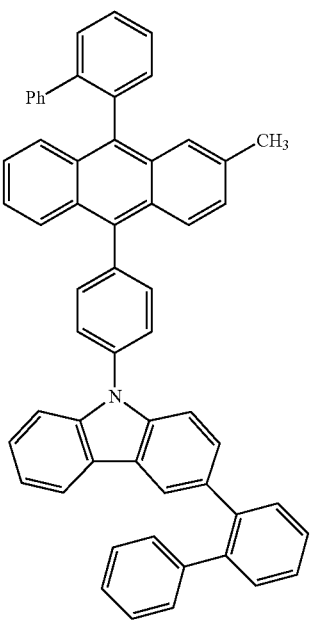

(370) 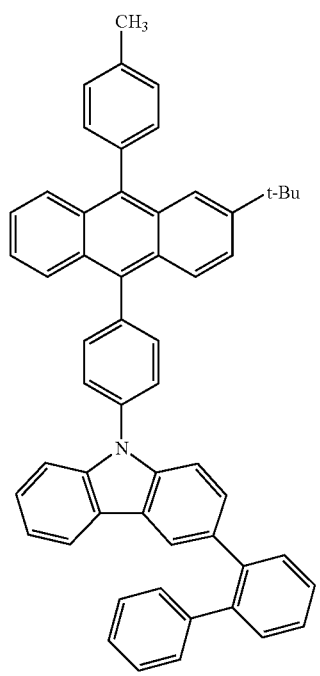
(372) 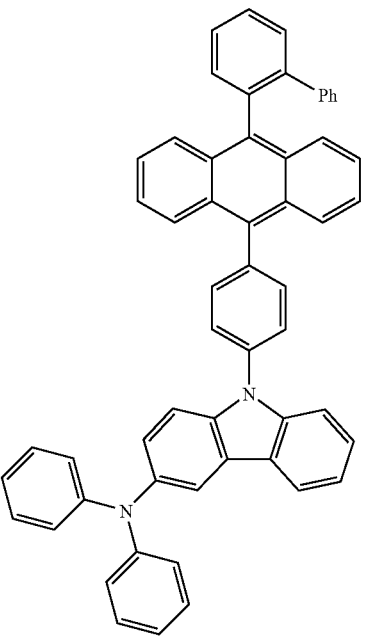
(371) 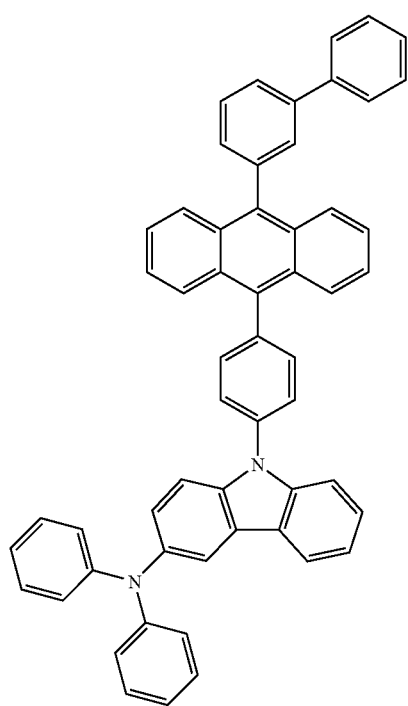
(373) 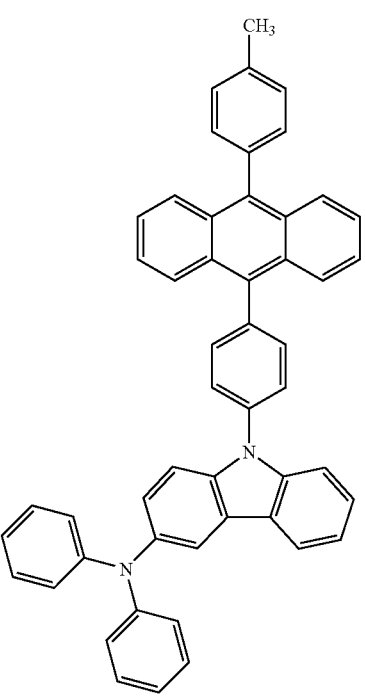

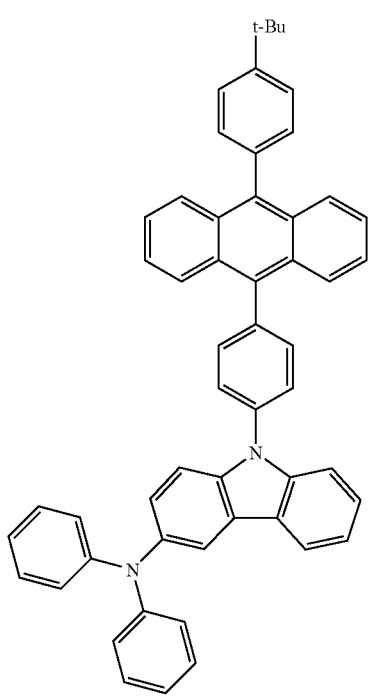
(374)
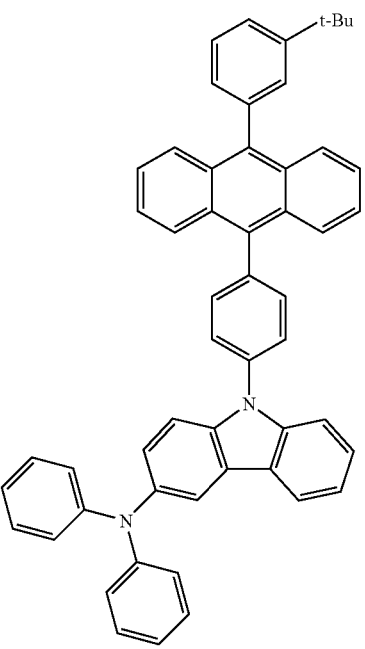
(376)
(375)
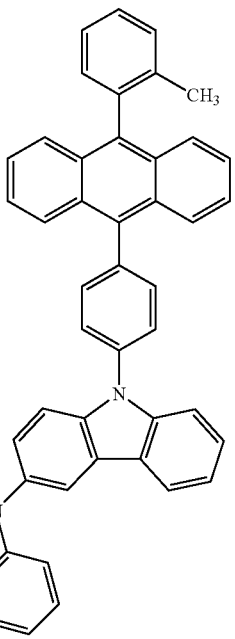
(377)

(378)
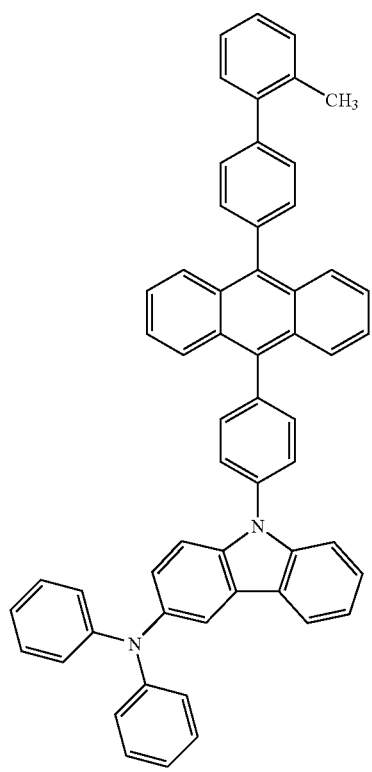
(379)
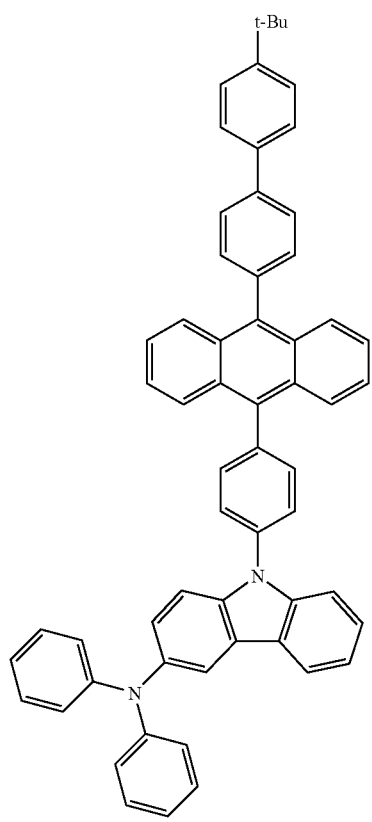
(380)
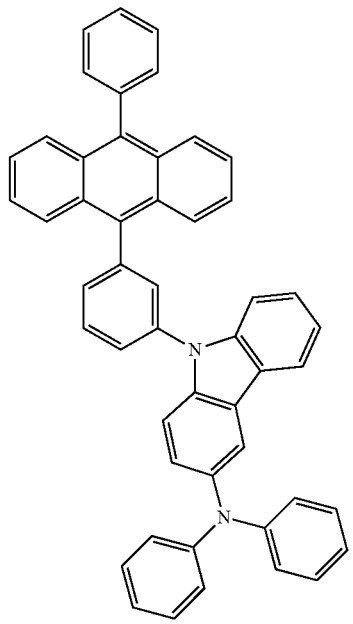
(381)
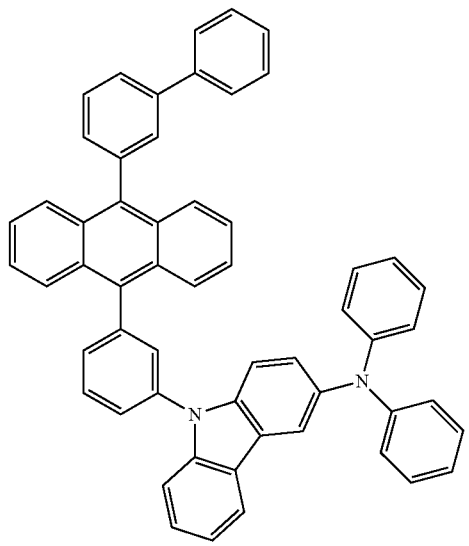
(382)
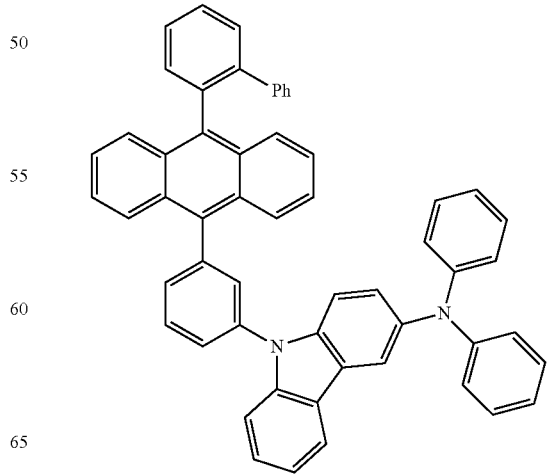

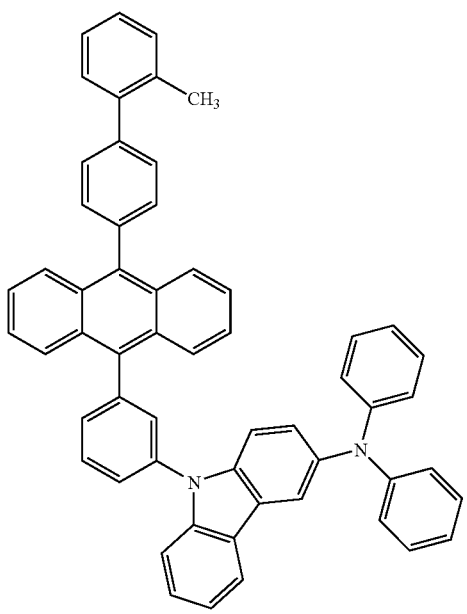
(383)
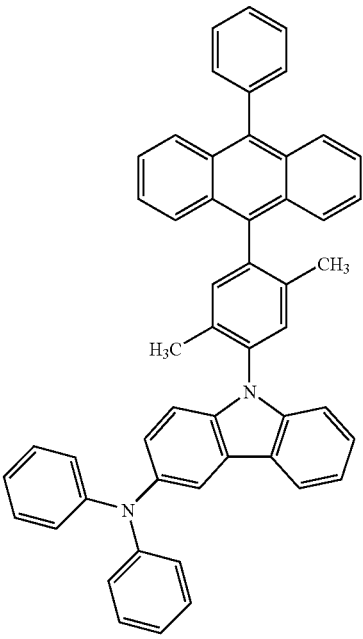
(385)
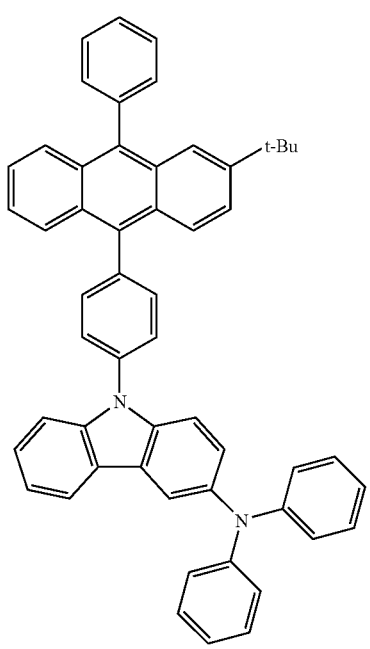
(384)
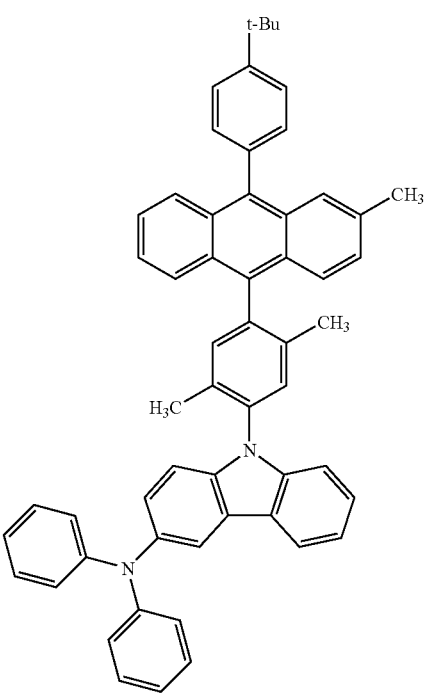
(386)

(387)
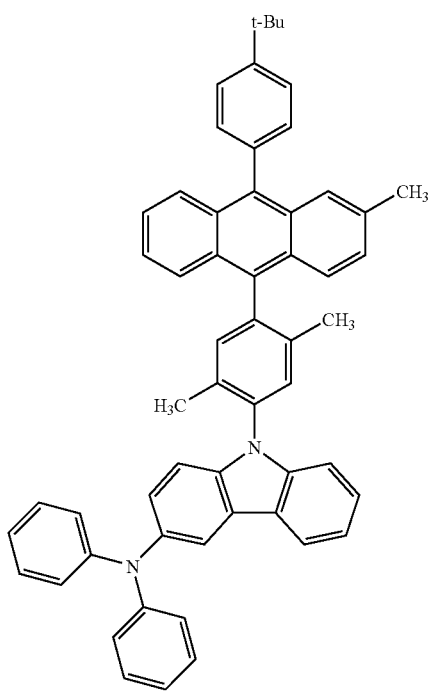
(388)
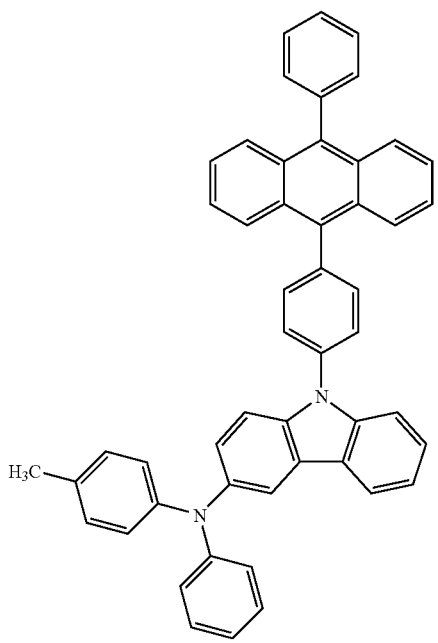
(389)
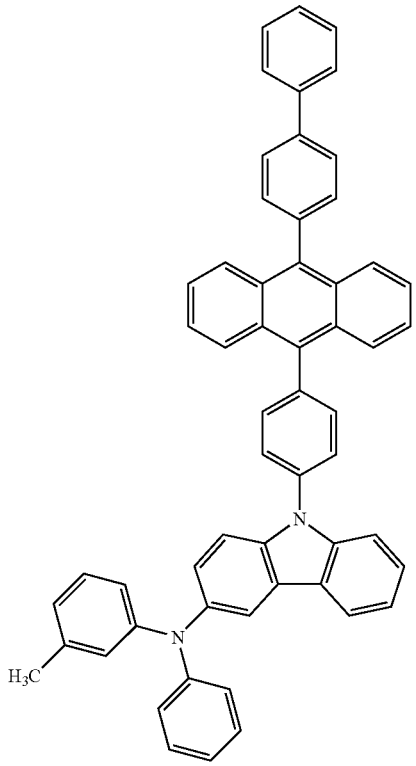
(390)
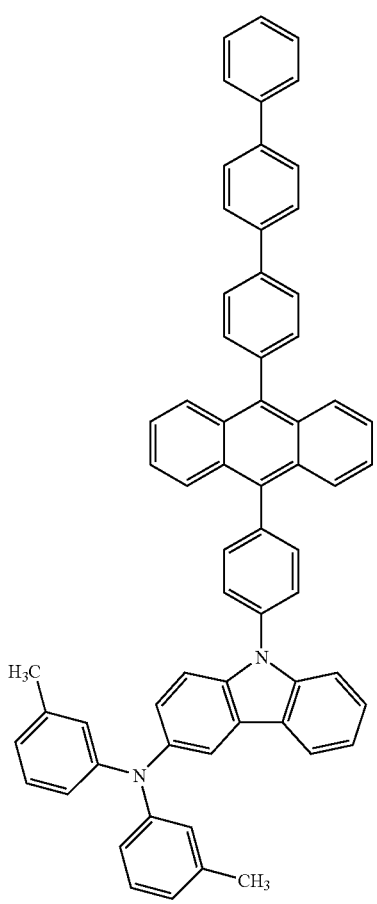

-continued
(391)
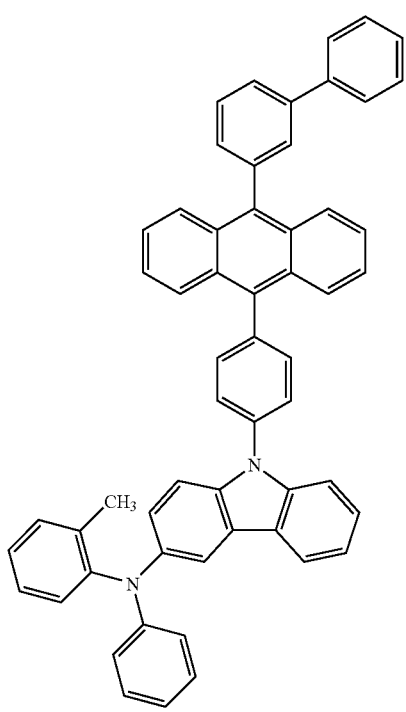
(392)
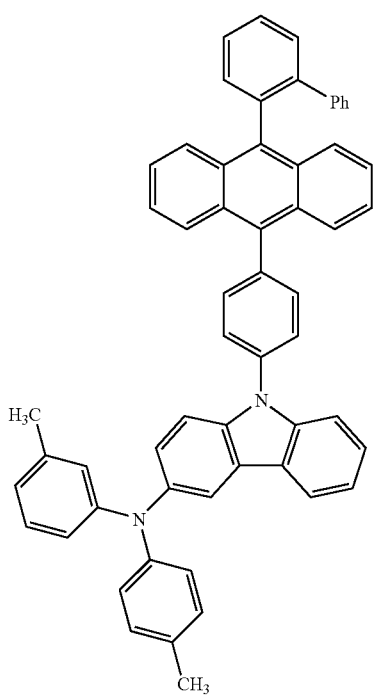
(393)
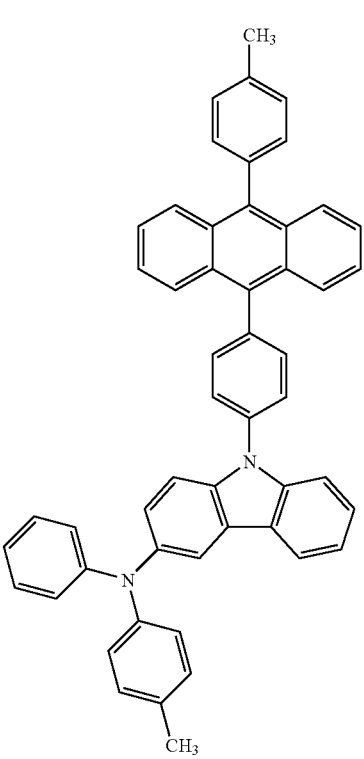
(394)
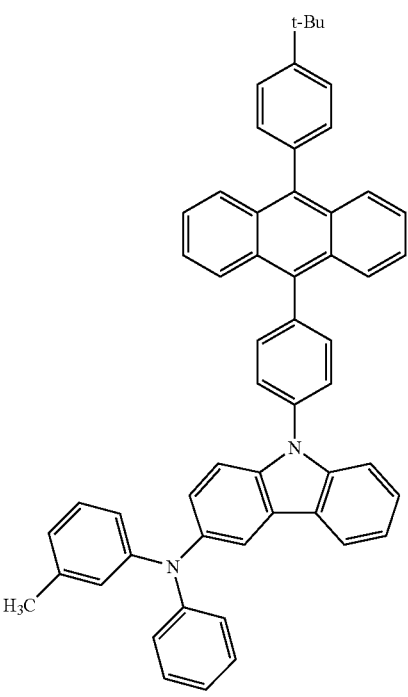

-continued
(395)
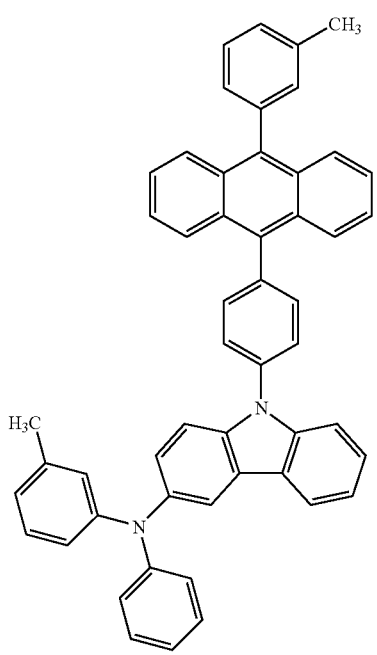
(396)
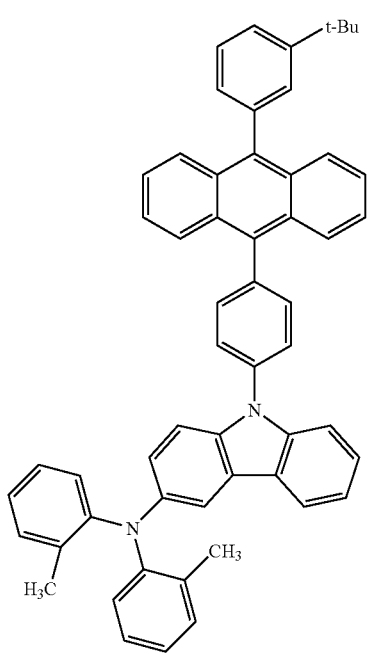
(397)
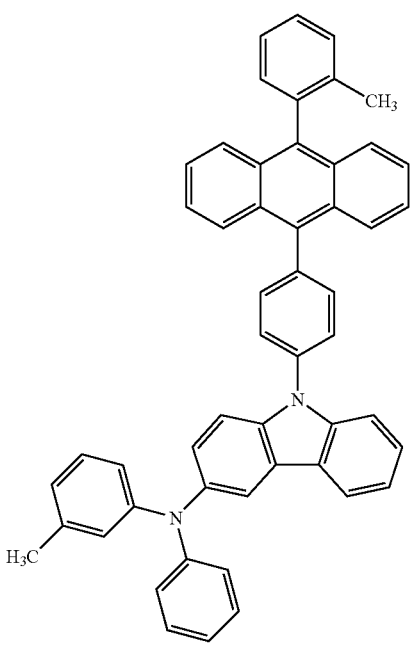
(398)
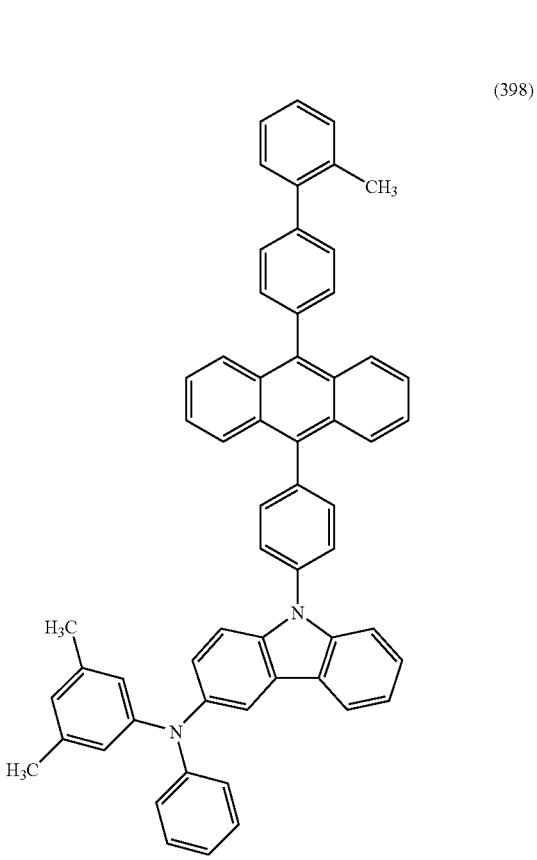

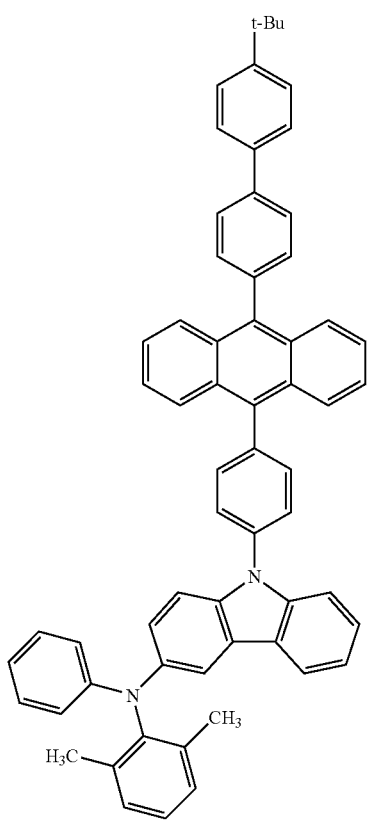

(399)

A variety of reactions can be applied as a synthesis method of an anthracene derivative contained in any of the compositions of this embodiment. For example, by synthesis reactions described below, the anthracene derivative contained in any of the compositions of this embodiment can be synthesized. Note that a synthesis method of the anthracene derivative contained in any of the compositions of this embodiment is not limited to the following synthesis method.

<Synthesis Method of Anthracene Derivative represented by General Formula (G33-1)>

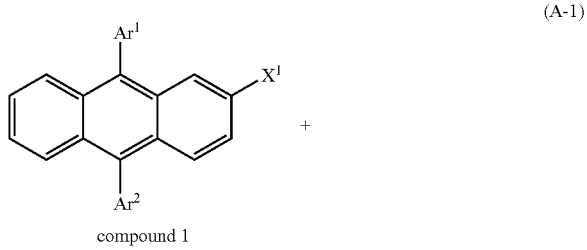

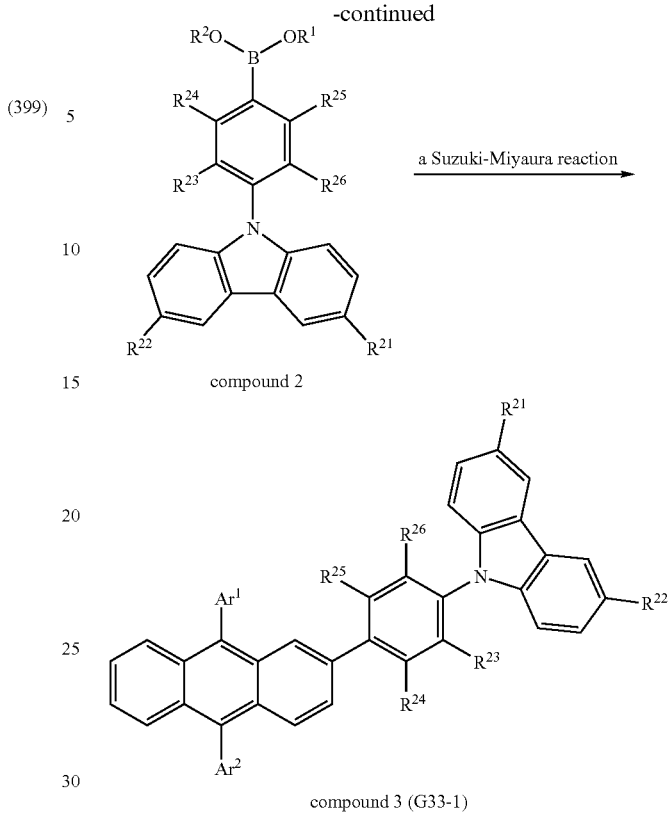

As illustrated in a synthesis scheme (A-1), an anthracene derivative (a compound 1) and a boronic acid or organoboron of a carbazole derivative (a compound 2) are coupled by a Suzuki-Miyaura reaction, whereby an anthracene derivative in which a carbazole skeleton is bonded to the 2-position (a compound 3) through a phenylene group, which is the object of the synthesis, can be obtained. In the synthesis scheme (A-1), $X^1$ represents halogen or a triflate group, $Ar^1$ and $Ar^2$ each represent a substituted or unsubstituted aryl group having 6 to 13 carbon atoms, $R^{21}$ and $R^{22}$ each represent hydrogen, an alkyl group having 1 to 4 carbon atoms, or a substituted or unsubstituted aryl group having 6 to 13 carbon atoms, and $R^{23}$ to $R^{26}$ each represent hydrogen, an alkyl group having 1 to 4 carbon atoms, or a substituted or unsubstituted phenyl group. In addition, in the case where $X^1$ is halogen, $X^1$ is preferably chlorine, bromine, or iodine.

Examples of the palladium catalyst that can be used in the synthesis scheme (A-1) include, but are not limited to, palladium(II) acetate and tetrakis(triphenylphosphine)palladium (0). Examples of a ligand in the palladium catalyst, which can be used in the synthesis scheme (A-1), include, but are not limited to, tri(ortho-tolyl)phosphine, triphenylphosphine, and tricyclohexylphosphine. Examples of a base that can be used in the synthesis scheme (A-1) include, but are not limited to, an organic base such as sodium tert-butoxide and an inorganic base such as potassium carbonate. In the synthesis scheme (A-1), as a solvent that can be used, a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; a mixed solvent of an ether such as ethylene glycol dimethyl ether and water; or the like can be given. However, solvents that can be used are not limited to these. Use of a mixed solvent of toluene and water or a mixed solvent of toluene, ethanol, and water is more preferable.

As described above, the anthracene derivative contained in any of the compositions of this embodiment can be synthesized.

An alkyl group is highly effective in inhibiting crystallization, and thus, introduction of an alkyl group to a structure has the effect of inhibiting the crystallization. However, with regard to anthracene derivatives contained in the compositions of the present invention, each anthracene derivative can be dissolved in a solvent even if the structure has no alkyl group, and a film with a uniform film quality can be formed by a wet process. The structure having no alkyl group is more preferably used for electronic devices or the like because carriers are easily transported in such a structure.

Since the anthracene derivative that has the above-described structure and is contained in any of the compositions of the present invention has a wide band gap, blue light emission with high color purity can be obtained. Further, the anthracene derivative contained in any of the compositions of the present invention has high electrochemical stability and thermal stability.

The anthracene derivative contained in any of the compositions of the present invention can not only be used individually for the layer containing a light-emitting substance but also be used as a host. Light emission from a dopant that serves as a light-emitting substance can be obtained with a structure in which the dopant that serves as a light-emitting substance is dispersed in the composition of the present invention which has an anthracene derivative and a solvent. Use of the anthracene derivative as a host makes it possible to obtain blue light emission with high color purity.

The anthracene derivative contained in any of the compositions of the present invention can also be used for the functional layers of a light-emitting element. For example, the anthracene derivative can be used as a hole-transporting layer or an electron-transporting layer, which is a carrier-transporting layer, or a hole-injecting layer or an electron-injecting layer, which is a carrier-injecting layer. Thus, the functional layers of the light-emitting element can be formed by a wet process with the use of any of the compositions of the present invention which has an anthracene derivative and a solvent.

A thin film formed by a wet process with the use of any of the compositions of the present invention which has an anthracene derivative and a solvent is used for a light-emitting element, whereby the light-emitting element can be made to be highly reliable.

In the above-described compositions, a variety of solvents can be used as the solvent. For example, the anthracene derivatives can be dissolved in solvents that have aromatic rings (e.g., a benzene ring), such as toluene, xylene, methoxybenzene (anisole), dodecylbenzene, or a mixed solvent of dodecylbenzene and tetralin. The above-described anthracene derivatives can also be dissolved in organic solvents that do not have aromatic rings, such as dimethylsulfoxide (abbr.; DMSO), dimethylformamide (abbr.; DMF), or chloroform.

Alternatively, as other solvents, ketone solvents such as cyclohexanone, ether solvents such as tetrahydrofuran and dioxane, and the like can be given.

Further, each composition described in this embodiment may also contain any other organic material. For the organic material, any of aromatic compounds or heteroaromatic compounds which are solid at room temperature can be used. For the organic material, any of low molecular weight compounds or macromolecular compounds can be used. When a low molecular weight compound is used, it is preferable to use a low molecular weight compound (which may also be referred to as an intermediate molecular weight compound) having a substituent that is capable of increasing the solubility in a solvent.

The composition may further include a binder in order to improve a film quality of a film that is to be formed. For the binder, a macromolecular compound that is electrically inactive is preferably used. Specifically, polymethylmethacrylate (abbr.: PMMA), polyimide, or the like can be used.

A thin film can be formed by a wet process with the use of a liquid composition of the present invention in which an anthracene derivative is dissolved in a solvent. In the wet process, a material for forming the thin film is dissolved in the solvent, and the liquid composition is attached to a region where the film is to be formed, the solvent is removed, and the resulting material is solidified, whereby the thin film is formed.

For the wet process, any of the following methods can be employed: a spin coating method, a roll coat method, a spray method, a casting method, a dipping method, a droplet discharging (ejection) method (an ink-jet method), a dispenser method, a variety of printing methods (a method by which a thin film can be formed in a desired pattern, such as screen (stencil) printing, offset (planographic) printing, letterpress printing, or gravure (intaglio) printing, or the like. Note that without limitation to the above methods, the compositions of the present invention can be used as long as a method in which a liquid composition is used is employed.

In a wet process, compared with a dry process such as an evaporation method or a sputtering method, a material is not scattered in a chamber, and therefore, material use efficiency is higher. Furthermore, facilities needed for a vacuum apparatus and the like can be reduced because the formation can be performed at atmospheric pressure. Further still, since the size of a substrate that is to be processed is not limited by the size of a vacuum chamber, it is possible to respond to use of a larger substrate to increase a processing area, whereby low cost and improvement of productivity can be achieved. A wet process requires only heat treatment at about temperature at which a solvent of a composition can be removed, and thus is a so-called low temperature process. Therefore, it is possible to use even substrates and materials that can be degraded or deteriorated by heat treatment at high temperature.

Furthermore, since a liquid composition having fluidity is used for the formation, materials can be easily mixed. For example, an emission color that is to be obtained can be controlled by addition of a plurality of dopants to a composition. Further still, good coverage with respect to a region where the thin film is to be formed can also be achieved.

The thin film can be selectively formed by a droplet discharging method in which a composition can be discharged into a desired pattern, a printing method in which a composition can be transferred or drawn into a desired pattern, or the like. Therefore, a loss of a material is further prevented, and a material can be efficiently used, resulting in a reduction in manufacturing cost. Furthermore, such methods do not require shaping of the thin film by a photolithography process, and thus have the effects of simplifying the process and improving the productivity.

A thin film formed by a wet process with the use of any of the compositions of this embodiment, in which an anthracene derivative is dissolved in a solvent, can be made to have a favorable film quality without defects or the like. Thus, with the use of such a composition and a thin film, a highly reliable light-emitting element (device) can be manufactured.

In this embodiment, since a wet process is employed for manufacture of a thin film and a light-emitting element, high material use efficiency and a reduction in expensive facilities such as a large vacuum apparatus can be achieved, resulting in low cost and high productivity. Thus, by use of the present invention, a light-emitting device and an electronic device that are highly reliable can be manufactured at low cost with high productivity.

(Embodiment 2)

In this embodiment, compositions of the present invention and another example of a method of forming a thin film with the use of the composition are described.

An anthracene derivative contained in any of the compositions of this embodiment has a feature that it has one anthracene structure and one carbazolyl group, and the carbazolyl group is directly bonded to the anthrancence structure.

An anthracene derivative contained in any of the compositions of this embodiment, as described above, is specifically represented by any of the following general formulae (G33-1), (G31-2), (G31-3), and (G32-1).

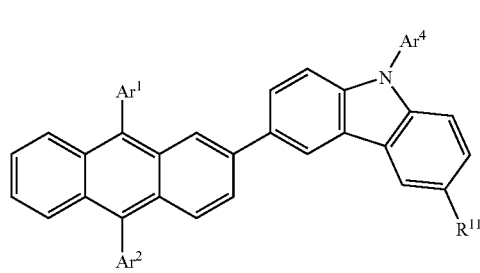
(G31-1)

In the formula, $Ar^1$ and $Ar^2$ each represent a substituted or unsubstituted aryl group having 6 to 13 carbon atoms, $Ar^4$ represents a substituted or unsubstituted aryl group having 6 to 13 carbon atoms, and $R^{11}$ represents hydrogen, an alkyl group having 1 to 4 carbon atoms, or a substituted or unsubstituted aryl group having 6 to 13 carbon atoms.

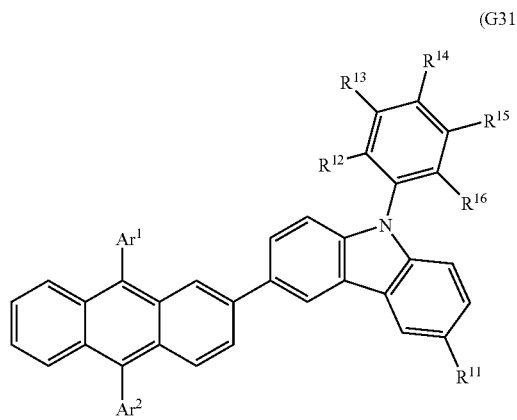
(G31-2)

In the formula, $Ar^1$ and $Ar^2$ each represent a substituted or unsubstituted aryl group having 6 to 13 carbon atoms, $R^{11}$ represents hydrogen, an alkyl group having 1 to 4 carbon atoms, or a substituted or unsubstituted aryl group having 6 to 13 carbon atoms, and $R^{12}$ to $R^{16}$ each represent hydrogen, an alkyl group having 1 to 4 carbon atoms, or a substituted or unsubstituted aryl group having 6 to 10 carbon atoms.

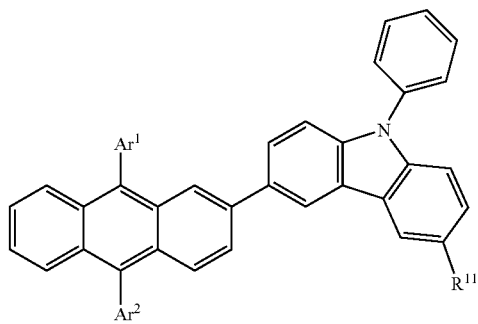
(G31-3)

In the formula, $Ar^1$ and $Ar^2$ each represent a substituted or unsubstituted aryl group having 6 to 13 carbon atoms, and $R^{31}$ represents hydrogen, an alkyl group having 1 to 4 carbon atoms, or a substituted or unsubstituted aryl group having 6 to 13 carbon atoms.

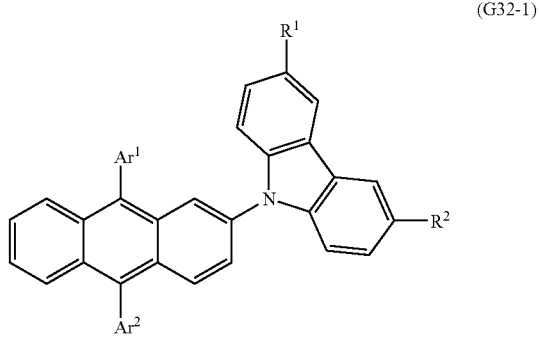
(G32-1)

In the formula, $Ar^1$ and $Ar^2$ each represent a substituted or unsubstituted aryl group having 6 to 13 carbon atoms, $R^1$ and $R^2$ each represent hydrogen, an alkyl group having 1 to 4 carbon atoms, or a substituted or unsubstituted aryl group having 6 to 13 carbon atoms.

In each of the general formulae (G31-1), (G31-2), (G31-3), and (G32-1), an aryl group having 6 to 13 carbon atoms may have a substituent. If the aryl group having 6 to 13 carbon atoms has a plurality of substituents, the substituents may be bonded to form a ring. Further, if a carbon atom has two substituents, the substituents may be bonded to each other to form a spiro ring. For example, there are substituents represented by structural formulae (11-1) to (11-16).

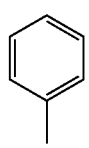
(11-1)

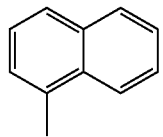
(11-2)

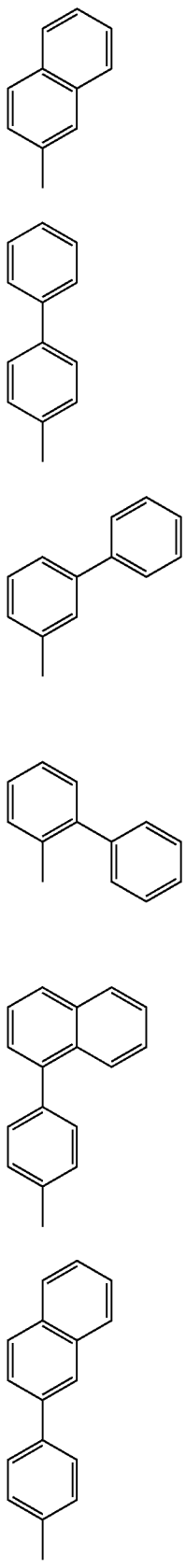
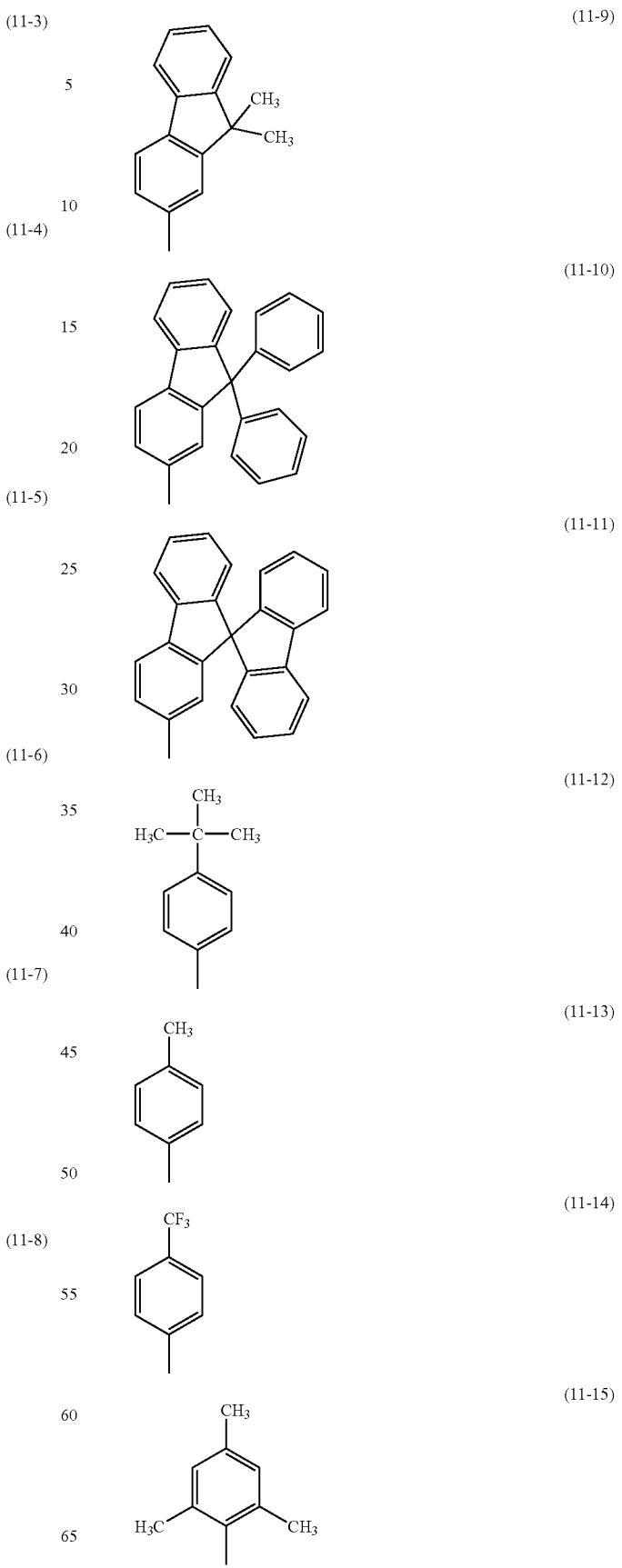

-continued (11-16)
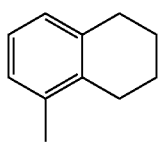

As the substituted or unsubstituted aryl group having 6 to 10 carbon atoms in the general formula (G31-2), there are substituents represented by structural formulae (13-1) to (13-8), for example.

(13-1)
(13-2)
(13-3)
(13-4)
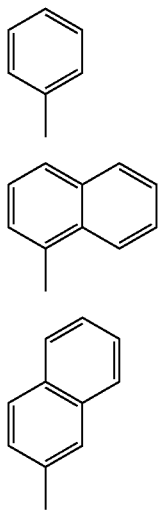

-continued (13-5)
(13-6)
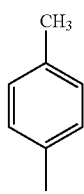

(13-7)
(13-8)
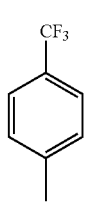
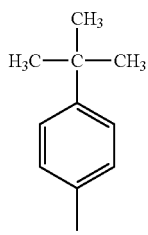

Further, in the anthracene derivative represented by any of the general formulae (G31-1), (G31-2), (G31-3), and (G32-1), $Ar^1$ and $Ar^2$ are preferably substituents having the same structure, for ease of synthesis and purification.

Specific examples of the anthracene derivatives represented by the general formulae (G31-1), (G31-2), and (G31-3) include, but not limited to, anthracene derivatives represented by structural formulae (101) to (142). Specific examples of the anthracene derivative represented by the general formula (G32-1) include, but not limited to, anthracene derivatives represented by structural formulae (1) to (37).

(101)
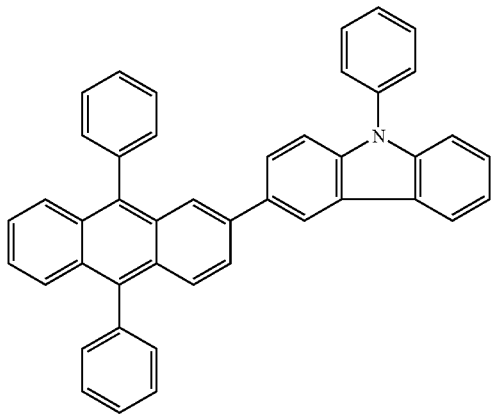

(102)
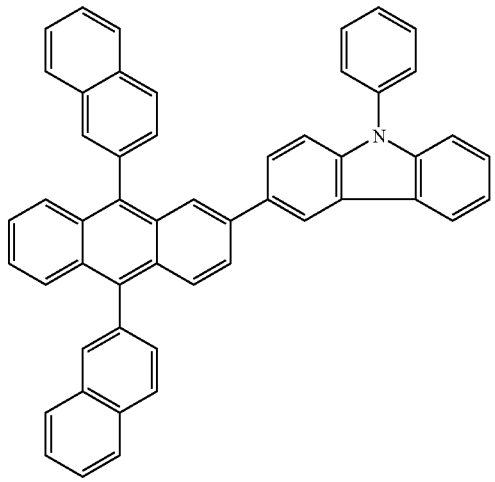

-continued
(103)
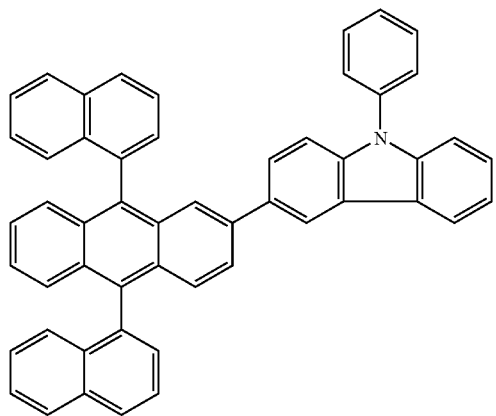
(104)
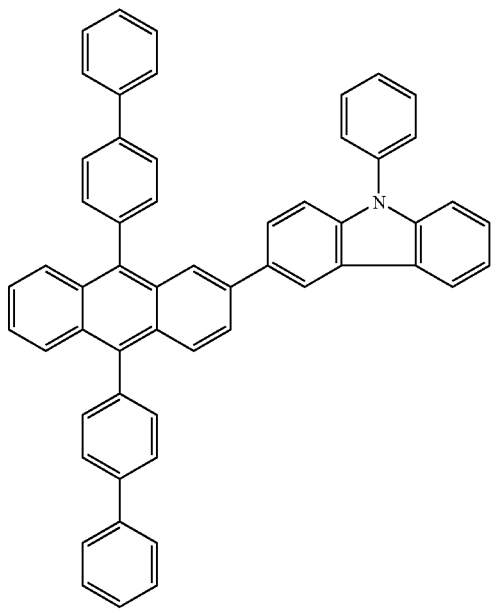
(105)
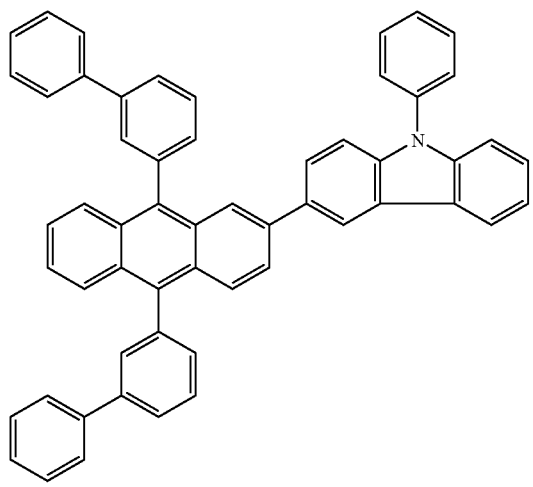
(106)
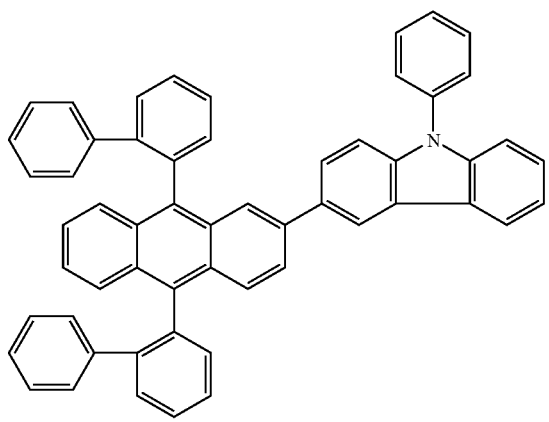
(107)
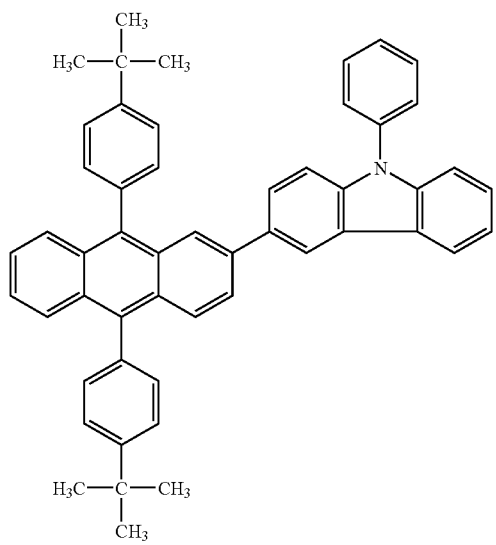
(108)
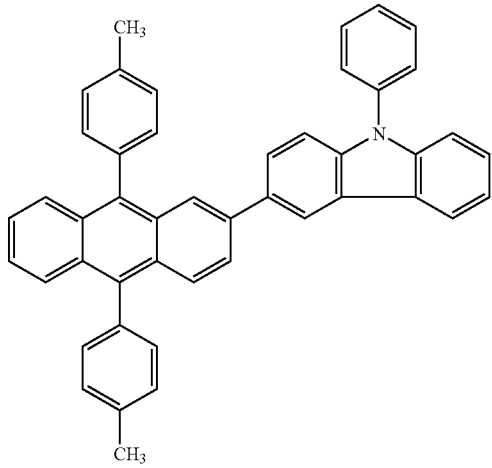

(109)
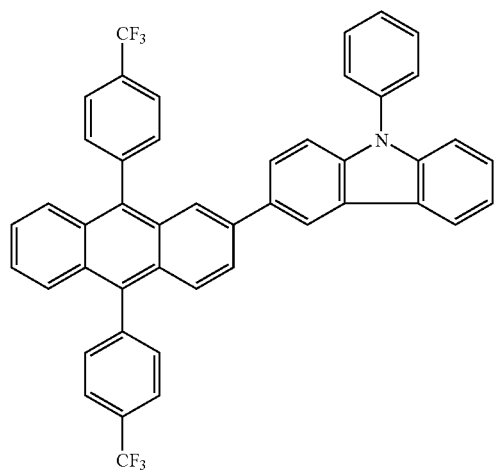
(110)
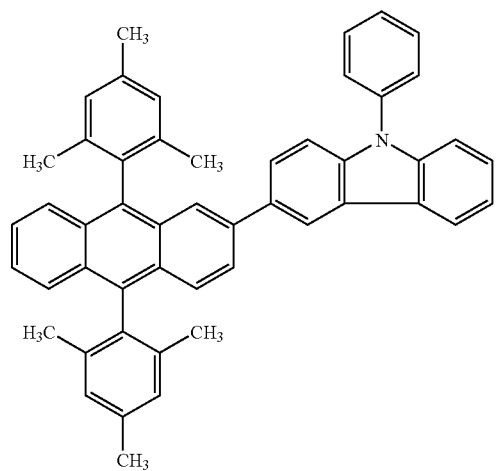
(111)
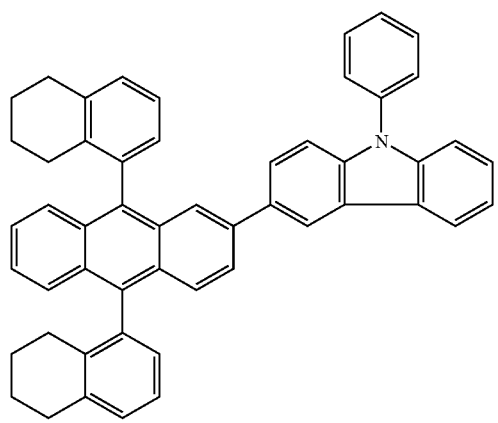
(112)
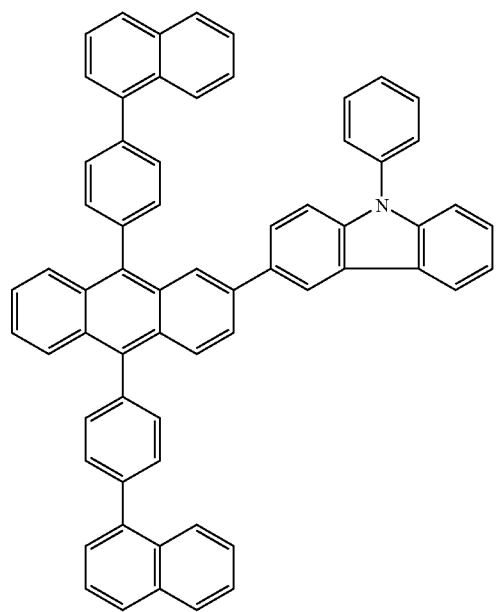

-continued
(113)
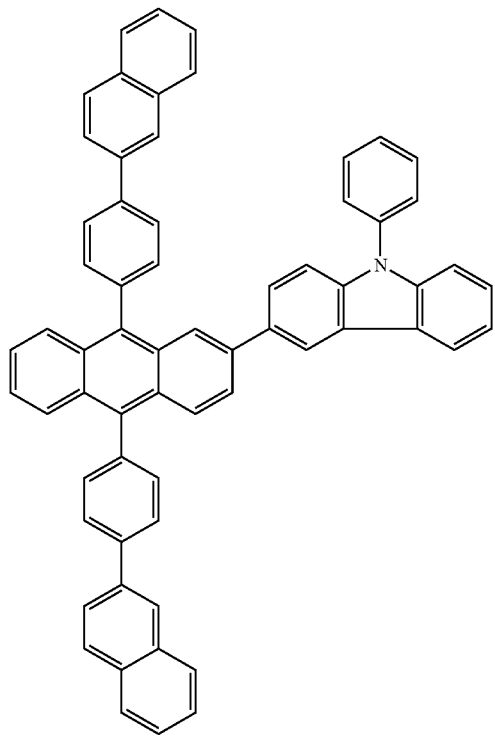
(114)
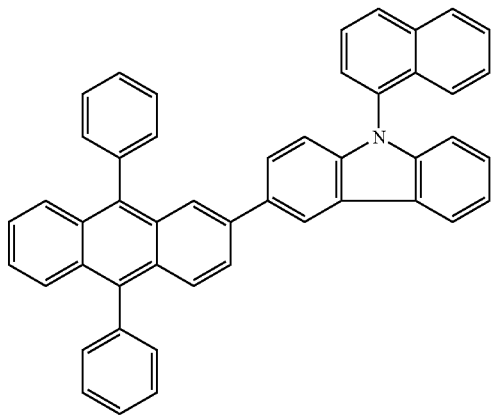
(115)
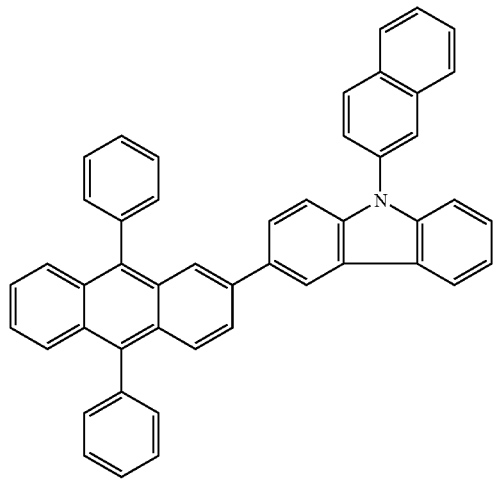
(116)
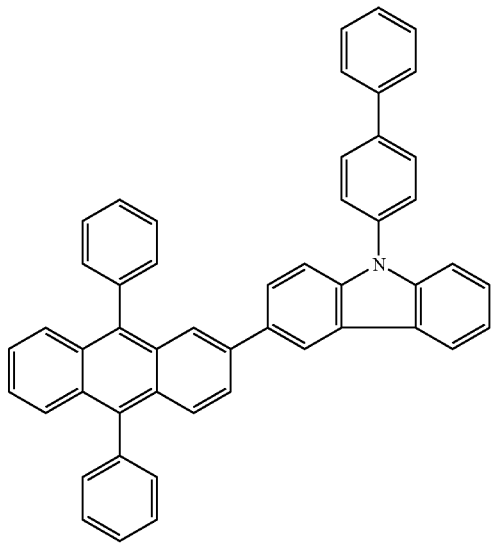

-continued
(117)
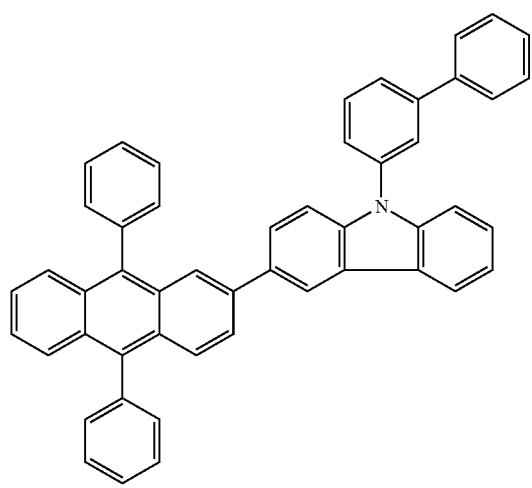
(118)
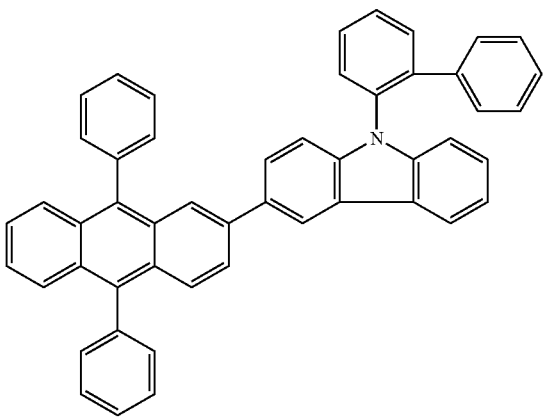
(119)
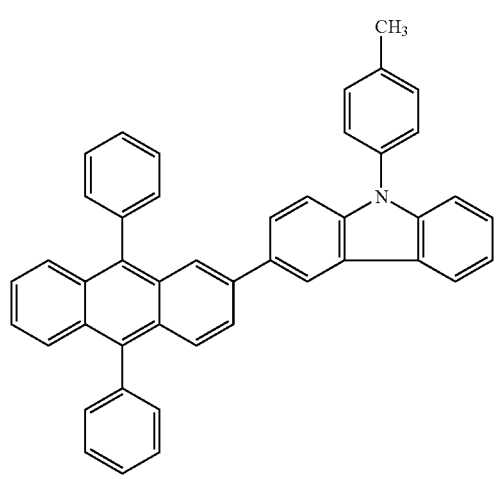
(120)
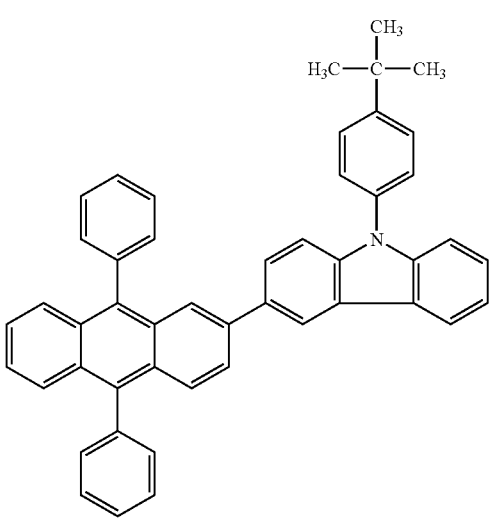
(121)
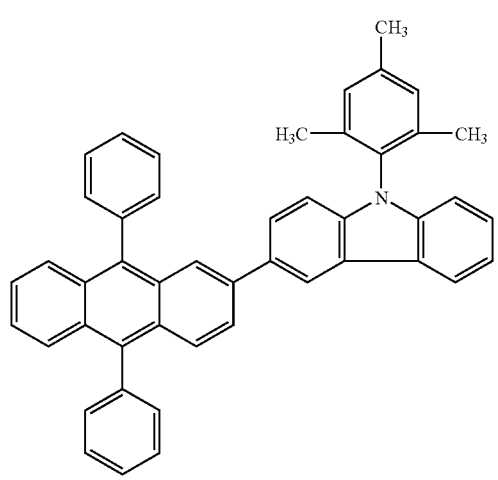
(122)
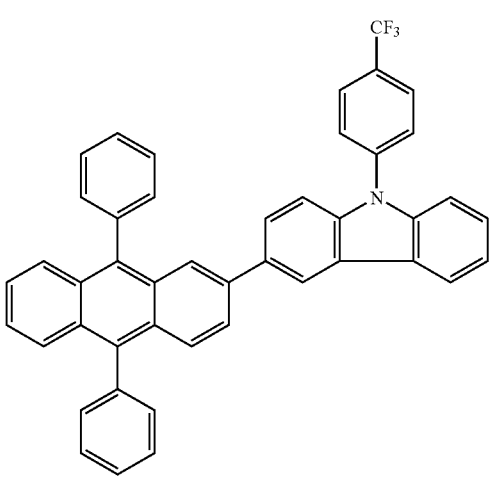

-continued
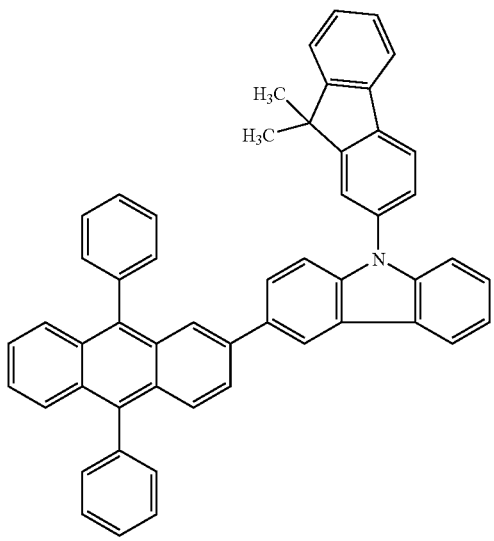
(123)
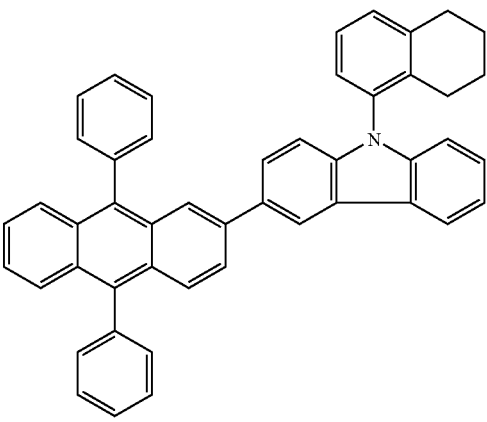
(124)
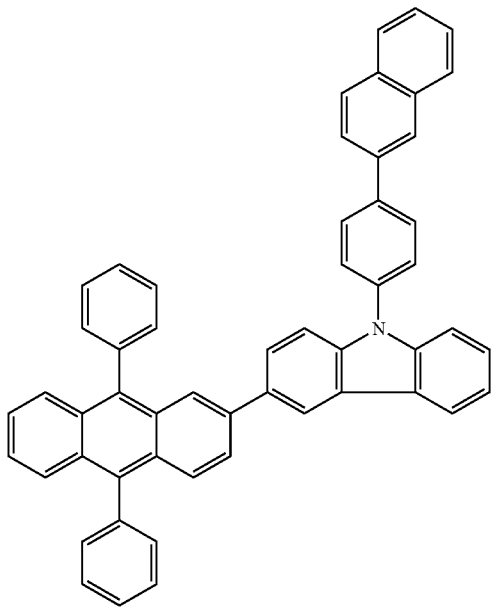
(125)
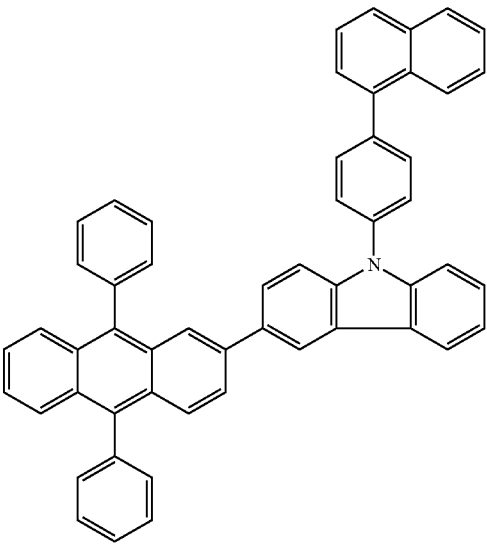
(126)
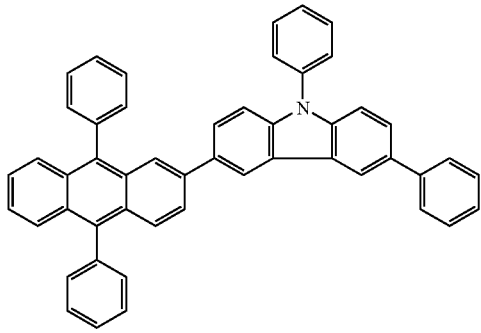
(127)
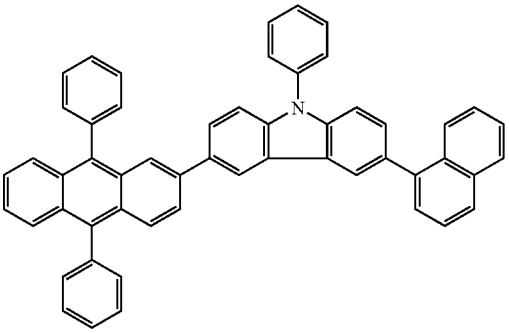
(128)

-continued
(129)
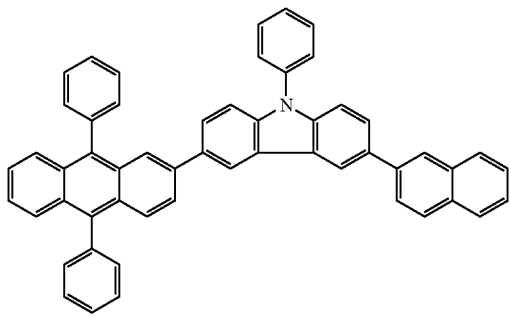
(130)
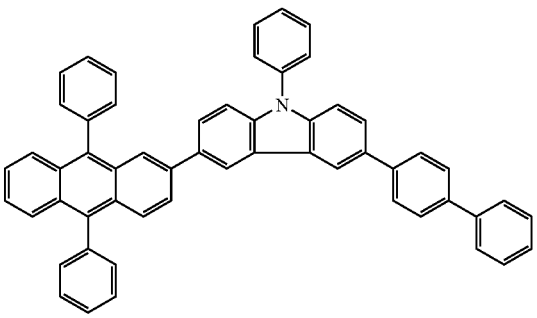
(131)
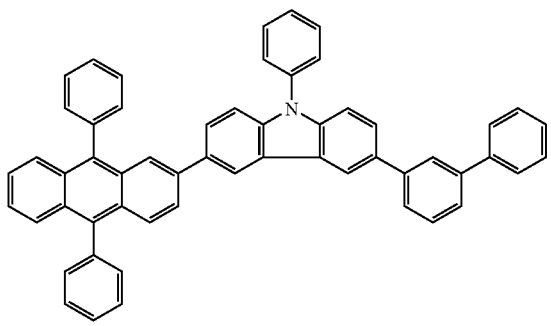
(132)
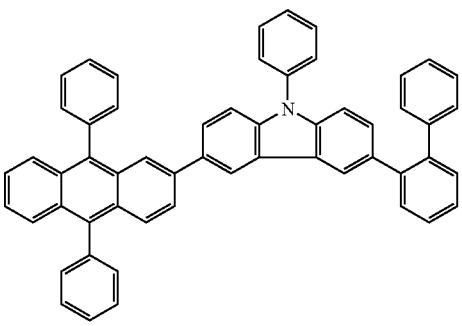
(133)
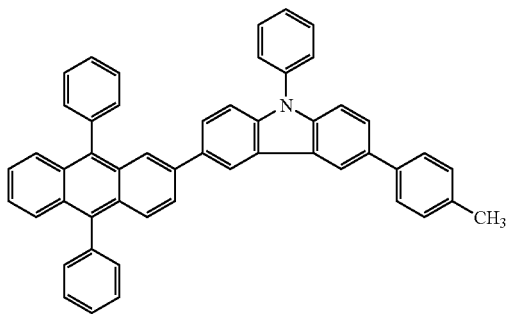
(134)
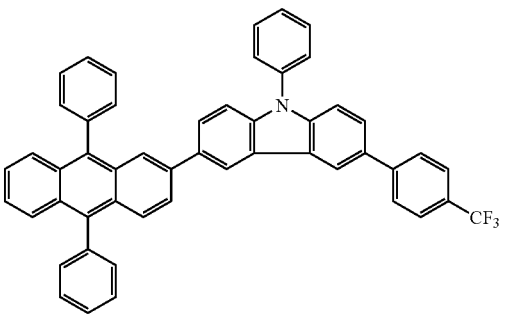
(135)
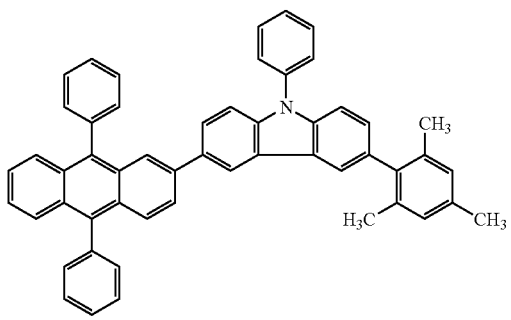
(136)
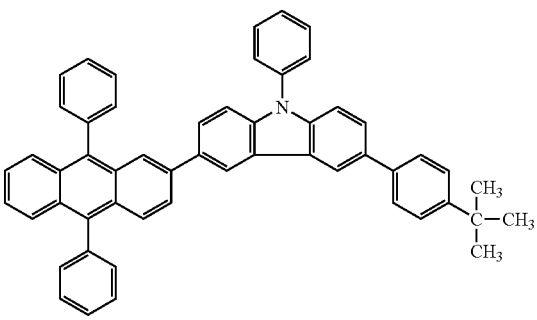

-continued
(137)
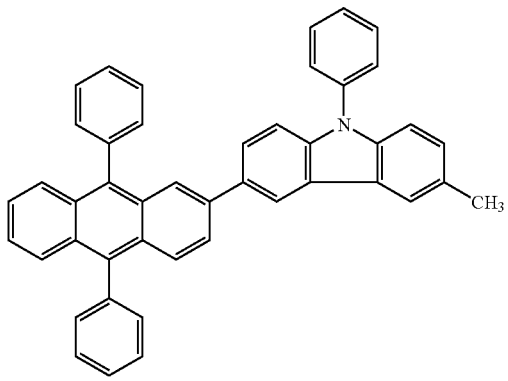
(138)
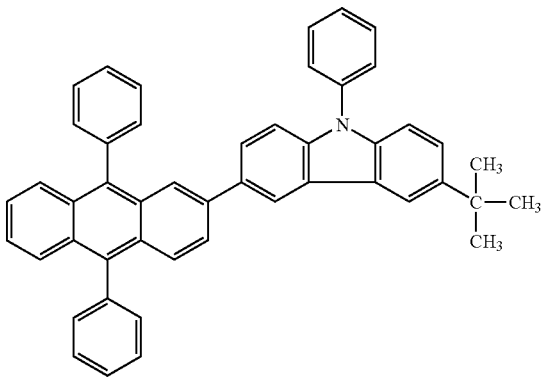
(139)
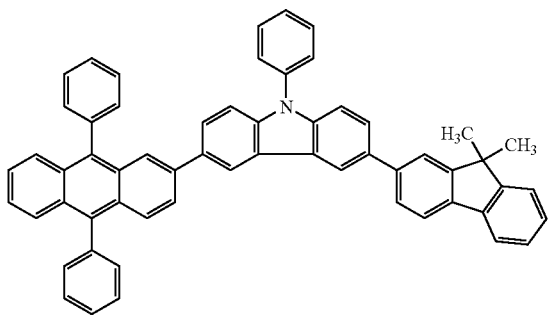
(140)
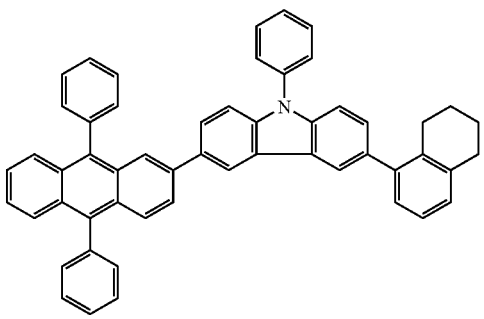
(141)
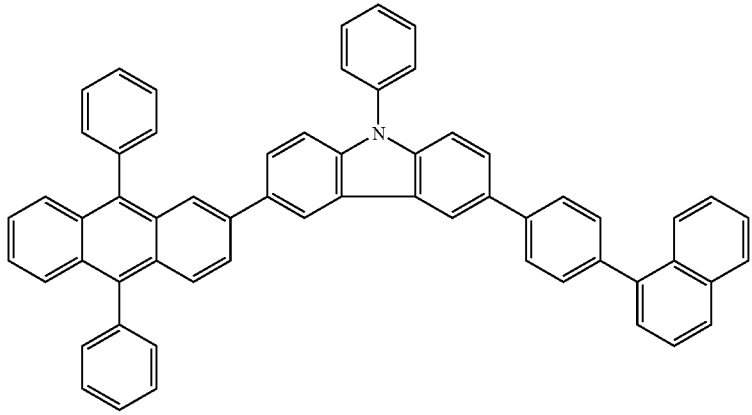
(142)
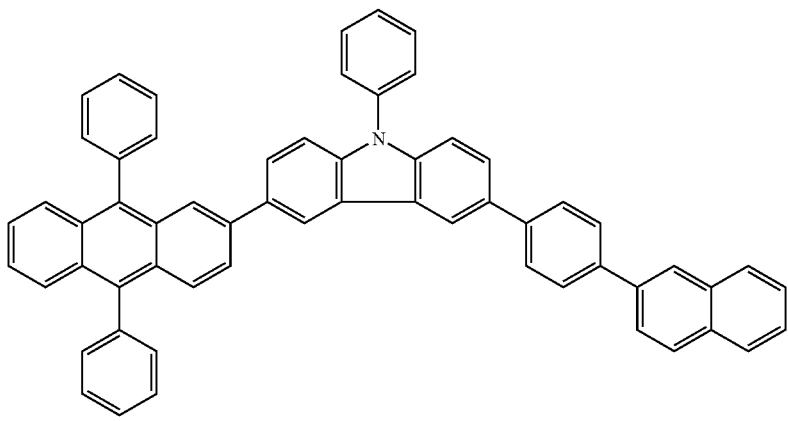

-continued
(1)
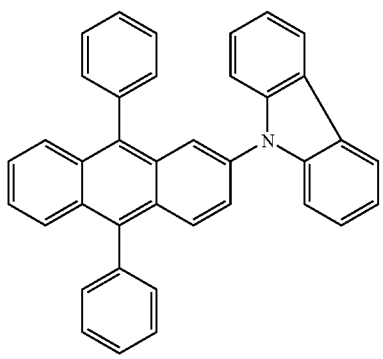
(2)
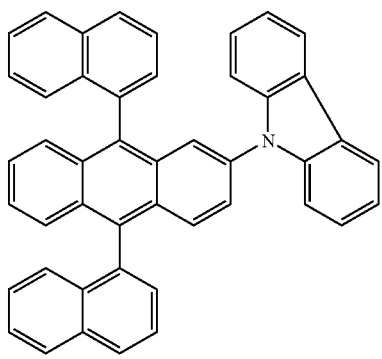
(3)
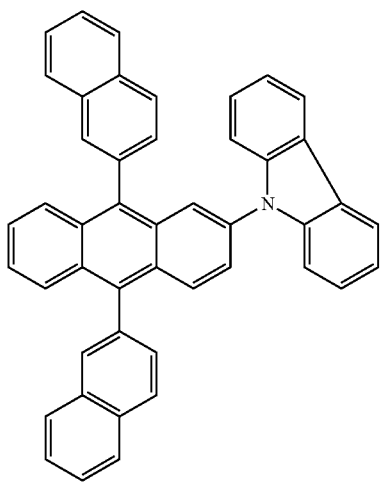
(4)
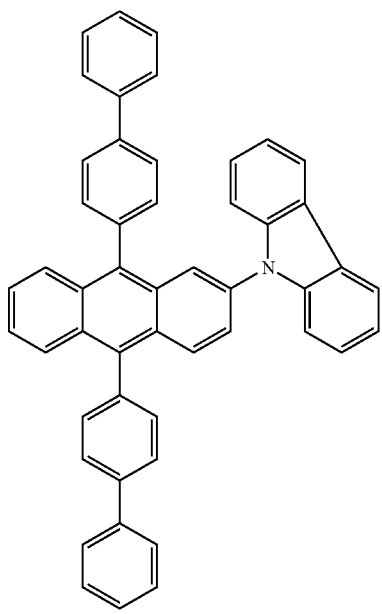
(5)
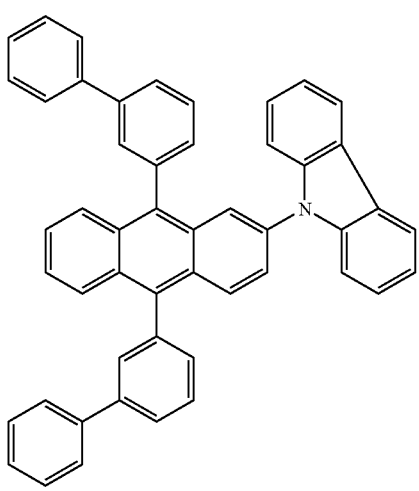
(6)
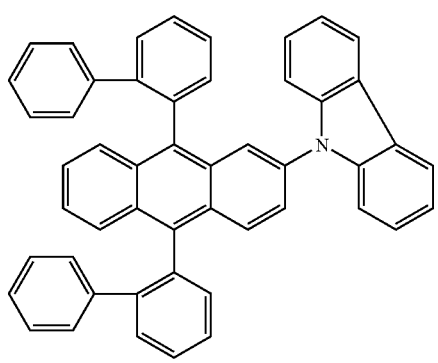

-continued
(7)
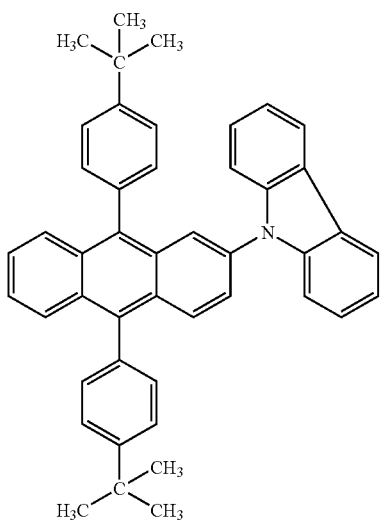
(8)
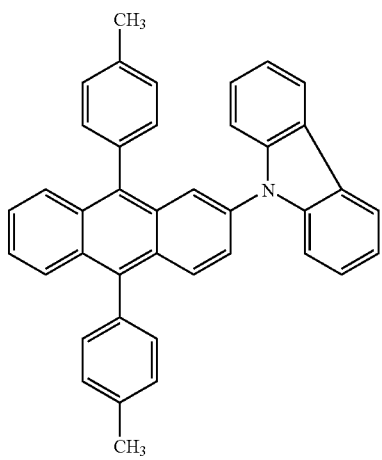
(9)
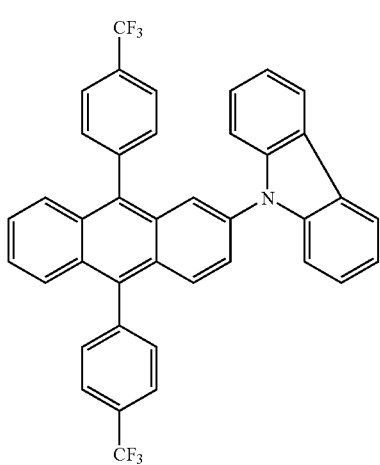
(10)
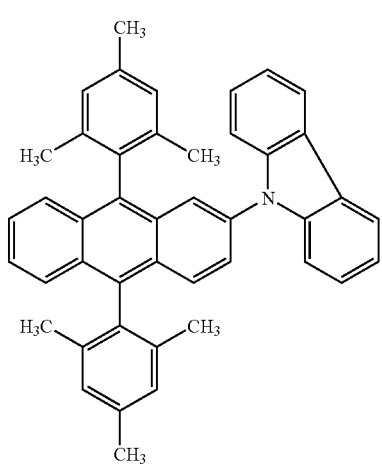
(11)
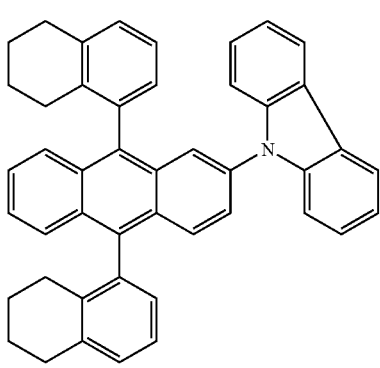
(12)
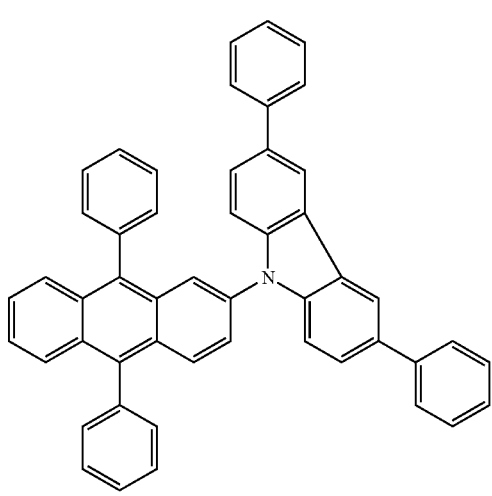

-continued
(13)
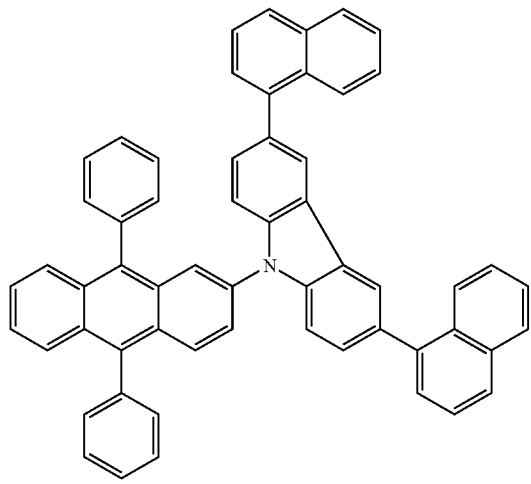
(14)
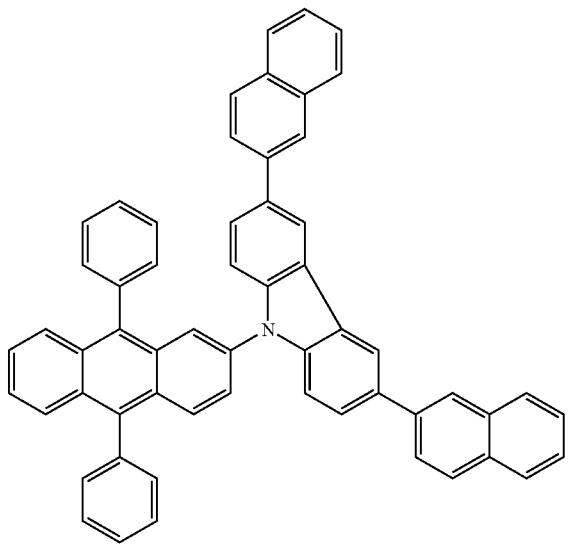
(15)
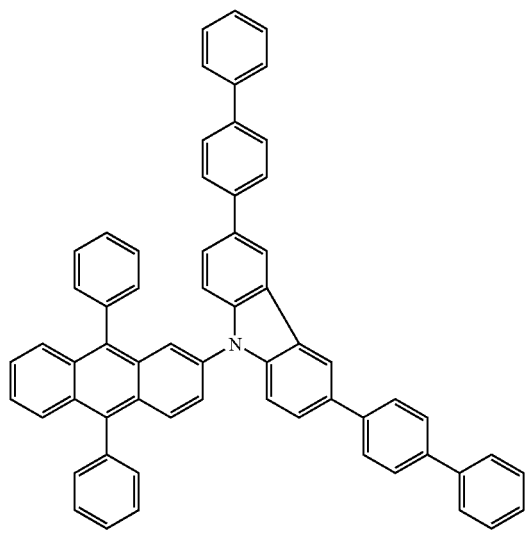
(16)
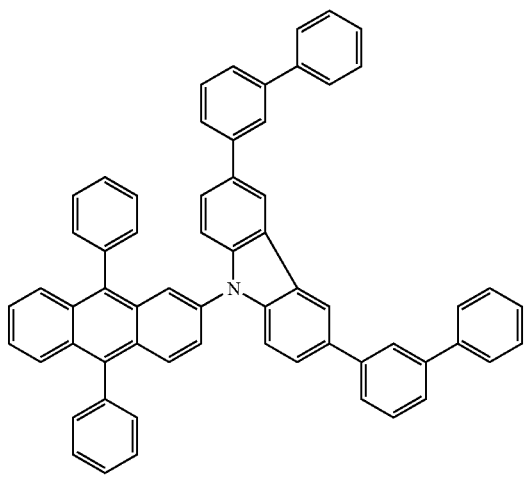
(17)
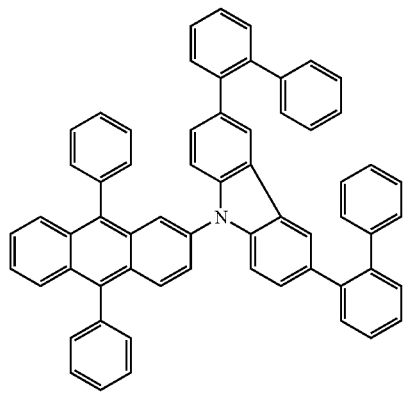
(18)
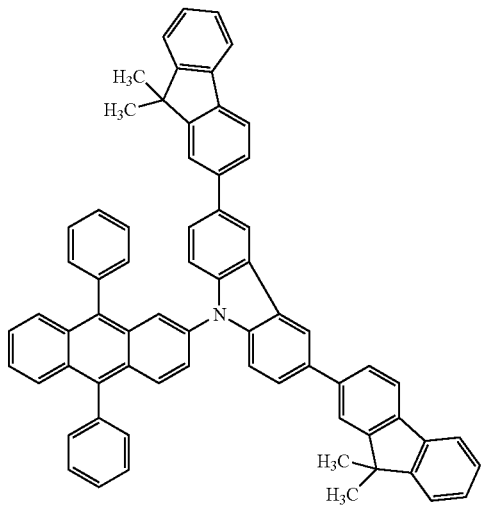

(19)
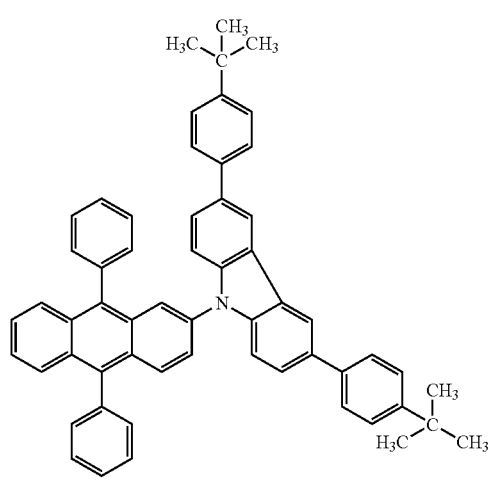
(20)
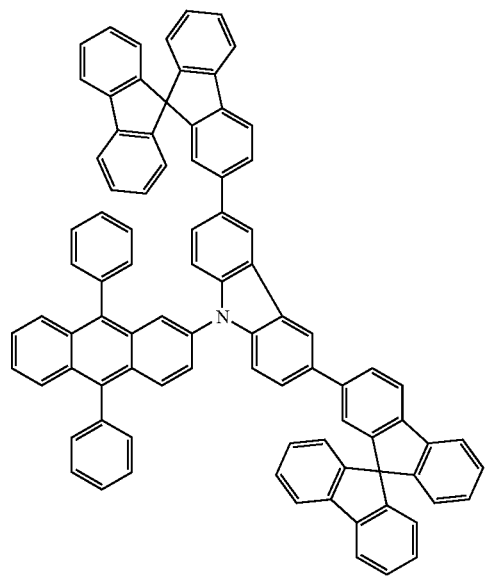
(21)
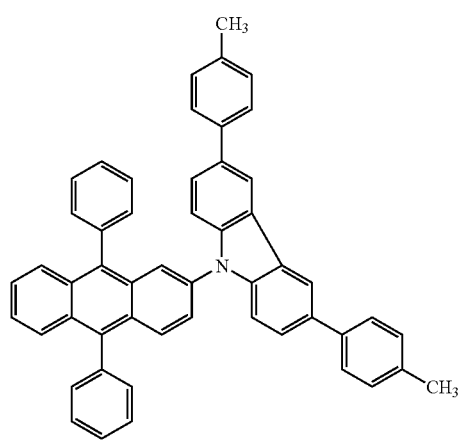
(22)
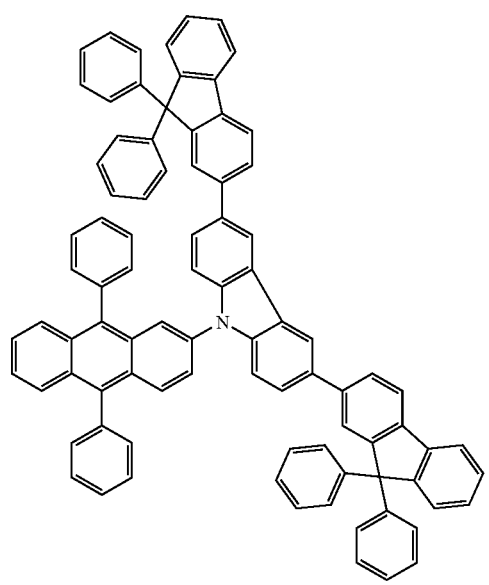

-continued
(23)
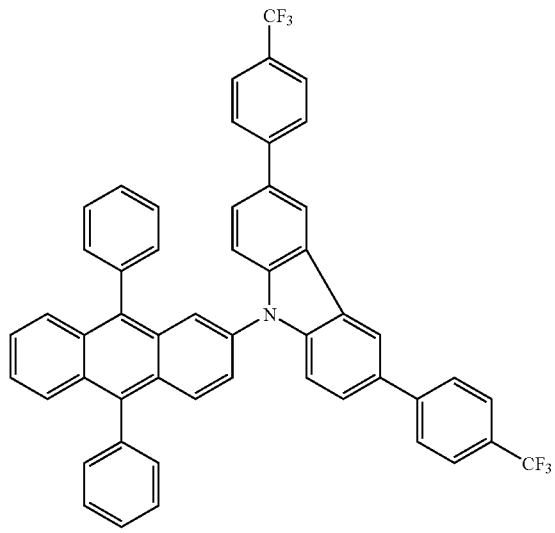
(24)
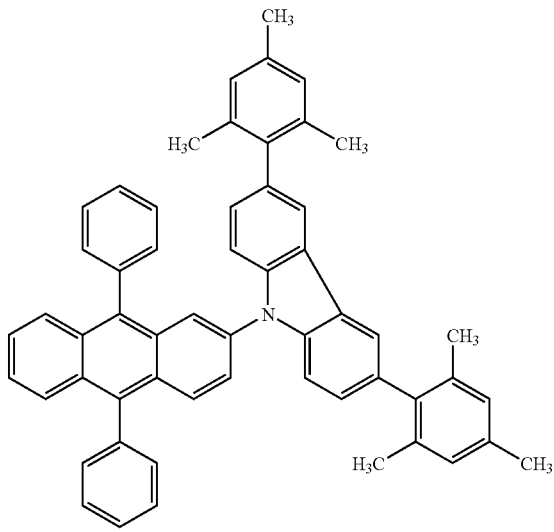
(25)
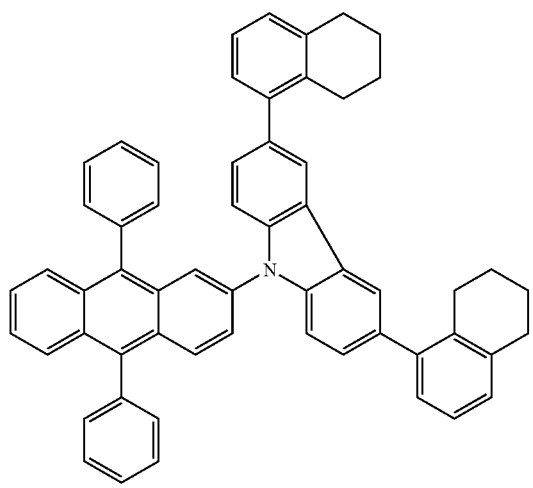
(26)
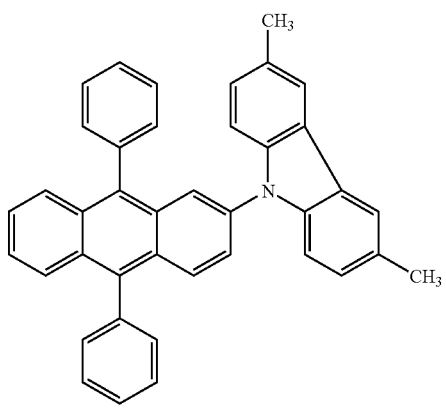
(27)
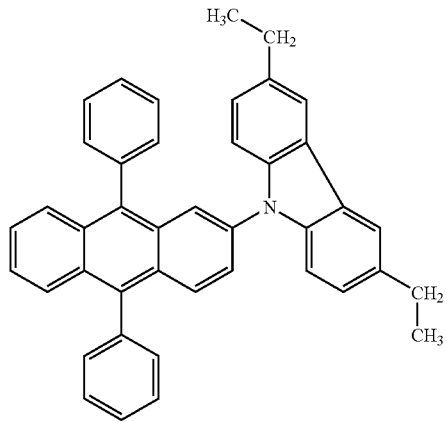
(28)
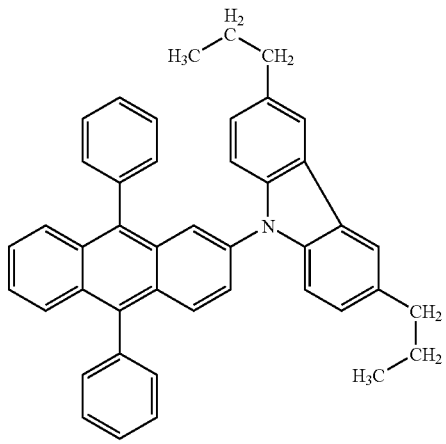

-continued
(29)
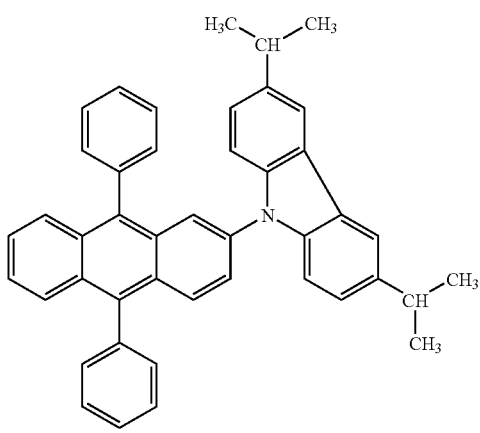
(30)
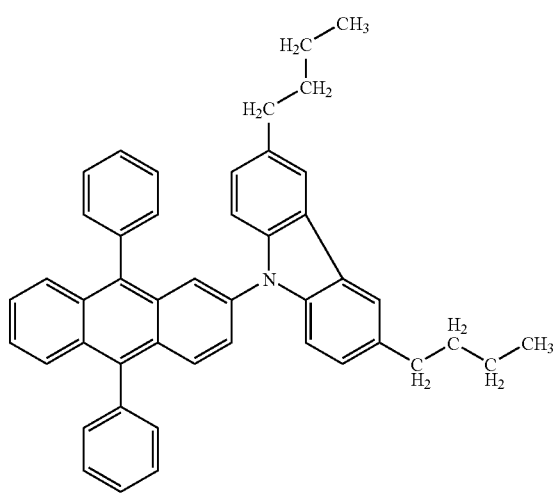
(31)
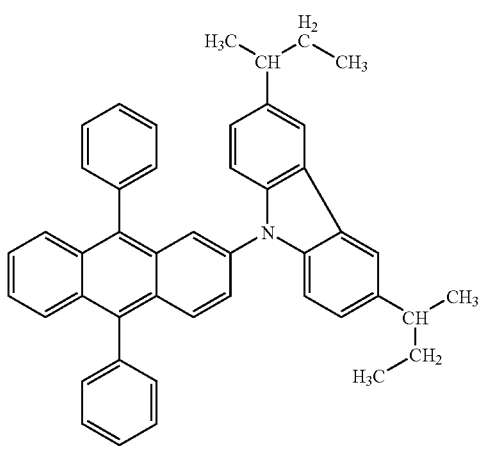
(32)
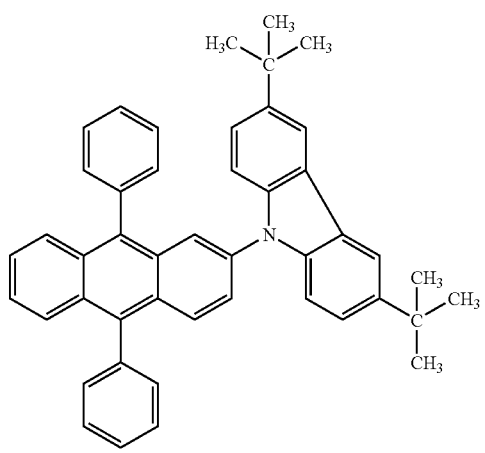

-continued
(33)
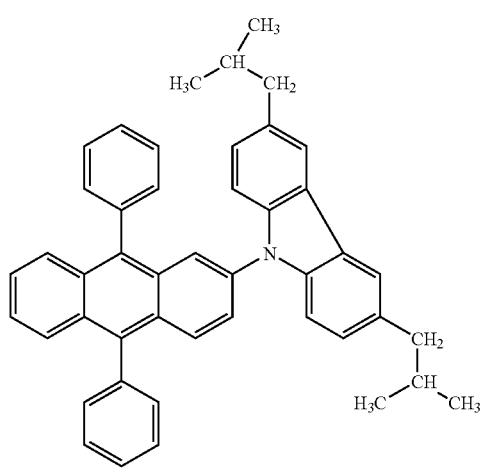
(34)
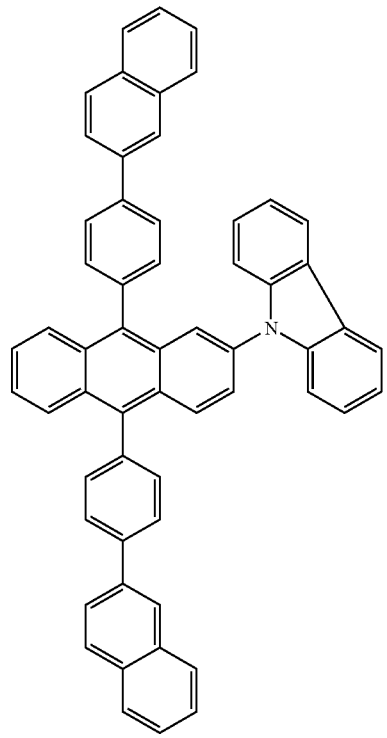
(35)
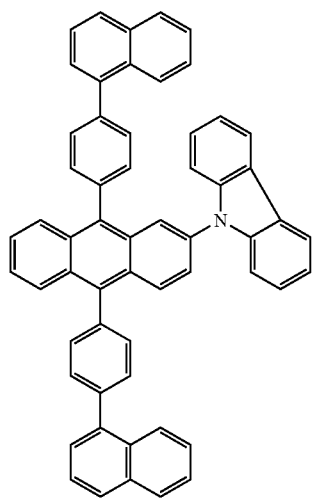
(36)
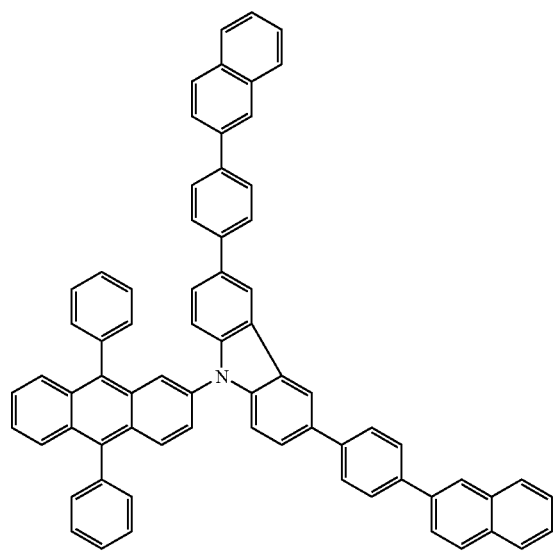

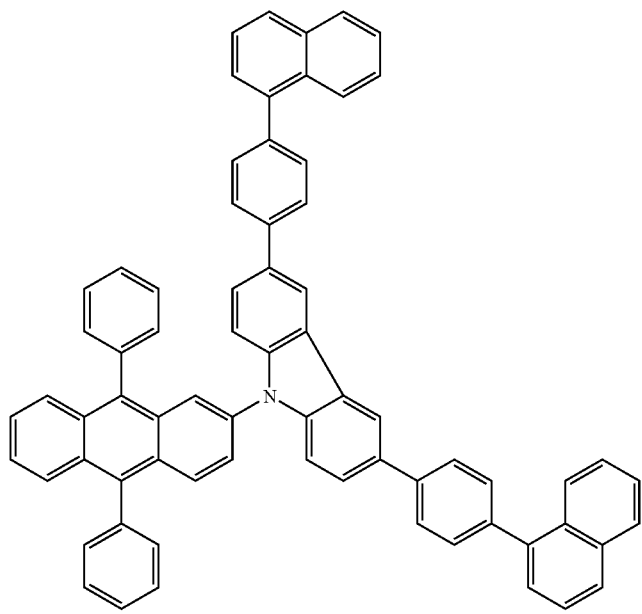

(37)

A variety of reactions can be applied as a synthesis method of an anthracene derivative contained in any of the compositions of this embodiment. For example, by synthesis reactions described below, the anthracene derivative contained in any of the compositions of this embodiment can be synthesized. Note that a synthesis method of the anthracene derivative contained in any of the compositions of this embodiment is not limited to the following synthesis method.

<Synthesis Method of Anthracene Derivative represented by General Formula (G31-1)>

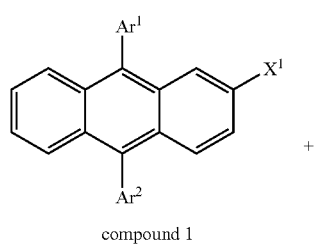

compound 1

(A-2)

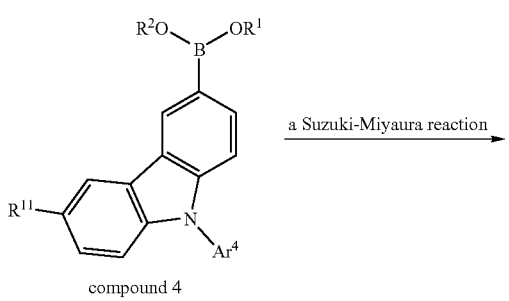

compound 4 a Suzuki-Miyaura reaction

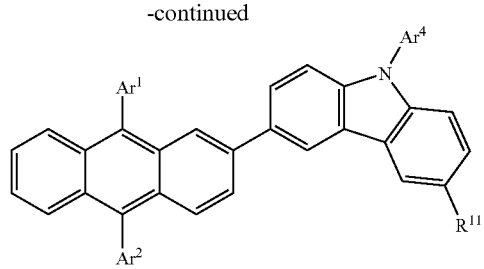

compound 5 (G31-1)

As illustrated in a synthesis scheme (A-2), an anthracene derivative (a compound 1) and a boronic acid or organoboron of a carbazole derivative (a compound 4) are coupled by a Suzuki-Miyaura reaction, whereby an anthracene derivative in which a carbazole skeleton is bonded to the 2-position (a compound 5), which is the object of the synthesis, can be obtained. In the synthesis scheme (A-2), $X^1$ represents halogen or a triflate group, $Ar^1$ and $Ar^2$ each represent a substituted or unsubstituted aryl group having 6 to 13 carbon atoms, $Ar^4$ represents a substituted or unsubstituted aryl group having 6 to 13 carbon atoms, and $R^{11}$ represents hydrogen, an alkyl group having 1 to 4 carbon atoms, or a substituted or unsubstituted aryl group having 6 to 13 carbon atoms. In addition, in the case where $X^1$ is halogen, $X^1$ is preferably chlorine, bromine, or iodine.

Examples of the palladium catalyst that can be used in the synthesis scheme (A-2) include, but are not limited to, palladium(II) acetate and tetrakis(triphenylphosphine)palladium (0). Examples of a ligand in the palladium catalyst which can be used in the synthesis scheme (A-1), include, but are not limited to, tri(ortho-tolyl)phosphine, triphenylphosphine, and tricyclohexylphosphine. Examples of a base that can be used in the synthesis scheme (A-2) include, but are not limited to, an organic base such as sodium tert-butoxide and an inorganic base such as potassium carbonate. In the synthesis scheme (A-1), as a solvent that can be used, a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; a mixed solvent of an ether such as ethylene glycol dimethyl ether and water; or the like can be given. However, solvents that can be used are not limited to these. Use of a mixed solvent of toluene and water or a mixed solvent of toluene, ethanol, and water is more preferable.

<Synthesis Method of Anthracene Derivative represented by General Formula (G32-1)>

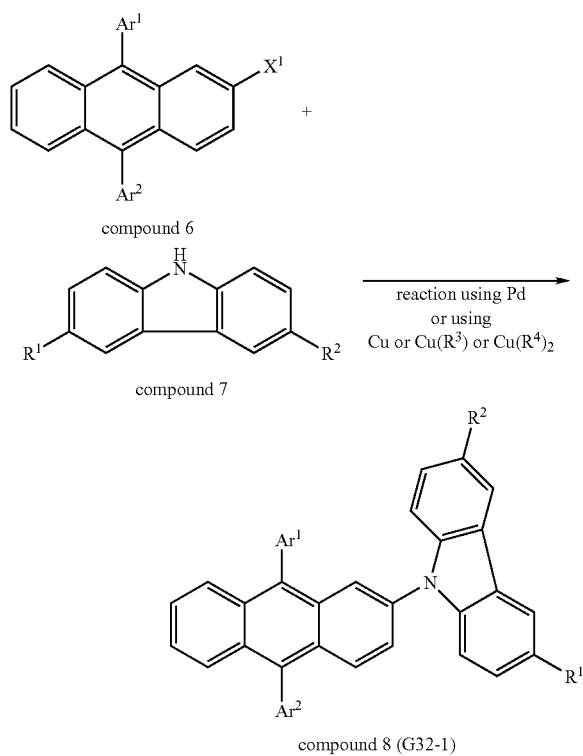

compound 8 (G32-1)

The anthracene derivative (a compound 8) of this embodiment which is represented by the general formula (G32-1) can be obtained in such a manner that 2-halogenated-9,10-diarylanthracene (a compound 6) and a 9H-carbazole derivative (a compound 7) are coupled in the presence of a base through a Hartwig-Buchwald reaction using a palladium catalyst or through an Ullmann reaction using copper or a copper compound.

In a synthesis scheme (A-3), $Ar^1$ and $Ar^2$ each represent a substituted or unsubstituted aryl group having 6 to 13 carbon atoms, $R^3$ and $R^2$ each represent hydrogen, an alkyl group having 1 to 4 carbon atoms, or a substituted or unsubstituted aryl group having 6 to 13 carbon atoms. $X^1$ represents a halogen group, specifically one of iodine, bromine, and chlorine.

In the case where a Buchwald-Hartwig reaction is performed, as the palladium catalyst which can be used in the synthesis scheme (A-3), bis(dibenzylideneacetone)palladium(0), palladium(II) acetate, and the like, can be given, but the pallarium catalyst which can be used is not limited thereto. Examples of a ligand of the palladium catalyst that can be used in the reaction formula include, but are not limited to, tri(tert-butyl)phosphine, tri(n-hexyl)phosphine, and tri(cyclohexyl)phosphine.

As a base which can be used in the synthesis scheme (A-3), an organic base such as sodium tert-butoxide, an inorganic base such as potassium carbonate, and the like can be given, but the base which can be used is not limited thereto.

As a solvent which can be used in the synthesis scheme (A-3), toluene, xylene, benzene, tetrahydrofuran, and the like can be given, but the solvent which can be used is not limited thereto.

The case in which an Ullmann reaction is performed in the synthesis scheme (A-3) is described. In the synthetic scheme (A-3), $R^3$ and $R^4$ each represent halogen, an acetyl group, or the like, and as halogen, chlorine, bromine, or iodine can be used. Further, copper(I) iodide when $R^3$ is iodine or copper(II) acetate when $R^4$ is an acetyl group is preferable. The copper compound used for the reaction is not limited thereto. Copper can be used instead of the copper compound.

As a base that can be used in the synthetic scheme (A-3), an inorganic base such as potassium carbonate or the like can be given, but the base that can be used is not limited thereto. As a solvent which can be used in the synthetic scheme (A-3), 1,3-dimethyl-3,4,5,6-tetrahydro-2(1H)pyrimidinone (DMPU), toluene, xylene, benzene, and the like can be given, but the solvent which can be used is not limited thereto. DMPU, xylene, or toluene which has a high boiling point is preferably used because, by an Ullmann reaction, an object can be obtained in a shorter time and at a higher yield when the reaction temperature is greater than or equal to 100° C. In particular, DMPU is more preferable because the reaction temperature is more preferably greater than or equal to 150° C. Alternatively, a solvent may be omitted in the Ullmann reaction; in this case, the reaction temperature is preferably higher than the melting point of a substrate.

In the aforementioned manner, the anthracene derivative contained in any of the compositions of the present invention can be synthesized.

An alkyl group is highly effective in inhibiting crystallization, and thus, introduction of an alkyl group to a structure has the effect of inhibiting the crystallization. However, with regard to anthracene derivatives contained in the compositions of the present invention, each anthracene derivative can be dissolved in a solvent even if the structure has no alkyl group, and a film with a uniform film quality can be formed by a wet process. The structure having no alkyl group is more preferably used for electronic devices or the like because carriers are easily transported in such a structure.

Since the anthracene derivative that has the above-described structure and is contained in any of the compositions of the present invention has a wide band gap, blue light emission with high color purity can be obtained. Furthermore, the anthracene derivative contained in any of the compositions of the present invention has high electrochemical stability and thermal stability.

The anthracene derivative contained in any of the compositions of the present invention can not only be used individually for the layer containing a light-emitting substance but also be used as a host. Light emission from a dopant that serves as a light-emitting substance can be obtained with a structure in which the dopant that serves as a light-emitting substance is dispersed in the composition of the present invention which has an anthracene derivative and a solvent. Use of the anthracene derivative as a host makes it possible to obtain blue light emission with high color purity.

The anthracene derivative contained in any of the compositions of the present invention can also be used for the functional layers of a light-emitting element. For example, the anthracene derivative can be used as a hole-transporting layer or an electron-transporting layer, which is a carrier-transporting layer, or a hole-injecting layer or an electron-injecting layer, which is a carrier-injecting layer. Thus, the functional layers of the light-emitting element can be formed by a wet process with the use of any of the compositions of the present invention which has an anthracene derivative and a solvent.

A thin film formed by a wet process with the use of any of the compositions of the present invention which has an anthracene derivative and a solvent is used for a light-emitting element, whereby the light-emitting element can be made to be highly reliable.

In the above-described compositions, a variety of solvents can be used as the solvent. For example, the anthracene derivatives can be dissolved in solvents that have aromatic rings (e.g., a benzene ring), such as toluene, xylene, methoxybenzene (anisole), dodecylbenzene, or a mixed solvent of dodecylbenzene and tetralin. The above-described anthracene derivatives can also be dissolved in organic solvents that do not have aromatic rings, such as dimethylsulfoxide (DMSO), dimethylformamide (DMF), or chloroform.

As other solvents, ketone solvents such as acetone, methyl ethyl ketone, diethyl ketone, n-propyl methyl ketone, and cyclohexanone; ester solvents such as ethyl acetate, n-propyl acetate, n-butyl acetate, ethyl propionate, γ-butyrolactone, and diethyl carbonate; ether solvents such as diethylether, tetrahydrofuran and dioxane; alcohol solvents such as ethanol, isopropanol, 2-methoxyethanol, and 2-ethoxyethanol, and the like can be given.

Further, each composition described in this embodiment may also contain any other organic material. For the organic material, any of aromatic compounds or heteroaromatic compounds which are solid at room temperature can be used. For the organic material, any of low molecular weight compounds or macromolecular compounds can be used. When a low molecular compound is used, a low molecular compound (which may be referred to as an intermediate molecular weight compound) having a substituent that is capable of increasing the solubility in a solvent is preferably used.

The composition may further include a binder in order to improve a film quality of a film that is to be formed. For the binder, use of a macromolecular compound that is electrically inactive is preferably used. Specifically, polymethylmethacrylate (abbr. PMMA), polyimide, or the like can be used.

A thin film can be formed by a wet process with the use of a liquid composition of the present invention in which an anthracene derivative is dissolved in a solvent. In the wet process, a material for forming a thin film is dissolved in the solvent, and the liquid composition is attached to a region where the film is to be formed, the solvent is removed, and the resulting material is solidified, whereby the thin film is formed.

For the wet process, any of the following methods can be employed: a spin coating method, a roll coat method, a spray method, a casting method, a dipping method, a droplet discharging (ejection) method (an inkjet method), a dispenser method, a variety of printing methods (a method by which a thin film can be formed in a desired pattern, such as screen (stencil) printing, offset (planographic) printing, letterpress printing, or gravure (intaglio) printing, or the like. Note that the compositions of the present invention can be used as long as a method in which a liquid composition is used is employed without limitation to the above methods.

In a wet process, compared with a dry process such as an evaporation method or a sputtering method, a material is not scattered in a chamber, and therefore, material use efficiency is higher. Furthermore, facilities needed for a vacuum apparatus and the like can be reduced because the formation can be performed at atmospheric pressure. Further still, since the size of a substrate that is to be processed is not limited by the size of a vacuum chamber, it is possible to respond to use of a larger substrate to increase a processing area, whereby low cost and an improvement of productivity can be achieved. A wet process requires only heat treatment at about temperature at which a solvent of a composition can be removed, and thus is a so-called low temperature process. Therefore, it is possible to use even substrates and materials that can be degraded or deteriorated by heat treatment at high temperature.

Furthermore, since a liquid composition having fluidity is used for the formation, materials can be easily mixed. For example, an emission color that is to be obtained can be controlled by addition of a plurality of dopants to a composition. Further still, good coverage with respect to a region where the thin film is to be formed can also be achieved.

The thin film can be selectively formed by a droplet discharging method in which a composition can be discharged into a desired pattern, a printing method in which a composition can be transferred or drawn into a desired pattern, or the like. Therefore, a loss of a material is further prevented, and a material can be efficiently used, resulting in a reduction in manufacturing cost. Furthermore, such methods do not require shaping of the thin film by a photolithography process, and thus have the effects of simplifying the process and improving the productivity.

A thin film formed by a wet process with the use of any of the compositions of this embodiment, in which an anthracene derivative is dissolved in a solvent can be made to have a favorable film quality without defects or the like. Thus, with the use of such a composition and a thin film, a highly reliable light-emitting element (device) can be manufactured.

In this embodiment, since a wet process is employed for manufacture of a thin film and a light-emitting element high material use efficiency and a reduction in expensive facilities such as a large vacuum apparatus can be achieved, resulting in low cost and high productivity. Thus, by use of the present invention, a light-emitting device and an electronic device that are highly reliable can be manufactured at low cost and with high productivity.

[Embodiment 3]

One mode of a light-emitting element having a thin film formed by a wet process with the use of any of the compositions of the present invention which has an anthracene derivative and a solvent is described below with reference to FIG. 1A.

In the light-emitting element of the present invention, an EL layer containing at least a layer that contains a light-emitting substance (also referred to as a light-emitting layer) is interposed between a pair of electrodes. The EL layer may also have a plurality of layers in addition to the layer that contains a light-emitting substance. The plurality of layers is a combination of layers formed of a substance with a high carrier-injecting property and a substance with a high carrier-transporting property, which are stacked so that a light-emitting region is formed in a region away from the electrodes, that is, so that the carriers are recombined in an area away from the electrodes. In this specification, the layer formed of a substance with a high carrier-injecting property or a substance with a high carrier-transporting property is also referred to as a functional layer functioning to inject or transport carriers or the like. For the functional layer, it is possible to use a layer containing a substance with a high hole-injecting property (also referred to as a hole-injecting layer), a layer containing a substance with a high hole-transporting property (also referred to as a hole-transporting layer), a layer containing a substance with a high electron-injecting property (also referred to as an electron-injecting layer), a layer containing a substance with a high electron-transporting property (also referred to as an electron-transporting layer), and the like.

In the present invention, the layer that contains a light-emitting substance is formed by a wet process with the use of a liquid composition in which a light-emitting substance is dissolved in a solvent (any of the compositions described in Embodiment 1 or 2 which has an anthracene derivative and a solvent). In the wet process, a material for forming a thin film is dissolved in the solvent, and the liquid composition is attached to a region where the thin film is to be formed, the solvent is removed, and the resulting material is solidified, whereby the thin film is formed. In this specification, a film formed by a wet process, which is described as a film, may be extremely thin depending on its formation conditions, and the film does not necessarily maintain the form of a film; for example, it may have a discontinuous island structure or the like.

For the wet process, any of the following methods can be employed: a spin coating method, a roll coat method, a spray method, a casting method, a dipping method, a droplet discharging (ejection) method (an ink-jet method), a dispenser method, a variety of printing methods (a method by which a thin film can be formed in a desired pattern, such as screen (stencil) printing, offset (planographic) printing, letterpress printing, or gravure (intaglio) printing, or the like. Note that without limitation to the above methods, the compositions of the present invention can be used as long as a method in which a liquid composition is used is employed.

In a wet process, compared with a dry process such as an evaporation method or a sputtering method, a material is not scattered in a chamber, and therefore, material use efficiency is higher Furthermore, facilities needed for a vacuum apparatus and the like can be reduced because the formation can be performed at atmospheric pressure. Further still, since the size of a substrate that is to be processed is not limited by the size of a vacuum chamber, it is possible to respond to use of a larger substrate to increase a processing area, whereby low cost and an improvement of productivity can be achieved. A wet process requires only heat treatment at about temperature at which a solvent of a composition can be removed, and thus is a so-called low temperature process. Therefore, it is possible to use even substrates and materials that can be degraded or deteriorated by heat treatment at high temperature.

Furthermore, since a liquid composition having fluidity is used for the formation, materials can be easily mixed. For example, an emission color that is to be obtained can be controlled by addition of a plurality of dopants to a composition. Further still, good coverage with respect to a region where the thin film is to be formed can also be achieved.

The thin film can be selectively formed by a droplet discharging method in which a composition can be discharged into a desired pattern, a printing method in which a composition can be transferred or drawn into a desired pattern, or the like. Therefore, a loss of a material is further prevented, and a material can be efficiently used, resulting in a reduction in manufacturing cost. Furthermore, such methods do not require shaping of the thin film by a photolithography process, and thus have the effects of simplifying the process and improving the productivity.

A first electrode, a second electrode, and the functional layers (such as the hole-injecting layer, the hole-transporting layer, the electron-injecting layer, or the electron-transporting layer) which are included in a light-emitting element may be formed by the above wet process such as an inkjet method, a spin coating method, or a printing method, or by a dry process such as a vacuum evaporation method, a CVD method, or a sputtering method. The use of a wet process as described above enables the formation at atmospheric pressure using a simple device and process, and thus has the effects of simplifying the process and improving the productivity. In contrast, in a dry process, dissolution of a material is not needed, and thus, a material that has low solubility in a solution can be used to expand the range of material choices.

A method of forming each electrode or each functional layer may be determined depending on a material that is to be used or the order of the stacking, as appropriate. For a wet process in which a solvent is used, it is necessary to use a combination of the materials such that a lower thin film, which is a surface on which another film is to be formed, has low solubility in the solvent.

Figure 1B:
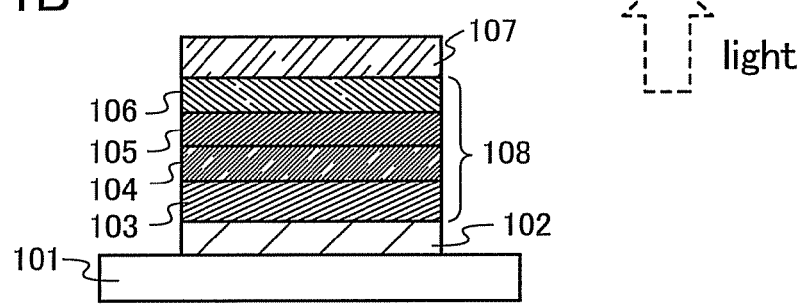
Figure 1C:
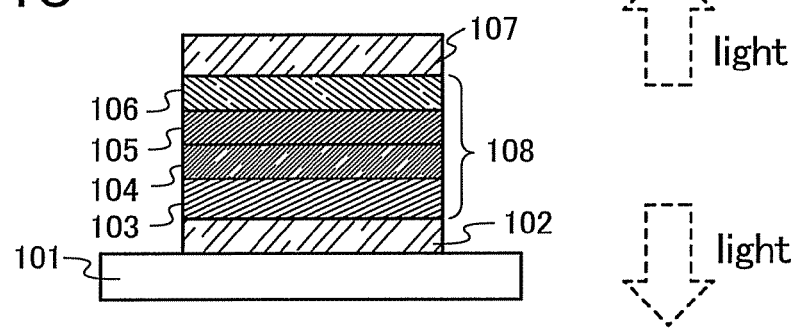

In a light-emitting element of this embodiment illustrated in each of FIGS. 1A to 1C, an EL layer 108 is provided between a first electrode 102 and a second electrode 107. The EL layer 108 has a first layer 103, a second layer 104, a third layer 105, and a fourth layer 106. In the light-emitting element of each of FIGS. 1A to 1C, the first electrode 102 is formed over a substrate 101; the first layer 103, the second layer 104, the third layer 105, and the fourth layer 106 are stacked over the first electrode 102 in this order; and the second electrode 107 is provided over the fourth layer 106. In the description below, it is assumed that the first electrode 102 functions as an anode and the second electrode 107 functions as a cathode in this embodiment.

The substrate 101 is used as a support of the light-emitting element. For the substrate 101, glass, quartz, plastic, or the like can be used, for example. Alternatively, a flexible substrate may be used. The flexible substrate is a substrate that can be bent, such as a plastic substrate made of polycarbonate, polyarylate, or polyether sulfone, for example. Alternatively, a film (made of polypropylene, polyester, vinyl, polyvinyl fluoride, vinyl chloride, or the like), an inorganic film formed by evaporation, or the like can be used. Note that other materials may also be used as long as they serve as a support in a manufacturing process of the light-emitting element.

As the first electrode 102, a metal, an alloy, a conductive compound, a mixture thereof or the like having a high work function (specifically, 4.0 eV or more) is preferably used. Specifically, for example, indium oxide-tin oxide (ITO: indium tin oxide), indium oxide-tin oxide containing silicon or silicon oxide, indium oxide-zinc oxide (IZO: indium zinc oxide), indium oxide containing tungsten oxide and zinc oxide (IWZO), and the like are given. Films of such conductive metal oxides are typically formed by sputtering, but may also be formed by applying a sol-gel method or the like. For example, a layer of indium oxide-zinc oxide (IZO) can be formed by a sputtering method using a target in which 1 wt % to 20 wt % of zinc oxide is added to indium oxide. Further, indium oxide containing tungsten oxide and zinc oxide (IWZO) can be formed by a sputtering method using a target in which 0.5 wt % to 5 wt % of tungsten oxide and 0.1 wt % to 1 wt % of zinc oxide are added to indium oxide. Alternatively, there are gold (Au), platinum (Pt), nickel (Ni), tungsten (W), chromium (Cr), molybdenum (Mo), iron (Fe), cobalt (Co), copper (Cu), palladium (Pd), nitride of a metal material (e.g., titanium nitride), and the like.

The first layer 103 is a layer including a substance having a high hole-injecting property. As the substance having a high hole-injecting property, molybdenum oxide, vanadium oxide, ruthenium oxide, tungsten oxide, manganese oxide, or the like may be used. Alternatively, the first layer 103 can be formed using any of the following materials: phthalocyanine compounds such as phthalocyanine (abbr.: $H_2Pc$) and copper phthalocyanine (abbr.: CuPc), aromatic amine compounds such as 4,4'-bis[N-(4-diphenylaminophenyl)-N-phenylamino]biphenyl (abbr. DPAB) and 4,4'-bis(N-{4-[N-(3-methylphenyl)-N-phenylamino]phenyl}-N-phenylamino)biphenyl (abbr: DNTPD), macromolecular compounds such as poly(3,4-ethylenedioxythiophene)/poly(styrenesulfonic acid) (abbr.: PEDOT/PSS), and the like.

Alternatively, a composite material including an organic compound and an inorganic compound can be used for the first layer 103. In particular, a composite material including an organic compound and an inorganic compound showing an electron-accepting property with respect to the organic compound is excellent in a hole-injecting property and a hole-transporting property since electrons are transferred between the organic compound and the inorganic compound and carrier density is increased.

In the case of using the composite material including an organic compound and an inorganic compound for the first layer 103, the first layer 103 can achieve an ohmic contact with the first electrode 102; therefore, a material of the first electrode can be selected regardless of the work function.

As the inorganic compound used for the composite material, an oxide of a transition metal is preferably used. Moreover, an oxide of metals belonging to Groups 4 to 8 of the periodic table can be used. Specifically, vanadium oxide, niobium oxide, tantalum oxide, chromium oxide, molybdenum oxide, tungsten oxide, manganese oxide, and rhenium oxide are preferable because of their high electron-accepting properties. Among these, molybdenum oxide is especially preferable because it is stable in air and its hygroscopic property is low so that it can be easily handled.

As the organic compound used for the composite material, any of a variety of compounds such as an aromatic amine compound, a carbazole derivative, an aromatic hydrocarbon, a macromolecular compound (such as an oligomer, a dendrimer, or a polymer), or the like can be used. Note that the organic compound used for the composite material is preferably an organic compound having a high hole-transporting property. Specifically, a substance having a hole mobility of greater than or equal to $10^{-6}$ cm$^2$/Vs is preferably used. However, a substance other than these compounds may also be used as long as it is a substance in which the hole-transporting property is higher than the electron-transporting property. Specific examples of the organic compound that can be used for the composite material are given below.

For example, as the aromatic amine compound that can be used for the composite material, the following can be given: N,N'-di(p-tolyl)-N,N'-diphenyl-p-phenylenediamine (abbr.: DTDPPA), 4,4'-bis[N-(4-diphenylaminophenyl)-N-phenylamino]biphenyl (abbr.: DPAB), 4,4'-bis(N-{4-[N'(3-methylphenyl)-N'-phenylamino]phenyl}-N-phenylamino)biphenyl (DNTPD), 1,3,5-tris[N-(4-diphenylaminophenyl)-N-phenylamino]benzene (abbr.: DPAS3B), and the like.

As specific examples of the carbazole derivative which can be used for the composite material, the following can be given: 3-[N-(9-phenylcarbazol-3-yl)-N-phenylamino]-9-phenylcarbazole (abbr.: PCzPCA1); 3,6-bis[N-(9-phenylcarbazol-3-yl)-N-phenylamino]-9-phenylcarbazole (abbrev.: PCzPCA2); 3-[N-(1-naphthyl)-N-(9-phenylcarbazol-3-yl) amino]-9-phenylcarbazole (abbrev.: PCzPCN1); and the like.

Further, the following can also be used: 4,4'-di(N-carbazolyl)biphenyl (abbrev.: CBP); 1,3,5-tris[4-(N-carbazolyl) phenyl]benzene (abbr.: TCPB); 9-[4-(N-carbazolyl)]phenyl-10-phenylanthracene (abbr.: CzPA); 1,4-bis[4-(N-carbazolyl)phenyl]-2,3,5,6-tetraphenylbenzene; and the like.

As the aromatic hydrocarbon which can be used for the composite material, for example, the following can be given: 2-tert-butyl-9,10-di(2-naphthyl)anthracene (abbr.: t-BuDNA); 2-tert-butyl-9,10-di(1-naphthyl)anthracene; 9,10-bis(3,5-diphenylphenyl)anthracene (abbr.: DPPA); 2-tert-butyl-9,10-bis(4-phenylphenyl)anthracene (abbr.: t-BuDBA); 9,10-di(2-naphthyl)anthracene (abbr.: DNA); 9,10-diphenylanthracene (abbr.: DPAnth); 2-tert-butylanthracene (abbr.: t-BuAnth); 9,10-bis(4-methyl-1-naphthyl) anthracene (abbr.: DMNA); 2-tert-butyl-9,10-bis[2-(1-naphthyl)phenyl]anthracene; 9,10-bis[2-(1-naphthyl)phenyl] anthracene; 2,3,6,7-tetramethyl-9,10-di(1-naphthyl) anthracene; 2,3,6,7-tetramethyl-9,10-di(2-naphthyl) anthracene; 9,9'-bianthryl; 10,10'-diphenyl-9,9'-bianthryl; 10,10'-bis(2-phenylpenyl)-9,9'-bianthryl; 10,10'-bis[(2,3,4,5,6-pentaphenyl phenyl]9,9'-bianthryl; anthracene; tetracene; rubrene; perylene; 2,5,8,11-tetra(tert-butyl)perylene; or the like. In addition, pentacene, coronene, or the like can also be used. In this manner, it is more preferable to use an aromatic hydrocarbon having hole mobility of $1 \times 10^{-6}$ cm$^2$/Vs or more and having 14 to 42 carbon atoms.

Note that the aromatic hydrocarbon which can be used for the composite material may have a vinyl skeleton. As examples of the aromatic hydrocarbon having a vinyl group, 4,4'-bis(2,2-diphenylvinyl)biphenyl (abbr.: DPVBi), 9,10-bis [4-(2,2-diphenylvinyl)phenyl]anthracene (abbr.: DPVPA), and the like can be given.

A macromolecular compound such as poly(N-vinylcarbazole) (abbr.: PVK) or poly(4-vinyltriphenylamine) (abbr.: PVTPA) can also be used.

As a substance for forming the second layer 104, a substance having a high hole-transporting property, specifically, an aromatic amine compound (that is, a compound having a benzene ring-nitrogen bond) is preferably used. As examples of the material which are widely used, the following can be given: 4,4'-bis[N-(3-methylphenyl)-N-phenylamino]biphenyl; a derivative thereof such as 4,4'-bis[N-(1-napthyl)-N-phenylamino]biphenyl (hereinafter referred to as NPB); and a starburst aromatic amine compound such as 4,4',4''-tris(N,N-diphenyl-amino)triphenylamine, 4,4',4''-tris[N-(3-methylphenyl)-N-phenylamino]triphenylamine, and the like. These substances described here are mainly substances each having a hole mobility of greater than or equal to $10^{-6}$ cm$^2$/Vs. However, any substance other than the above substances may also be used as long as it is a substance in which the hole-transporting property is higher than the electron-transporting property. Note that without limitation to a single layer, the second layer 104 may be a mixed layer of the aforementioned substances or a stack of two or more layers.

Alternatively, a material with a hole-transporting property may be added to a macromolecular compound that is electrically inactive, such as PMMA.

Further alternatively, a macromolecular compound such as poly(N-vinylcarbazole) (abbr: PVK), poly(4-vinyltriphenylamine) (abbr.: PVTPA), poly[N-(4-{N'-[4-(4-diphenylamino)phenyl]phenyl-N'-phenylamino}phenyl)methacrylamide] (abbr.: PTPDMA), or poly[N,N'-bis(4-butylphenyl)-N,N'-bis(phenyl)benzidine (abbr.: poly-TPD) may be used, and further, the material with a hole-ransporting property may be added to the above macromolecular compound, as appropriate.

The third layer 105 is a layer that contains a light-emitting substance. In this embodiment, the third layer 105 is formed using any of the compositions described in Embodiment 1 or 2. Specifically, any of the compositions described in Embodiment 1 or 2 may be applied by a wet process (e.g., a droplet discharging method (an ink-jet method), a spin coating method, a printing method), and then, the solvent is removed. For removing the solvent, heat treatment, low pressure treatment, heat treatment under low pressure, and the like can be given. The material use efficiency can be improved by employing a wet process, whereby the manufacturing cost of light-emitting elements can be reduced. The anthracene derivative contained in the thin film formed using any of the compositions of the present invention emits blue light and thus can be preferably used as a light-emitting substance for a light-emitting element.

Alternatively, for the third layer 105, any of the compositions of the present invention which has an anthracene derivative and a solvent can also be used as a host. Light emission from a dopant that is to serve as a light-emitting substance can be obtained with a structure in which the dopant that is to serve as a light-emitting substance is dispersed in the composition of the present invention which has an anthracene derivative and a solvent.

When the anthracene derivative in any of the compositions of the present invention is used as a material in which another light-emitting substance is dispersed, an emission color derived from the light-emitting substance can be obtained. Further, it is also possible to obtain an emission color that is a mixture of the emission color derived from the anthracene derivative in any of the compositions of the present invention and the emission color derived from the light-emitting substance dispersed in the anthracene derivative.

In this case, any of a variety of materials can be used as the light-emitting substance dispersed in the anthracene derivative contained in any of the compositions of the present invention. Specifically, fluorescent substances that emit fluorescence, such as 9,10-diphenyl-2-[N-phenyl-N-(9-phenyl-9H-carbazol-3-yl)amino]anthracene (abbr: 2PCAPA), 4-(dicyanomethylene)-2-methyl-6-(p-dimethylaminostyryl)-4H-pyran (abbr.: DCM1), 4-(dicyanomethylene)-2-methyl-6-(julolidin-4-yl-vinyl)-4H-pyran (abbreviated to DCM2), N,N-dimethylquinacridone (abbr.: DMQd), rubrene, N,N'-bis[4-(9H-carbazol-9-yl)phenyl]-N,N'-diphenylstilbene-4,4'-diamine (abbr.: YGA2S), or 4-(9H-carbazol-9-yl)-4'-(10-phenyl-9-anthryl)triphenylamine (abbr.: YGAPA) can be used. Alternatively, phosphorescent substances that emit phosphorescence, such as (acetylacetonato) bis[2,3-bis(4-fluorophenyl)quinoxalinato]iridium(III) (abbr: Ir(Fdpq)$_2$(acac)) or (2,3,7,8,12,13,17,18-octaethyl-21H, 23H-porphyrinato)platinum(II) (abbr.: PtOEP) can also be used.

The fourth layer 106 can be formed using a substance with a high electron-transporting property. For example, a layer containing a metal complex having a quinoline skeleton or a benzoquinoline skeleton, such as tris(8-quinolinolato)aluminum (abbr.: Alq), tris(4-methyl-8-quinolinolato)aluminum (abbr.: Almq$_3$), bis(10-hydroxybenzo[h]-quinolinato)beryllium (abbr.: BeBq$_2$), or bis(2-methyl-8-quinolinolato)(4-phenylphenolato)aluminum (abbr.: BAlq) can be used. Further, a metal complex containing oxazole-based or thiazole-based ligand such as bis[2-(2'-hydroxyphenyl)benzoxazolato]zinc (abbr. Zn(BOX)$_2$) and bis[2-(2'-hydroxyphenyl)benzothiazolato]zinc (abbr. Zn(BTZ)$_2$) can also be used. Besides the metal complexes, 2-(4-biphenylyl)-5-(4-tert-butylphenyl)-1,3,4-oxadiazole (abbr.: PBD)), 1,3-bis[5-(p-tert-butylphenyl)-1,3,4-oxadiazol-2-yl]benzene (abbr.: OXD-7), 3-(4-biphenylyl)-4-phenyl-5-(4-tert-butylphenyl)-1,2,4-triazole (abbr.: TAZ), bathophenanthroline (abbr.: BPhen), bathocuproine (abbr.: BCP), or the like can also be used. The substances described here are mainly substances having an electron mobility of 10$^{-6}$ cm$^2$/Vs or more. Note that a substance other than the above substances may be used as long as it has a higher electron-transporting property than a hole transporting property. Further, without limitation to a single layer, the electron-transporting layer may be a stack of two or more layers of the aforementioned substances.

Further, a layer having a function of promoting electron injection (an electron-injecting layer) may be provided between the fourth layer 106 and the second electrode 107. For the layer having a function of promoting electron injection, an alkali metal, an alkaline earth metal, or a compound thereof, such as lithium fluoride (LiF), cesium fluoride (CsF), or calcium fluoride (CaF$_2$) can be used. A layer in which an alkali metal, an alkaline earth metal, or a compound thereof is contained in a substance with an electron-transporting property, such as a layer in which magnesium (Mg) is contained in Alq, can be used. Note that it is preferable to use the layer formed of a substance having an electron transporting property in which an alkali metal or an alkaline earth metal is mixed as the electron injecting layer because electrons can be efficiently injected from the second electrode 107.

The second electrode 107 can be formed using a metal, an alloy, or an electrically conductive compound, a mixture of them, or the like having a low work function (specifically less than or equal to 3.8 eV). As specific examples of such a cathode material, an element belonging to Group 1 or Group 2 in the periodic table, that is, an alkali metal such as lithium (Li) or cesium (Cs); an alkaline-earth metal such as magnesium (Mg), calcium (Ca), or strontium (Sr); an alloy containing the element belonging to Group 1 or Group 2 (MgAg, AlLi); a rare-earth metal such as europium (Eu) or ytterbium (Yb); an alloy thereof; and the like can be given. However, by providing a layer having a function of promoting electron injection between the second electrode 107 and the fourth layer 106 so that it is stacked with the second electrode, various conductive materials such as Al, Ag, ITO, or ITO containing silicon or silicon oxide can be used for the second electrode 107 regardless of the magnitude of the work function.

Further, the anthracene derivative contained in any of the compositions of the present invention can be used for the functional layer of the light-emitting element. The anthracene derivative in which at least one of A$^1$ and A$^2$ represents a diarylamino group in the above general formula (1) enables the functional layer containing the anthracene derivative to function as a hole-transporting layer or a hole-injecting layer, and accordingly the anthracene derivative can be used for the first layer 103 or the second layer 104. The anthracene derivative in which both A$^1$ and A$^2$ do not represent a diarylamino group in the above general formula (1) enables the functional layer containing the anthracene derivative to function as an electron-transporting layer or an electron-injecting layer, and accordingly, the anthracene derivative can be used for the fourth layer 106. Thus, the functional layers (the first layer 103, the second layer 104, and the fourth layer 106) of the light-emitting element can be formed by a wet process using any of the compositions of the present invention which has an anthracene derivative and a solvent. Furthermore, when the functional layers are formed by a wet process using any of the compositions of the present invention which has an anthracene derivative and a solvent, the third layer 105 containing a light-emitting substance may be formed using any other phosphor by a dry process such as an evaporation method.

For the formation of the first layer 103, the second layer 104, the third layer 105, and the fourth layer 106, any of a variety of methods such as an evaporation method, a droplet discharging method (an ink-jet method), a spin coating method, or a printing method can be employed. Further, a different deposition method can be employed for each electrode or each layer.

In the light-emitting element of the present invention having the structure as described above, the potential difference generated between the first electrode 102 and the second electrode 107 makes a current flow, whereby holes and electrons are recombined in the third layer 105 that is a layer containing a substance with a high light-emitting property and thus light is emitted. That is, a light-emitting region is formed in the third layer 105.

Light emission is extracted outside through one of or both the first electrode 102 and the second electrode 107. Thus, one of or both the first electrode 102 and the second electrode 107 are light-transmissive electrodes. When only the first electrode 102 is a light-transmissive electrode, light emission is extracted from the substrate side through the first electrode 102, as illustrated in FIG. 1A. In contrast, when only the second electrode 107 is a light-transmissive electrode, light emission is extracted from a side opposite to the substrate side through the second electrode 107, as illustrated in FIG. 1B. When both the first electrode 102 and the second electrode 107 are light-transmissive electrodes, light emission is extracted from both the substrate side and the side opposite to the substrate side through the first electrode 102 and the second electrode 107, as illustrated in FIG. 1C.

The structure of layers provided between the first electrode 102 and the second electrode 107 is not limited to the above example. A structure other than the above may be employed as long as a light-emitting region in which holes and electrons are recombined is provided in a portion away from the first electrode 102 and the second electrode 107 in order to prevent quenching due to proximity of the light-emitting region to a metal.

That is, there is no particular limitation on the stacked structure of the layers. It is acceptable as long as the light-emitting layer containing any of the compositions of the present invention is freely combined with the layers each containing a substance with a high electron-transporting property, a substance with a high hole-transporting property, a substance with a high electron-injecting property, a substance with a high hole-injecting property, a bipolar substance (a substance with a high electron-transporting and hole-transporting property), a hole-blocking material, or the like.

Figure 2:
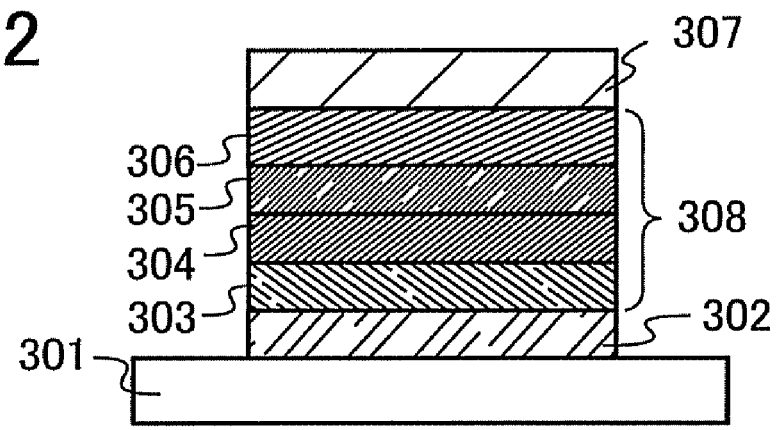
FIG. 2 is a view illustrating a light-emitting element.

In a light-emitting element illustrated in FIG. 2, an EL layer 308 is provided between a first electrode 302 and a second electrode 307 over a substrate 301. The EL layer 308 has a first layer 303 that contains a substance with a high electron-transporting property, a second layer 304 that contains a light-emitting substance, a third layer 305 that contains a substance with a high hole-transporting property, and a fourth layer 306 that contains a substance with high hole-injecting property. The first electrode 302 that is to function as a cathode, the first layer 303 formed of a substance with a high electron-transporting property, the second layer 304 that contains a light-emitting substance, the third layer 305 formed of a substance with a high hole-transporting property, the fourth layer 306 formed of a substance with high hole-injecting property, and the second electrode 307 that is to function as an anode are stacked in this order.

Note that, when the light-emitting element described in this embodiment is applied to a display device and layers containing a light-emitting substance are formed separately for each color, it is preferable that they be selectively formed by a wet process. The use of a droplet discharging method makes it easier to form the layers containing a light-emitting substance separately for each color even if a large substrate is employed, whereby the productivity is improved.

A specific method for forming a light-emitting element is described below.

In the light-emitting element of the present invention, an EL layer is interposed between a pair of electrodes. The EL layer includes at least a layer that contains a light-emitting substance (also referred to as a light-emitting layer) formed using any of the compositions of the present invention by a wet process. Furthermore, in addition to a layer containing a light-emitting substance, the EL layer may include a functional layer (e.g., a hole-injecting layer, a hole-transporting layer, an electron-transporting layer, or an electron-injecting layer). Each electrode (the first electrode or the second electrode) and each functional layer may be formed by any of the wet processes such as a droplet discharging method (an ink-jet method), a spin coating method, or a printing method, or by a dry process such as a vacuum evaporation method, a CVD method, or a sputtering method. The use of a wet process enables the formation at atmospheric pressure using a simple device and process, thereby having the effects of simplifying the process and improving the productivity. In contrast, in a dry process, dissolution of a material is not needed, and thus, a material that has low solubility in a solution can be used to expand the range of material choices.

The layer containing a light-emitting substance is formed by a wet process using any of the compositions of the present invention, and thus, all the thin films included in the light-emitting element may be formed by a wet process. In this case, the light-emitting element can be manufactured with only facilities needed for a wet process. Alternatively, the stacked layers to the layer containing a light-emitting substance may be formed by a wet process whereas the functional layer, the second electrode, or the like which are stacked over the layer containing a light-emitting substance may be formed by a dry process. Further alternatively, the first electrode and the functional layers may be formed by a dry process before the formation of the layer containing a light-emitting substance whereas the layer containing a light-emitting substance, the functional layer stacked thereover, and the second electrode may be formed by a wet process. Naturally, the present invention is not limited to such a method, and the light-emitting element can be formed by appropriate selection from a wet process and a dry process depending on a material that is to be used, necessary film thickness, and the interface state.

One example is described below. Over a first electrode, PEDOT/PSS is used for forming a hole-injecting layer. Since PEDOT/PSS is soluble in water, it can be deposited as an aqueous solution by a spin coating method, an ink-jet method, or the like. A hole-transporting layer is not provided, and a layer containing a light-emitting substance is provided over the hole-injecting layer. The layer containing a light-emitting substance can be formed by an ink-jet method with the use of any of the compositions described in Embodiment 1 or 2 which contains a solvent in which the hole-injecting layer (formed of PEDOT/PSS) which has been already formed does not dissolve, (e.g., a solvent having an aromatic ring (e.g., a benzene ring) such as toluene, xylene, methoxybenzene (anisole), dodecylbenzene, or a mixed solvent of dodecylbenzene and tetralin; or an organic solvent without an aromatic ring, such as dimethylsulfoxide (DMSO), dimethylformamide (DMF), or chloroform). Next, an electron-transporting layer is formed over the layer containing a light-emitting substance. If the electron-transporting layer is formed by a wet process, it need be formed using a solvent in which the hole-injecting layer and the layer containing a light-emitting substance which have been already formed do not dissolve. In that case, the selection range of solvents is limited; therefore, the use of a dry process is easier to form the electron-transporting layer. Thus, when the formation of the electron-transporting layer to the second electrode is performed in vacuum consistently by a vacuum evaporation method, the process can be simplified.

In this embodiment, the light-emitting element is manufactured over a substrate made of glass, plastic, or the like. When a plurality of such light-emitting elements is manufactured over one substrate, a passive matrix light-emitting device can be manufactured. Alternatively, for example, a thin film transistor (TFT) is formed over a substrate formed using glass, plastic, or the like, and then, a light-emitting element may be manufactured over an electrode that is electrically connected to the TFT. Thus, an active matrix light-emitting device in which drive of the light-emitting element is controlled by the TFT can be manufactured. Note that there is no particular limitation on the structure of the TFT. Either a staggered TFT or an inverted staggered TFT may be employed. Further, there is no particular limitation on the crystallinity of a semiconductor used for forming the TFT, and an amorphous semiconductor, a crystalline semiconductor, or a single-crystal semiconductor may be used. In addition, a driver circuit formed over a TFT substrate may be formed using n-channel and p-channel TFTs, or using either n-channel or p-channel TFTs.

A thin film formed by a wet process with the use of any of the compositions of this embodiment, in which an anthracene derivative is dissolved in a solvent, can be made to have a favorable film quality without defects or the like. Thus, with the use of such a composition and a thin film, a highly reliable light-emitting element (device) can be manufactured.

In this embodiment, since a wet process is employed for manufacture of a thin film and a light-emitting element high material use efficiency and a reduction in expensive facilities such as a large vacuum apparatus can be achieved, resulting in low cost and high productivity. Thus, by use of the present invention, a light-emitting device and an electronic device that are highly reliable can be manufactured at low cost with high productivity.

(Embodiment 4)

In this embodiment, a mode of a light-emitting element in which a plurality of light-emitting units according to the present invention is stacked (hereinafter, referred to as a stacked-type element) is described with reference to FIG. 3. The light-emitting element is a stacked-type light-emitting element including a plurality of light-emitting units between a first electrode and a second electrode.

Figure 3:
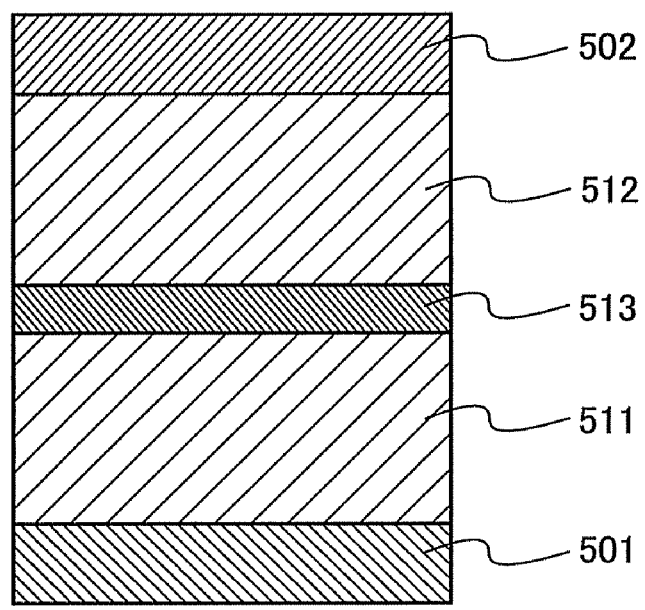
FIG. 3 is a view illustrating a light emitting element.

In FIG. 3, a first light-emitting unit 511 and a second light-emitting unit 512 are stacked between a first electrode 501 and a second electrode 502. The first electrode 501 and the second electrode 502 can be similar to the electrodes described in Embodiment 2. Structures of the first light-emitting unit 511 and the second light-emitting unit 512 may be the same or different from each other and can be similar to the structure described in Embodiment 2.

A charge generation layer 513 contains a composite material of an organic compound and a metal oxide. The composite material of an organic compound and a metal oxide is described in Embodiment 2 or 5 and contains an organic compound and a metal oxide such as vanadium oxide, molybdenum oxide, or tungsten oxide. As the organic compound, a variety of compounds such as aromatic amine compounds, carbazole derivatives, aromatic hydrocarbons, or macromolecular compounds (such as oligomers, dendrimers, or polymers) can be used. Note that an organic compound having a hole mobility of greater than or equal to $10^{-6}$ cm$^2$/(V·s) is preferably applied as the organic compound. However, a substance other than these compounds may also be used as long as it is a substance in which the hole-transporting property is higher than the electron-transporting property. Since the composite material of an organic compound and a metal oxide is superior in carrier-injecting property and carrier-transporting property, low-voltage driving or low-current driving can be realized.

Note that the charge generation layer 513 may be formed by a combination of a composite material of an organic compound and a metal oxide with another material. For example, the charge generation layer 513 may be formed by a combination of a layer containing the composite material of an organic compound and a metal oxide with a layer containing one compound selected from among electron-donating substances and a compound having a high electron-transporting property. Further, the charge generation layer 513 may be formed by a combination of a layer containing the composite material of an organic compound and a metal oxide with a transparent conductive film.

In any case, the charge generation layer 513 interposed between the first light-emitting unit 511 and the second light-emitting unit 512 is acceptable as long as electrons are injected to a light-emitting unit on one side and holes are injected to a light-emitting unit on the other side when a voltage is applied to the first electrode 501 and the second electrode 502.

In this embodiment the light-emitting element having two light-emitting units is described; however, the present invention can be applied in a similar manner to a light-emitting element in which three or more light-emitting units are stacked. When a plurality of light-emitting units is arranged to be partitioned from each other with a charge generation layer between a pair of electrodes, like the light-emitting element according to this embodiment, emission from a region of high luminance can be realized at a low current density, and thus, an element with a long life can be achieved. When the light-emitting element is applied to a lighting apparatus, a drop in voltage due to the resistance of an electrode material can be suppressed, and thus, uniform emission in a large area can be achieved. A light-emitting device that can be driven at a low voltage and has low power consumption can be realized.

A layer containing a light-emitting substance is provided in each of the first light-emitting unit 511 and the second light-emitting unit 512. Also in this embodiment, as described in Embodiment 1 or 2, the layer containing a light-emitting substance is formed by a wet process using any of the compositions of the present invention which has an anthracene derivative and a solvent.

A thin film formed by a wet process with the use of any of the compositions of this embodiment in which an anthracene derivative is dissolved in a solvent, can be made to have a favorable film quality without defects or the like. Thus, with the use of such a composition and a thin film, a highly reliable light-emitting element (device) can be manufactured.

In this embodiment, since a wet process is employed for manufacture of a thin film and a light-emitting element, high material use efficiency and a reduction in expensive facilities such as a large vacuum apparatus can be achieved, resulting in low cost and high productivity. Thus, by using the present invention, a light-emitting device and an electronic device that are highly reliable can be manufactured at low cost with high productivity.

This embodiment can be combined with any other embodiment as appropriate.

(Embodiment 5)

In this embodiment, a light-emitting device manufactured using any of the compositions of the present invention which has an anthracene derivative and a solvent is described.

In this embodiment, a light-emitting device manufactured using any of the compositions of the present invention which has an anthracene derivative and a solvent is described using FIGS. 4A and 4B. FIG. 4A is a top view of a light-emitting device, and FIG. 4B is a cross-sectional view taken along lines A-B and C-D of FIG. 4A. A driver circuit portion (a source side driver circuit) 601, a pixel portion 602, and a driver circuit portion (a gate side driver circuit) 603 are indicated by dotted lines. Reference numerals 604 and 605 denote a sealing substrate and a sealing material, respectively. A portion enclosed by the sealing material 605 corresponds to a space 607.

A lead wiring 608 is a wiring used to transmit signals to be inputted to the source side driver circuit 601 and the gate side driver circuit 603 and receives a video signal, a clock signal, a start signal, a reset signal, and the like from a flexible printed circuit (FPC) 609 which is an external input terminal, Note that only the FPC is illustrated in this case; however, the FPC may be provided with a printed wiring board (PWB). The category of the light-emitting device in this specification includes not only a light-emitting device itself but also a light-emitting device to which an FPC or a PWB is attached.

Next, a cross-sectional structure is described with reference to FIG. 4B. The driver circuit portion and the pixel portion are formed over an element substrate 610. In this case, one pixel in the pixel portion 602 and the source side driver circuit 601 which is the driver circuit portion are illustrated.

A CMOS circuit, which is a combination of an n-channel TFT 623 and a p-channel TUT 624, is formed as the source side driver circuit 601. Further, a TFT for forming the driver circuit may be any of a variety of circuits such as a CMOS circuit, a PMOS circuit, or an NMOS circuit. Although a driver-integration type device, in which a driver circuit is formed over a substrate, is described in this embodiment, a driver circuit is not necessarily formed over the substrate but can be formed externally from a substrate.

The pixel portion 602 is formed using a plurality of pixels each of which includes a switching TFT 611, a current control TFT 612, and a first electrode 613 which is electrically connected to a drain of the current control TFT 612. Note that an insulating layer 614 is formed to cover end portions of the first electrode 613. In this case, the insulating layer 614 is formed using a positive photosensitive acrylic resin film. The first electrode 613 is formed over an insulating layer 619 which is an interlayer insulating layer.

The insulating layer 614 is formed so as to have a curved surface having curvature at an upper end portion or a lower end portion thereof in order to make the coverage favorable. For example, in the case of using a positive photosensitive acrylic resin as a material for the insulating layer 614, it is preferable that the insulating layer 614 be formed so as to have a curved surface with a radius of curvature (0.2 μm to 3 μm) only at the upper end portion thereof. The insulating layer 614 can be formed using either a negative type which becomes insoluble in an etchant by light irradiation or a positive type which becomes soluble in an etchant by light irradiation.

A layer 616, which contains a light-emitting substance, and a second electrode 617 are formed over the first electrode 613. In this case, it is preferred that the first electrode 613 serving as an anode be formed using a material with a high work function. For example, the first electrode 613 can be formed using a single-layer film of an ITO film, an indium tin oxide film containing silicon, an indium oxide film containing 2 wt % to 20 wt % of zinc oxide, a titanium nitride film, a chromium film, a tungsten film, a Zn film, a Pt film, or the like; a stack of a titanium nitride film and a film containing aluminum as its main component; or a stacked film such as a film having a three-layer structure of a titanium nitride film, a film containing aluminum as its main component, and another titanium nitride film. When the first electrode 613 has a stacked structure, resistance as a wiring is low, a good ohmic contact is formed, and further, the first electrode 613 can be made to function as an anode.

The layer 616 containing a light-emitting substance is formed by a wet process using any of the compositions of the present invention, which has an anthracene derivative and a solvent, described in Embodiment 1 or 2. For the wet process, any of a variety of methods such as a droplet discharging method such as an ink-jet method, a printing method, a spin coating method, and the like can be used. The layer 616 containing a light-emitting substance may be formed using another material such as a low molecular weight material, a material with a molecular weight such as that of an oligomer or a dendrimer, or a macromolecular material.

In this embodiment, with reference to FIGS. 10A to 10D and FIG. 11, an example is described in which the layer 616 containing a light-emitting substance is formed by a droplet discharging method as a wet process. FIGS. 10A to 10D illustrate a manufacturing process of a light-emitting element of the light-emitting device illustrated in FIGS. 4A and 4B.

Figure 10A:
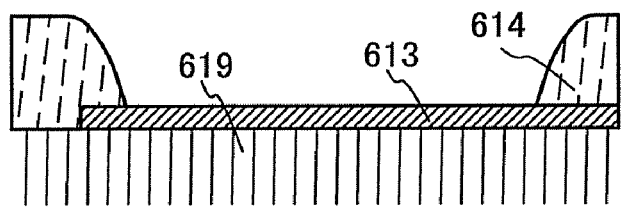
FIGS. 10A to 10D are views illustrating a method for manufacturing a light-emitting device.
Figure 10B:
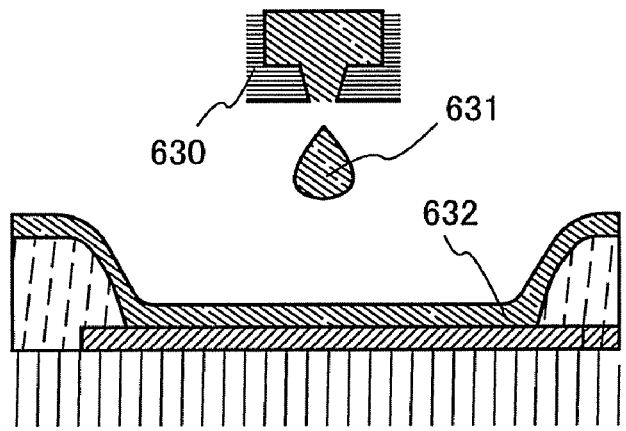
Figure 10C:
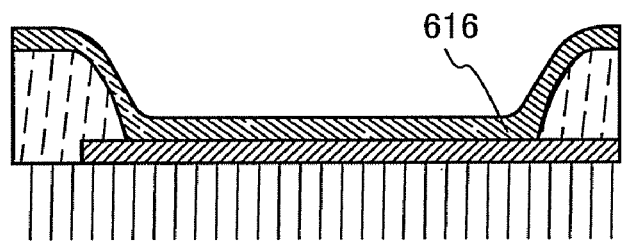
Figure 10D:
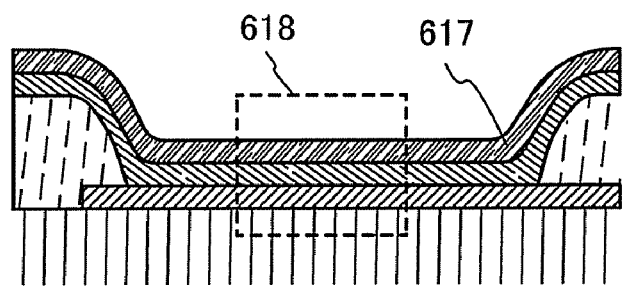

In FIG. 10A, the first electrode 613 is formed over the insulating layer 619, and the insulating layer 614 is formed so as to cover a part of the first electrode 613. In an exposed portion of the first electrode 613 which is an opening of the insulating layer 614, a droplet 631 is discharged from a droplet discharge device 630 to form a layer 632 containing a composition. The droplet 631 is any of the compositions of the present invention which has an anthracene derivative and a solvent and attached to the first electrode 613 (see FIG. 10B). The solvent is removed from the layer 632 containing the composition, and the resulting material is solidified, whereby the layer 616 containing a light-emitting substance is formed (see FIG. 10C). The solvent may be removed by drying or a heating step. In addition, the step of discharging the composition may be performed under reduced pressure. The second electrode 617 is formed over the layer 616 containing a light-emitting substance, whereby a light-emitting element 618 is manufactured (see FIG. 10D), When the layer 616 containing a light-emitting substance is formed by a droplet discharging method as described above, the composition can be selectively discharged into a region in which the layer is to be formed, and accordingly, waste of material can be reduced. Furthermore, a photolithography process or the like for shaping is not needed, and thus, the process can be simplified and cost reduction can be achieved.

A droplet discharging means used in this embodiment is generally a means to discharge liquid droplets, such as a nozzle equipped with a composition discharge outlet, a head having one or a plurality of nozzles.

Figure 11:
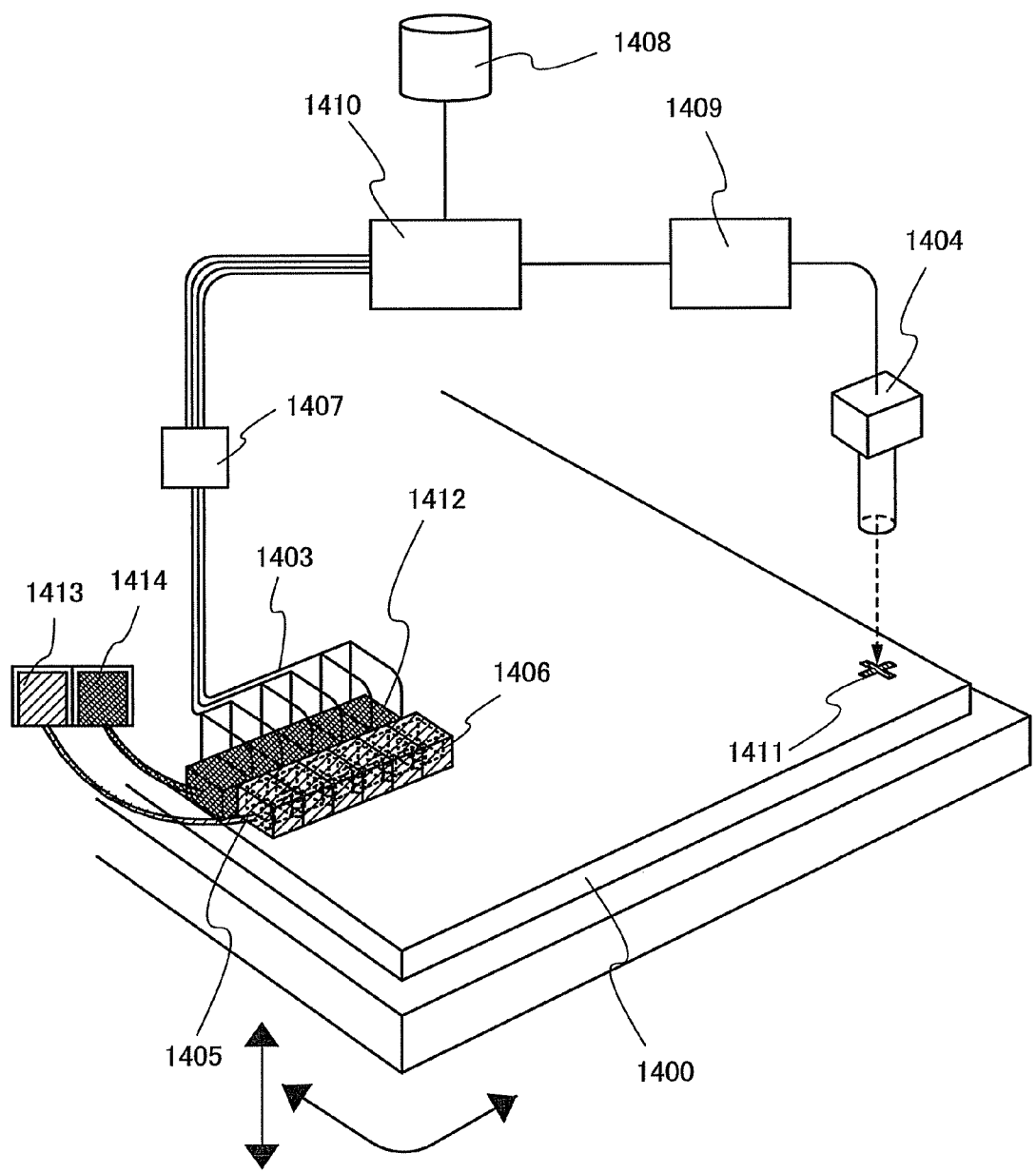
FIG. 11 is a view illustrating an example of a droplet discharging apparatus that can be applied.

One mode of a droplet discharging apparatus used for a droplet discharging method is illustrated in FIG. 11. Each of heads 1405 and 1412 of a droplet discharging means 1403 is connected to a control means 1407, and this control means 1407 is controlled by a computer 1410; thus, a preprogrammed pattern can be drawn. The timing for dawning may be determined, for example, based on a marker 1411 formed over a substrate 1400. Alternatively, a reference point may be fixed based on an edge of the substrate 1400. The reference point is detected by an imaging means 1404 and converted into a digital signal by an image processing means 1409. Then, the digital signal is recognized by the computer 1410, and then, a control signal is generated and transmitted to the control means 1407. An image sensor or the like using a charge coupled device (CCD) or a complementary metal oxide semiconductor (CMOS) can be used for the imaging means 1404. Needless to say, information about a pattern to be formed over the substrate 1400 is stored in a storage medium 1408, and the control signal is transmitted to the control means 1407 based on the information, whereby the head 1405 and the head 1412 of the droplet discharging means 1403 can be individually controlled. A material to be discharged is supplied to the heads 1405 and 1412 from a material supply sources 1413 and 1414, respectively, through pipes.

Inside the head 1405, a space filled with a liquid material as indicated by a dotted line 1406 and a nozzle which is a discharge outlet are provided. Although not illustrated, an internal structure of the head 1412 is similar to that of the head 1405. When the nozzle sizes of the heads 1405 and 1412 are different from each other, different materials can be discharged with different widths simultaneously. Each head can discharge and draw a plurality of light-emitting materials. In the case of drawing over a large area, the same material can be simultaneously discharged to be drawn from a plurality of nozzles in order to improve throughput. When a large substrate is used, the heads 1405 and 1412 can freely move over the substrate in a direction indicated by the arrows in FIG. 11, and a region where the material is to be drawn can be freely set. Thus, a plurality of the same patterns can be drawn over one substrate.

In addition, the step of discharging the composition may be performed under reduced pressure. The substrate may be heated when the composition is discharged. After the composition is discharged, either or both steps of drying and baking are performed. Both the drying and baking steps are heat treatments but different in purpose, temperature, and time period. The steps of drying and baking are each performed under normal pressure or under reduced pressure, by laser light irradiation, rapid thermal annealing, heating using a heating furnace, or the like. Note that there is no particular limitation on the timing and the number of heat treatments. The temperature at that time for performing each of the steps of drying and baking in a favorable manner depends on the material of the substrate and properties of the composition.

As a material used for the second electrode 617 which is formed over the layer 616 containing a light-emitting substance and serves as a cathode, it is preferable to use a material with a low work function (e.g., Al, Mg, Li, Ca, or an alloy or a compound thereof such as MgAg, Mg—In, Al—Li, LiF, or $CaF_2$). When light generated in the layer 616 containing a light-emitting substance is transmitted through the second electrode 617, the second electrode 617 may be formed using a stack of a metal thin film with a reduced film thickness and a transparent conductive film (e.g., a film of ITO, indium oxide containing 2 wt % to 20 wt % of zinc oxide, indium tin oxide containing silicon or silicon oxide, or zinc oxide (ZnO)).

The sealing substrate 604 is attached using the sealing material 605 to the element substrate 610; thus, a light-emitting element 618 is provided in the space 607 enclosed by the element substrate 610, the sealing substrate 604, and the sealing material 605. Note that the space 607 is filled with a filler. The space 607 is filled with an inert gas (e.g., nitrogen or argon) or the sealing material 605 in some cases.

It is preferable that an epoxy-based resin be used to form the sealing material 605 and that such a material permeate little moisture and oxygen as much as possible. As the sealing substrate 604, a plastic substrate formed using fiberglass-reinforced plastics (FRP), polyvinyl fluoride (PVF), polyester, acrylic, or the like can be used as well as a glass substrate or a quartz substrate. Alternatively, a film (made of polypropylene, polyester, vinyl, polyvinyl fluoride, vinyl chloride, or the like), or an inorganic evaporated film can also be used.

Accordingly, a light-emitting device manufactured using any of the compositions of the present invention which has an anthracene derivative and a solvent can be obtained.

Figure 5A:
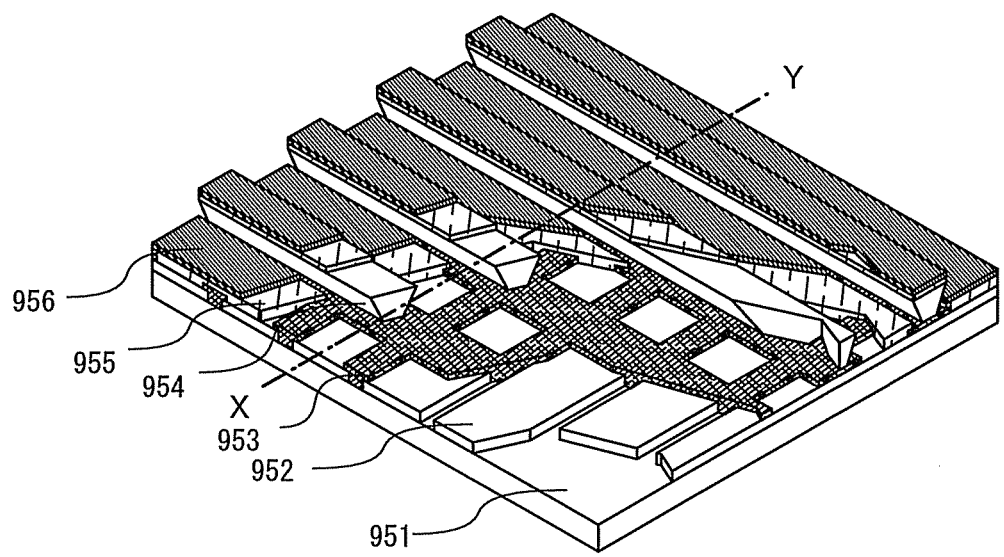
FIGS. 5A and 5B are views illustrating a light-emitting device.
Figure 5B:
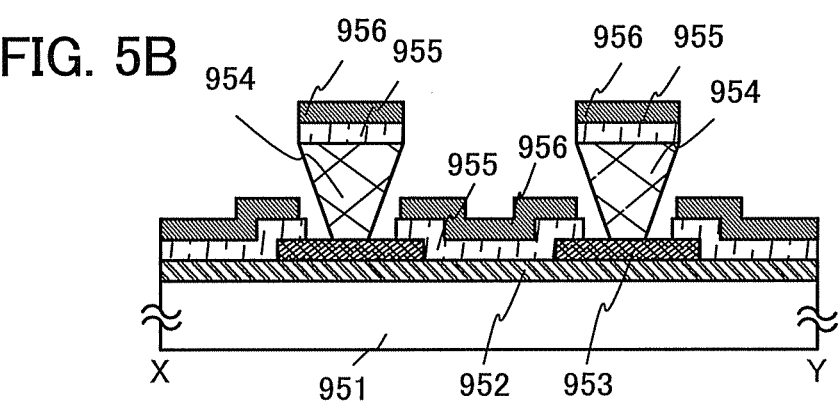

Although, as described above, an active matrix light-emitting device in which driving of a light-emitting element is controlled by transistors is described in this embodiment, the light-emitting device may also be a passive matrix light-emitting device. FIGS. 5A and 5B illustrate a passive matrix light-emitting device to which the present invention is applied. FIG. 5A is a perspective view of the light-emitting device, and FIG. 5B is a cross-sectional view taken along a line X-Y of FIG. 5A. In FIGS. 5A and 5B, a layer 955 containing a light-emitting substance is provided between an electrode 952 and an electrode 956 over a substrate 951. End portions of the electrode 952 are covered with an insulating layer 953. Then, a partition layer 954 is provided over the insulating layer 953. A sidewall of the partition layer 954 slopes so that the distance between one sidewall and the other sidewall becomes narrower toward the substrate surface. In other words, a cross section taken in the direction of the short side of the partition layer 954 is trapezoidal, and the base of the cross-section (a side facing in the same direction as a plane direction of the insulating layer 953 and in contact with the insulating layer 953) is shorter than the upper side thereof (a side facing in the same direction as the plane direction of the insulating layer 953 and not in contact with the insulating layer 953). The provision of the partition layer 954 in this manner can prevent the light-emitting element from being defective due to static electricity or the like.

The layer 955 containing a light-emitting substance of the passive matrix light-emitting device is formed by a wet process using any of the compositions of the present invention, which contains an anthracene derivative and a solvent, as described in Embodiment 1 or 2. In this embodiment, the layer 955 containing a light-emitting substance is formed by a coating method (a spin coating method). The partition layer 954 of the light-emitting device in FIGS. 5A and 5B has a so-called reverse-tapered shape. Therefore, the layer 955 containing a light-emitting substance is divided by the partition layer 954 in a self-aligned manner to be selectively formed over the electrode 952 even if the composition containing a light-emitting substance is applied by a coating method. Thus, adjacent light-emitting elements are divided without being processed by etching, resulting in prevention of electrical failure such as a short circuit between the light-emitting elements. Accordingly, the light-emitting device shown in FIGS. 5A and 5B can be manufactured in a more simplified step.

A thin film formed by a wet process with the use of any of the compositions of this embodiment, in which an anthracene derivative is dissolved in a solvent, can be made to a have favorable film quality without defects or the like. Thus, with the use of such a composition and a thin film, a highly reliable light-emitting element (device) can be manufactured.

In this embodiment, high material use efficiency can be achieved because a wet process is employed for manufacture of a thin film and a light-emitting element, and low cost and high productivity can be achieved because expensive facilities such as a large size vacuum apparatus can be reduced. Thus, by using the present invention, a light-emitting device and an electronic device that are highly reliable can be manufactured at low cost with high productivity.

(Embodiment 6)

In this embodiment, electronic devices of the present invention, each including the light-emitting device described in Embodiment 4, are described.

Examples of electronic devices that include light-emitting elements manufactured using any of the compositions of the present invention which has an anthracene derivative and a solvent include a camera such as a video camera or a digital camera, a goggle-type display, a navigation system, an audio reproducing device (such as a car audio component and an audio component), a computer, a game machine, a portable information terminal (such as a mobile computer, a cellular phone, a mobile game machine, and an electronic book), an image reproducing device provided with a recording medium (specifically, a device which reproduces contents of a recording medium such as a digital versatile disc (DVD) and has a display for displaying the reproduced image) and the like. Specific examples of these electronic devices are shown in FIGS. 6A to 6E.

Figure 6A:
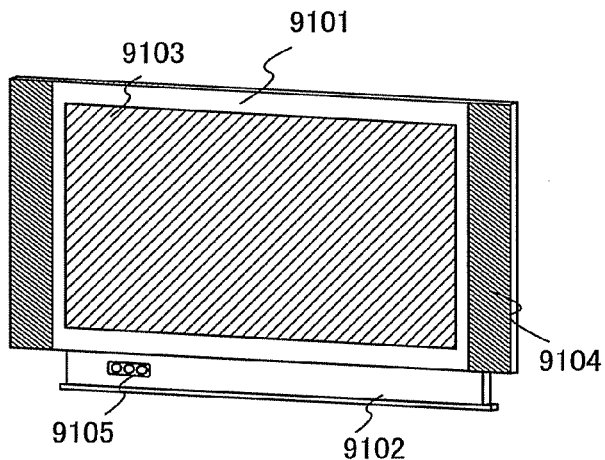
FIGS. 6A to 6E are views illustrating electronic devices.

FIG. 6A illustrates a television device according to the present invention which includes a housing 9101, a support stand 9102, a display portion 9103, a speaker portion 9104, a video input terminal 9105, and the like. In the television device, the display portion 9103 includes light-emitting elements similar to those described in Embodiment 2 or 3, which are arranged in matrix. Each light-emitting element is manufactured using any of the compositions described in Embodiment 1 or 2. Accordingly, lower cost and higher productivity can be achieved because of high material use efficiency and a reduction in expensive facilities such as a large vacuum apparatus. Thus, by using the present invention, a highly reliable television device can be provided at low cost. Furthermore, in the television device according to the present invention, the degree of freedom of the shape is high because the display portion is formed by a wet process; thus, products suitable for living environments can be provided.

Figure 6B:
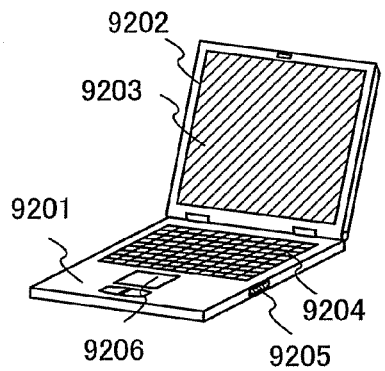

FIG. 6B illustrates a computer according to the present invention which includes a main body 9201, a housing 9202, a display portion 9203, a keyboard 9204, an external connection port 9205, a pointing device 9206, and the like. In the computer, the display portion 9203 includes light-emitting elements similar to those described in Embodiment 2 or 3, which are arranged in matrix. Each light-emitting element is manufactured using any of the compositions described in Embodiment 1 or 2. Accordingly, lower cost and higher productivity can be achieved because of high material use efficiency and a reduction in expensive facilities such as a large vacuum apparatus. Thus, by using the present invention, a highly reliable computer can be provided at low cost. Furthermore, in the computer according to the present invention, the degree of freedom of the shape is high because the display portion is formed by a wet process; thus, products suitable for the environment can be provided.

Figure 6C:
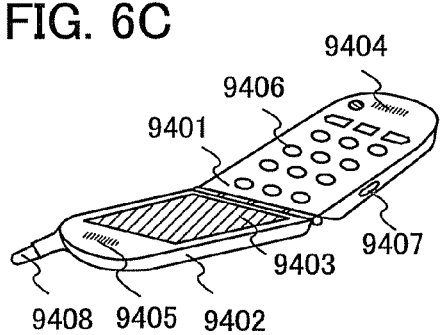

FIG. 6C illustrates a cellular phone according to the present invention which includes a main body 9401, a housing 9402, a display portion 9403, an audio input portion 9404, an audio output portion 9405, operation keys 9406, an external connection port 9407, an antenna 9408, and the like. In the cellular phone, the display portion 9403 includes light-emitting elements similar to those described in Embodiment 2 or 3, which are arranged in matrix. Each light-emitting element is manufactured using any of the compositions described in Embodiment 1 or 2. Accordingly, lower cost and higher productivity can be achieved because of high material use efficiency and a reduction in expensive facilities such as a large vacuum apparatus. Thus, by using the present invention, a highly reliable cellular phone can be provided at low cost.

Furthermore, in the cellular phone according to the present invention, the degree of freedom of the shape is high because the display portion is formed by a wet process; thus, products suitable for portability can be provided.

Figure 6D:
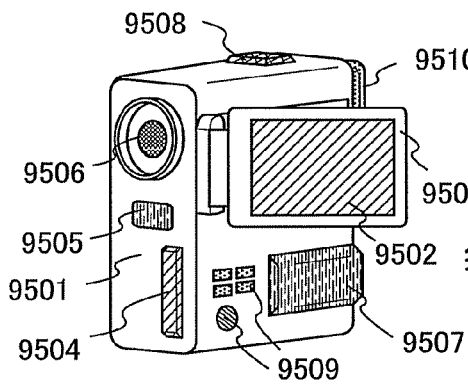

FIG. 6D illustrates a camera according to the present invention which includes a main body 9501, a display portion 9502, a housing 9503, an external connection port 9504, a remote control receiver 9505, an image receiver 9506, a battery 9507, an audio input portion 9508, operation keys 9509, an eye piece portion 9510, and the like. In the camera, the display portion 9502 has light-emitting elements similar to those described in Embodiment 2 or 3, which are arranged in matrix. Each light-emitting element is manufactured using any of the compositions described in Embodiment 1 or 2. Accordingly, lower cost and higher productivity can be achieved because of high material use efficiency and a reduction in expensive facilities such as a large vacuum apparatus. Thus, by using the present invention, a highly reliable camera can be provided at low cost. Furthermore, in the camera according to the present invention, the degree of freedom of the shape is high because the display portion is formed by a wet process; thus, products suitable for portability can be provided.

Figure 6E:
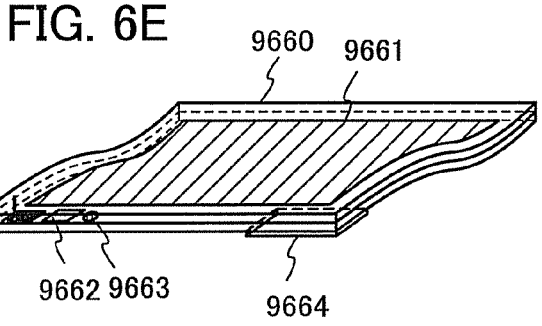

FIG. 6E illustrates electronic paper according to the present invention which is flexible and includes a main body 9660, a display portion 9661 which displays images, a driver IC 9662, a receiver 9663, a film battery 9664, and the like. The driver IC, the receiver, or the like may be mounted using a semiconductor component. In the electronic paper of the present invention, the main body 9660 is formed using a flexible material such as plastic or a film. In the electronic paper, the display portion 9611 has light-emitting elements similar to those described in Embodiment 2 or 3, which are arranged in matrix. Each light-emitting element is manufactured using any of the compositions described in Embodiment 1 or 2. Accordingly, lower cost and higher productivity can be achieved because of high material use efficiency and a reduction in expensive facilities such as a large vacuum apparatus. Thus, by using the present invention, a highly reliable electronic paper can be provided at low cost. Furthermore, in the electronic paper according to the present invention, the degree of freedom of the shape is high because the display portion is formed by a wet process; thus, products suitable for portability can be provided.

Furthermore, such electronic paper is extremely light and flexible and can be rolled into a cylinder shape as well; thus, the electronic paper is a display device that has a great advantage in terms of portability. The electronic device of the present invention allows a display medium having a large screen to be freely carried.

The electronic paper illustrated in FIG. 6E can be used as a display means of a navigation system, an audio reproducing device (such as a car audio or an audio component), a personal computer, a game machine, and a portable information terminal (such as a mobile computer, a cellular phone, a portable game machine, or an electronic book). Moreover, the display device can be used as a means for inainly displaying a still image for electrical home appliances such as a refrigerator, a washing machine, a rice cooker, a fixed telephone, a vacuum cleaner, or a clinical thermometer, railroad wall banners, and a large-sized information display such as an arrival and departure guide plate in a railroad station and an airport.

As described above, the applicable range of the light-emitting device of the present invention is so wide that the light-emitting device can be applied to electronic devices of a variety of fields. Since any of the compositions described in Embodiment 1 or 2 of the present invention is used, the material use efficiency is high and expensive facilities such as a large vacuum apparatus can be reduced. Accordingly, lower cost and higher productivity can be achieved. Therefore, by using the present invention, highly reliable electronic devices can be provided at low cost.

The light-emitting device of the present invention can also be used as a lighting apparatus. One mode using the light-emitting element of the present invention for the lighting apparatus is described with reference to FIG. 7.

Figure 7:
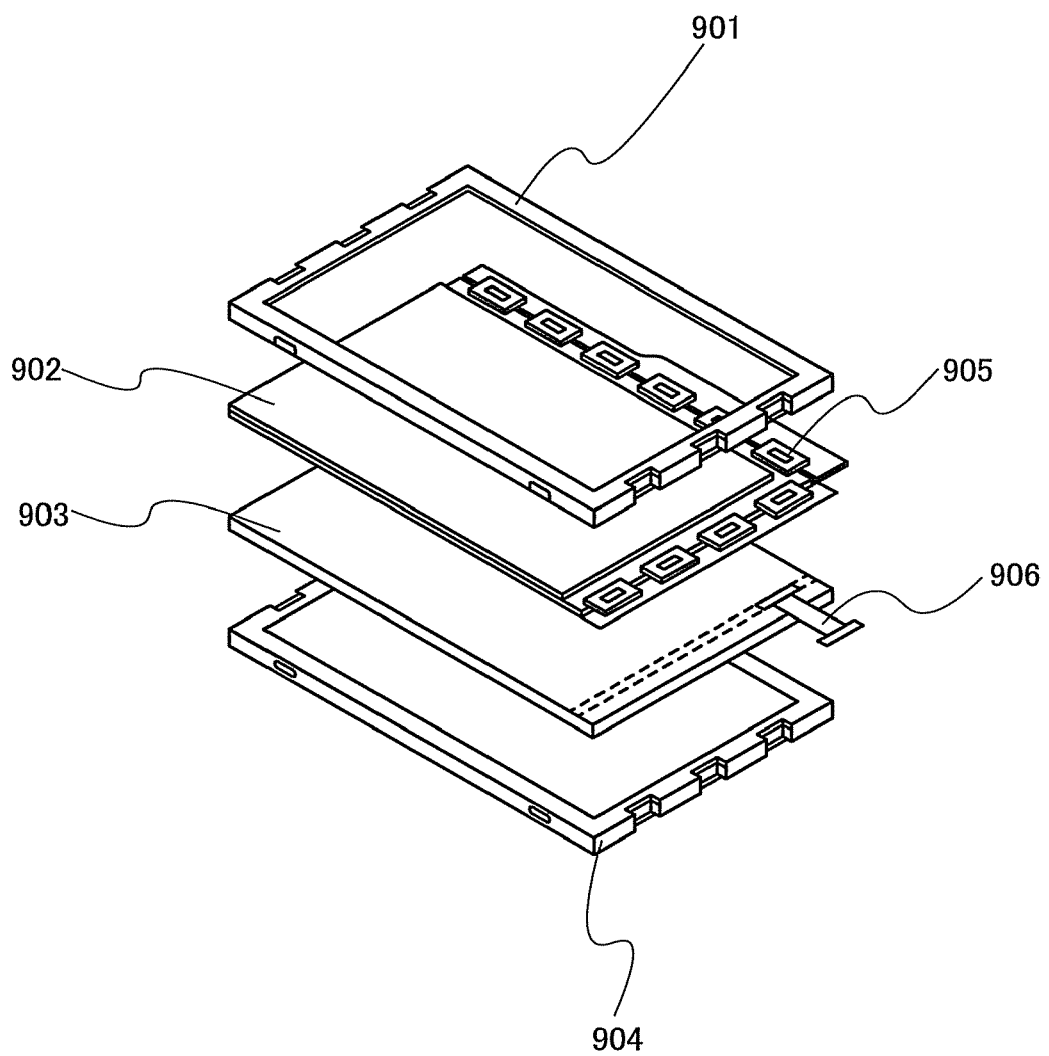
FIG. 7 is a view illustrating an electronic device.

FIG. 7 illustrates an example of a liquid crystal display device in which the light-emitting device of the present invention is used as a backlight. The liquid crystal display device illustrated in FIG. 7 includes a housing 901, a liquid crystal layer 902, a backlight 903, and a housing 904. The liquid crystal layer 902 is connected to a driver IC 905. The light-emitting device of the present invention is used as the backlight 903, and current is supplied through a terminal 906.

By use of the light-emitting device of the present invention as the backlight of the liquid crystal display device, lower cost and higher productivity can be achieved. Further, since the light-emitting device of the present invention is a lighting apparatus with plane light emission and can be made to have a larger area, the backlight can be made to have a larger area, and a liquid crystal display device can also be made to have a larger area. Furthermore, since the light-emitting device of the present invention is thin, a display device can be made thin.

Figure 8A:
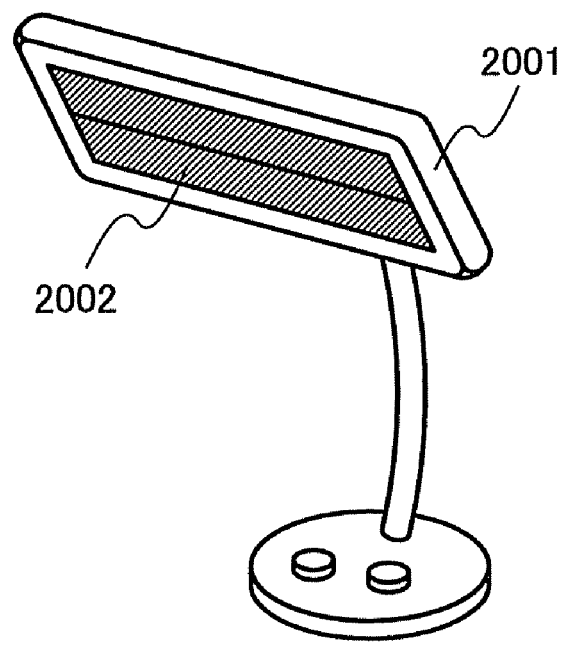
FIGS. 8A and 8B are views each illustrating a lighting apparatus.
Figure 8B:
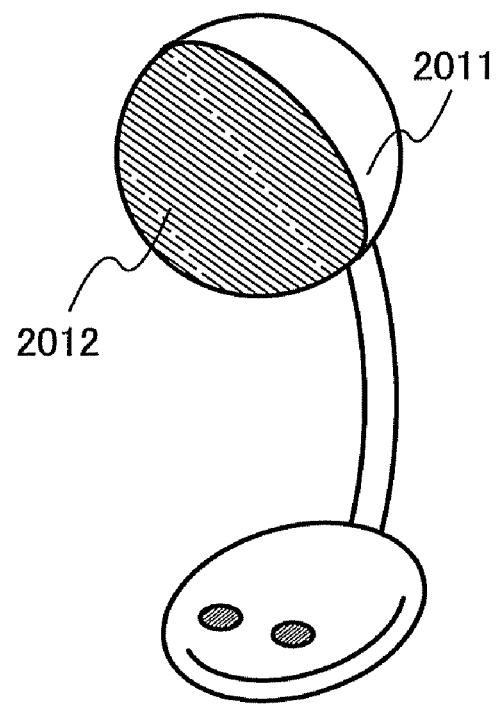

Each of FIGS. 8A and 8B illustrates an example in which the light-emitting device of the present invention is used as a table lamp that is a lighting apparatus. A table lamp illustrated in FIG. 8A has a housing 2001 and a light source 2002, and the light-emitting device of the present invention is used as the light source 2002. A table lamp illustrated in FIG. 8B has a housing 2011 and a light source 2012, and the light-emitting device of the present invention is used as the light source 2012. In the present invention, a thin film containing a light-emitting substance is formed by a wet process and therefore can be formed even on a curved surface, such as the surface of the light source 2012. Accordingly, by using the present invention, the shape and design of the light-emitting device of the present invention which can be manufactured can freely be set.

Figure 9:
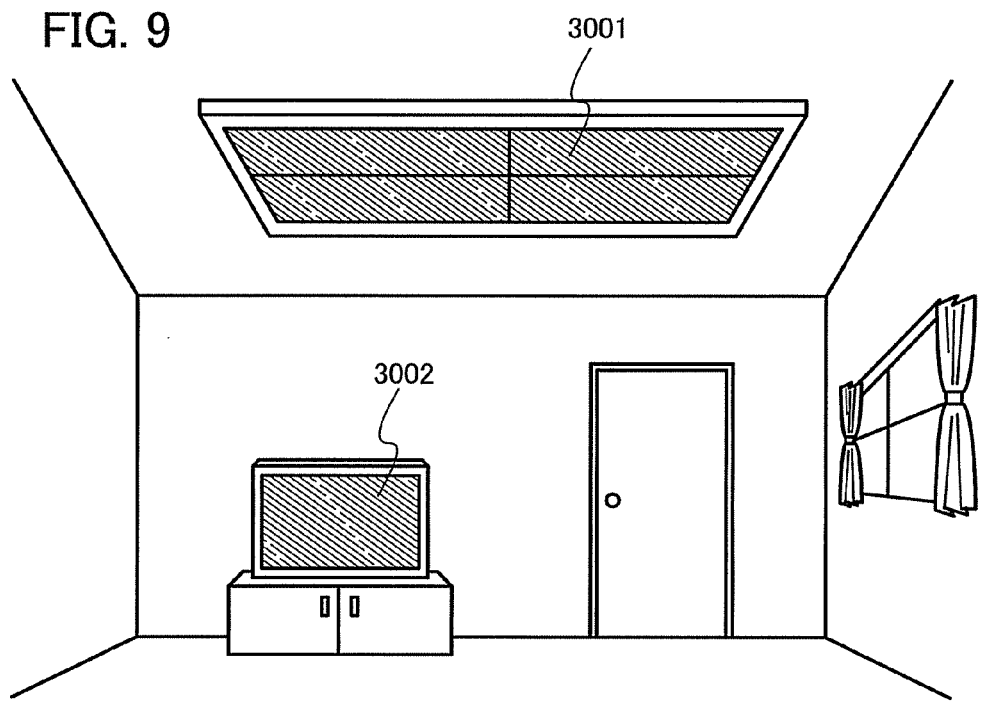
FIG. 9 is a view illustrating a lighting apparatus.

FIG. 9 illustrates an example in which a light-emitting device to which the present invention is applied is used as an indoor lighting apparatus 3001. Since the light-emitting device of the present invention can be made to have a larger area, the light-emitting device of the present invention can be used as a lighting apparatus having a large emission area. Further, since the light-emitting device of the present invention is thin, the light-emitting device of the present invention can be used as a lighting apparatus with a thinner shape. A television device 3002 according to the present invention as described in FIG. 6A is placed in a room in which a light-emitting device to which the present invention is applied is used as the indoor lighting apparatus 3001, and public broadcasting and movies can be enjoyed.

EXAMPLE 1

In this example, the solubility of any of the compositions of the present invention which has an anthracene derivative and a solvent and the film quality such as the thickness of a thin film formed using the composition by a wet process or uniformity of properties thereof were evaluated.

As comparative examples, compositions were produced by dissolving samples 1-1 to 1-4 in solvents. As manufacturing examples 1, compositions were produced by dissolving samples 1-5 to 1-14 in solvents. The solubility test was performed on the solvents of the anthracene derivatives of the samples 1-5 to 1-15. The following six solvents were used: diethyl ether, toluene, ethyl acetate, anisole, acetone, and 1,4-dioxane.

As the anthracene derivatives of the sample 1-1, the sample 1-2, the sample 1-3, and the sample 1-4 used in the comparative examples, 9,10-diphenylanthracene (abbr.: DPAnth), 9,10-bis(4-(N-carbazolylphenyl)anthracene (abbr.: CzBPAII), 9-phenyl-9'-[4-(10-phenyl-9-anthryl)phenyl]-3,3'-bi (9H-carbazole) (abbr.: PCCPA), and 3,3'-(2-tert-buthylanthracene-9,10'-diyldi-4,1-phenylene)bis(9-phenyl-9H-carbazole) (abbr.: PCzBPA) were used, respectively.

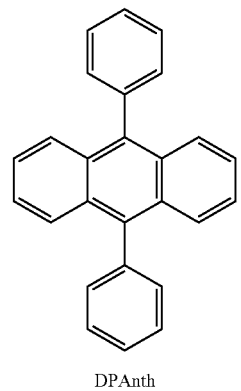

DPAnth

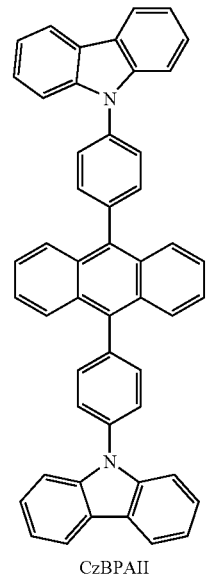

CzBPAII

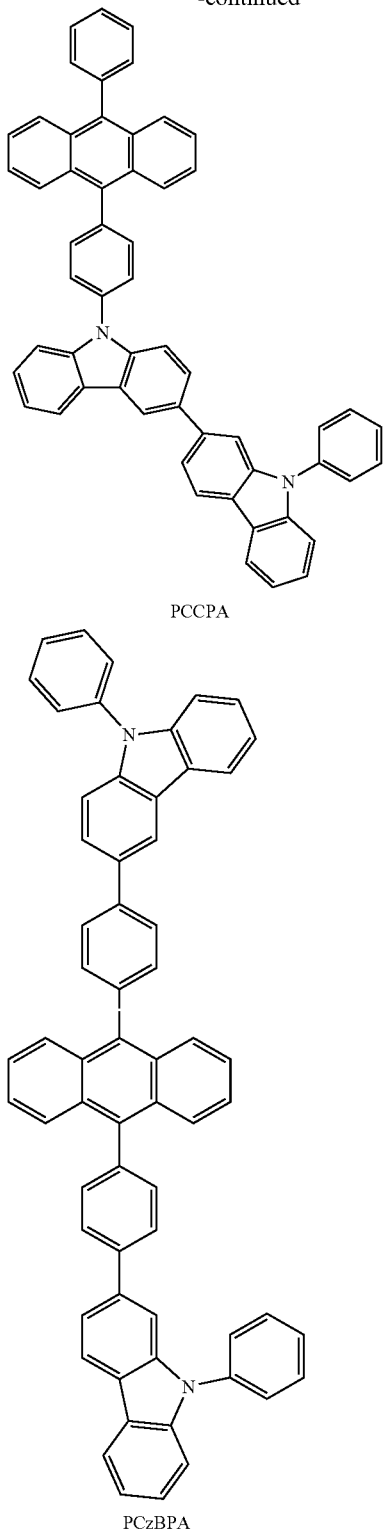

PCCPA

PCzBPA

As the anthracene derivatives of the sample 1-5, the sample 1-6, the sample 1-7, the sample 1-8, the sample 1-9, the sample 1-10, the sample 1-11, the sample 1-12, the sample 1-13, and the sample 1-14 used in the manufacturing examples 1, 9-[4-(N-carbazolyl)]phenyl-10-phenylanthracene (abbr.: CzPA), 9-phenyl-3-[4-(10-phenyl-9-anthryl)phenyl]-9H-carbazol (abbr.: PCzPA), 9-[3-(10-phenyl-9-anthryl)phenyl]-9H-carbazole (abbr.: mCzPA), 9-(4-tert-butylphenyl)-10-[4-(carbazol-9-yl)]phenylanthracene (abbr.: PTBCzPA), 9-[4-(carbazol-9-yl)phenyl]-10-(2-naphthyl)anthracene (abbr.: PNCZPA), 3,6-diphenyl-9-[4-(10-phenyl-9-antryl)phenyl]-9H-carbazole (abbr.: DPCzPA), 9-[4-(9,10-diphenyl-2-anthryl)phenyl]-9H-carbazole (abbr.: 2CzPPA), 9-(9,10-diphenyl-2-anthryl)-9H-carbazole (abbr.: 2CzPA), 3-(9,10-diphenyl-2-anthryl)-9-phenyl-9H-carbazole (abbr.: 2PCzPA), 9-[9,10-bis(2-biphenyl)-2-anthryl]-9H-carbazole (abbr.: 2CzBPhA) were used, respectively.

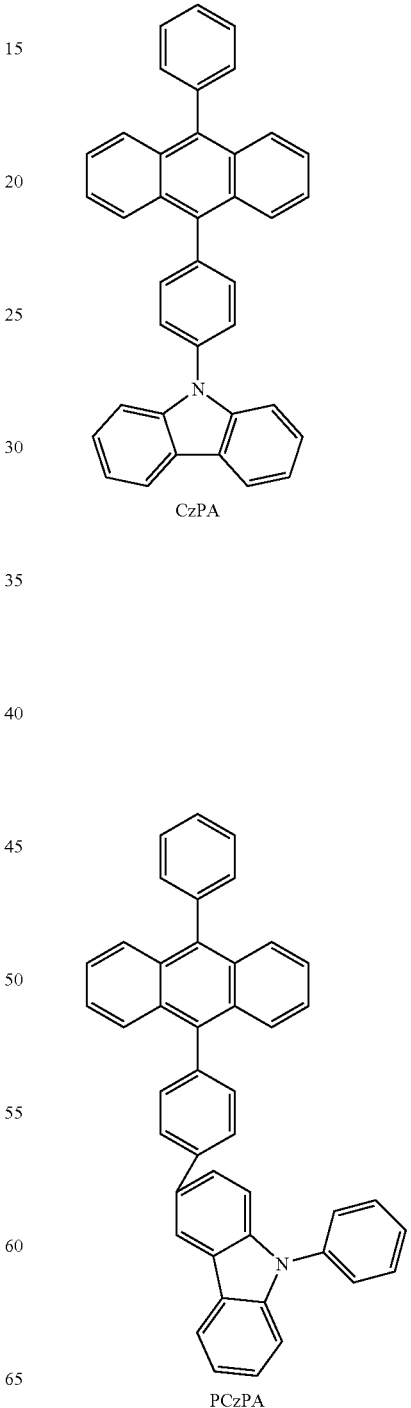

CzPA

PCzPA

-continued
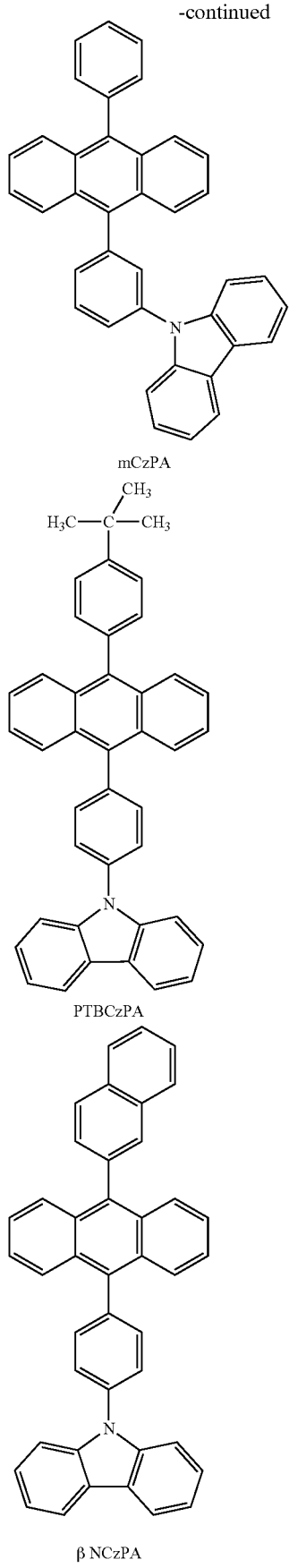
mCzPA
PTBCzPA
β NCzPA
-continued
DPCzPA
2CzPPA

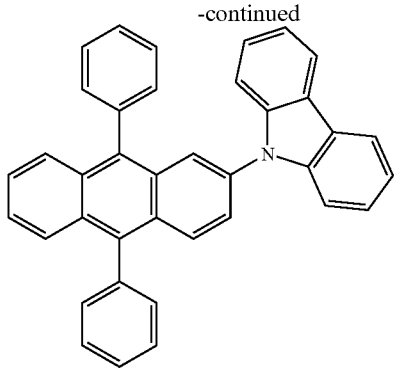

2CzPA

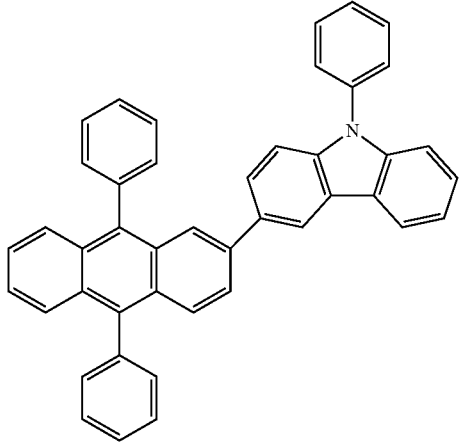

2PCzPA

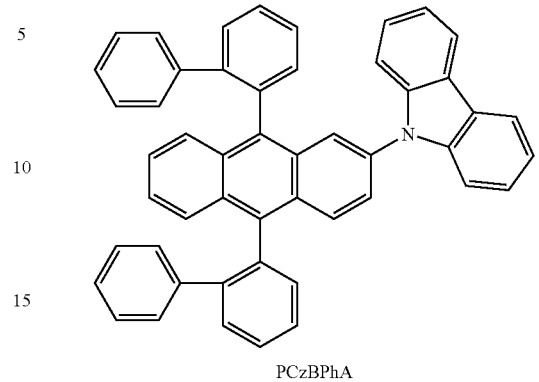

PCzBPhA 0.01 g of each of the anthracene derivatives of the samples 1-1 to 1-14 was measured and put in a sample bottle, 1 mL of a solvent was added in the sample bottle (the solution concentration was 10 g/L), and ultrasonic waves were applied thereto for 10 minutes. Table 1 shows the results of the solubility test on the obtained compositions having the samples 1-1 to 1-14, in which a circle is marked when the anthracene derivative is completely dissolved, and a cross is marked when some amount of the anthracene derivative remained undissolved, turbidity was caused, or the anthracene derivative was suspended.

TABLE 1

| Solubility Test | | | Solvent | | | | | |
|---|---|---|---|---|---|---|---|---|
| | Name of Samples | Abbreviation | Diethyl ether | Toluene | Ethyl acetate | Anisole | acetone | dioxane |
| Comparative Examples | Sample 1-1 | DPAnth | X | ○ | X | ○ | X | X |
| | Sample 1-2 | CzBPAII | X | X | X | X | X | X |
| | Sample 1-3 | PCCPA | X | X | X | X | X | X |
| | Sample 1-4 | PCzBPA | X | X | X | X | X | X |
| Manufacturing Examples 1 | Sample 1-5 | CzPA | X | ○ | X | ○ | X | X |
| | Sample 1-6 | PCzPA | X | ○ | X | ○ | X | ○ |
| | Sample 1-7 | m-CzPA | X | ○ | X | ○ | X | ○ |
| | Sample 1-8 | PTBCzPA | X | ○ | X | ○ | X | X |
| | Sample 1-9 | βNCzPA | X | ○ | X | ○ | X | ○ |
| | Sample 1-10 | DPCzPA | X | ○ | X | ○ | X | ○ |
| | Sample 1-11 | 2CzPPA | — | ○ | X | ○ | X | ○ |
| | Sample 1-12 | 2CzPA | ○ | ○ | ○ | ○ | X | ○ |
| | Sample 1-13 | 2PCzPA | — | ○ | ○ | ○ | ○ | ○ |
| | Sample 1-14 | 2CzBPhA | X | ○ | ○ | ○ | ○ | ○ |

Like the samples 1-2 to 1-4 (CzBPA2, PCCPA, and PCzBPA) of the comparative examples, anthracene derivatives each having two carbazolyl groups have a low solubility in a solvent. Like the samples 1-5 to 1-14 of the manufacturing examples 1, anthracene derivatives having one anthracene structure and one carbazolyl group which is bonded to the anthracene structure directly or through a phenyl group have a high solubility in a solvent. Further, it is found that the anthracene derivatives, such as the samples 1-12 to 1-14 of the manufacturing examples 1, each having one anthracene structure and one carbazolyl group which is directly bonded to the anthracene structure can be dissolved in more solvents and have an especially high solubility.

Next, solvents in which the anthracene derivative has a high solubility in the solubility test were selected and a film quality test was performed. That is, a film quality test was performed on the samples 1-1 and 1-5 to 1-14 other than the samples 1-2 to 1-4 which did not have high solubility in any solvent in the solubility test. A composition of each of the samples was adjusted at a concentration of 10 g/L which is the same as that of the solubility test and was deposited over a glass substrate with a size of 5 inches at 1000 rpm (60 seconds) with a spin coater. Table 2 shows the results of the film quality test in which a circle is marked in the case of a transparent film where crystallization or white turbidity is not seen and a cross is marked in the case of a film where crystallization or white turbidity is seen.

TABLE 2

| Film Quality Test | | Solvent | | | |
|---|---|---|---|---|---|
| Name of Samples | Abbreviation | Toluene | Ethyl acetate | Anisole | dioxane |
| Comparative Example Sample 1-1 | DPAnth | X | X | X | X |
| Manufacturing Example 1 Sample 1-5 | CzPA | ○ | X | ○ | X |
| Sample 1-6 | PCzPA | ○ | X | ○ | X |
| Sample 1-7 | m-CzPA | ○ | X | ○ | ○ |
| Sample 1-8 | PTBCzPA | ○ | X | ○ | X |
| Sample 1-9 | βNCzPA | ○ | X | ○ | X |
| Sample 1-10 | DPCzPA | ○ | X | ○ | X |
| Sample 1-11 | 2CzPPA | ○ | X | ○ | X |
| Sample 1-12 | 2CzPA | ○ | ○ | ○ | X |
| Sample 1-13 | 2PCzPA | ○ | ○ | ○ | X |
| Sample 1-14 | 2CzPBPhA | ○ | ○ | ○ | X |

A film containing the sample 1-1 (DPAnth) of the comparative example, which has high solubility in a solvent in the solubility test, was a crystallized film with a bad quality in the film quality test. On the other hand, it was confirmed that each of the films containing the samples 1-5 to 1-14 of the manufacturing examples was a film with a good quality and a favorable shape.

Accordingly, it was confirmed that any of the compositions of the present invention which has an anthracene derivative and a solvent is a composition in which the anthracene derivative has high solubility and a uniform thin film with a favorable film quality can be formed by a wet process using the compositions.

EXAMPLE 2

Figure 12:
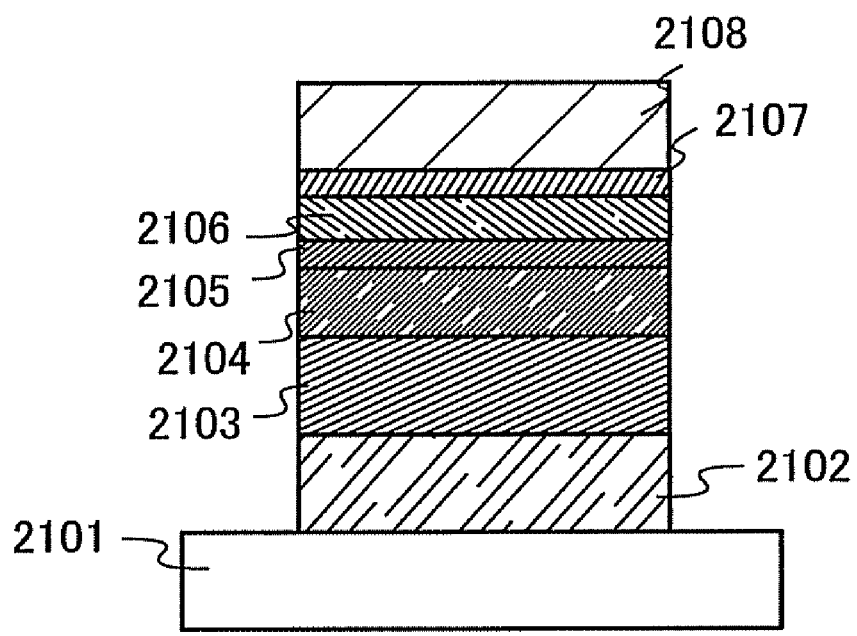
FIG. 12 is a view illustrating light-emitting elements A to E in Example 2.

In this example, light-emitting elements A to E of the present invention are described with reference to FIG. 12.

The element structures of the light-emitting elements A to E manufactured in this example are shown in Table 3. In Table 3, each mixture ratio is indicated by weight ratio.

TABLE 3

| | First Electrode 2102 | First Layer 2103 | Second Layer 2104 | Third Layer 2105 | Fourth Layer 2106 | Fifth Layer 2107 | Second Electrode 2108 |
|---|---|---|---|---|---|---|---|
| Light-emitting Element A | ITSO 110 nm | PEDOT:PSS 50 nm | CzPA:2PCAPA(=1:0.2) 50 nm | Alq 10 nm | Bphen 20 nm | LiF 1 nm | Al 200 nm |
| Light-emitting Element B | ITSO 110 nm | PEDOT:PSS 50 nm | 2CzPPA:2PCAPA(=1:0.2) 50 nm | Alq 10 nm | Bphen 20 nm | LiF 1 nm | Al 200 nm |
| Light-emitting Element C | ITSO 110 nm | PEDOT:PSS 50 nm | 2PCzPA:2PCAPA(=1:0.2) 50 nm | Alq 10 nm | Bphen 20 nm | LiF 1 nm | Al 200 nm |
| Light-emitting Element D | ITSO 110 nm | PEDOT:PSS 50 nm | 2CzPA:2PCAPA(=1:0.2) 50 nm | Alq 10 nm | Bphen 20 nm | LiF 1 nm | Al 200 nm |
| Light-emitting Element E | ITSO 110 nm | MoOx 20 nm | 2PCzPA:2CzPA:coumarin 6 (=0.5:0.5:0.023) 55 nm | Alq 10 nm | Bphen 20 nm | LiF 1 nm | Al 200 nm |

*Each mixture ratio is indicated by weight ratio

Hereinafter, a method for manufacturing the light emitting elements A to E of this example is described.

In the light-emitting elements A to B, a film of an indium tin oxide containing silicon oxide (ITSO) was formed over a glass substrate 2101 by a sputtering method, whereby a first electrode 2102 was formed. Note that the thickness thereof was 110 nm and the electrode area was 2 mm×2 mm.

Next, a first layer 2103 was formed. As a solution used for a pretreatment for forming the light-emitting elements A to D, Solution C in which water and 2-methoxyethanol were mixed at a ratio of 3:2 and Solution D in which an undiluted solution of PEDOT:PSS (BAYTRON P AI4083 LVW 142) and 2-methoxyethanol were mixed at a rate of 3:2 were prepared. Solution C was dripped onto the substrate on which the first electrode 2102 was formed. After being spin-coated with Solution C at a spinning rate of 2000 rpm for 20 seconds, the substrate was spin-coated with Solution D at a spinning rate of 2000 rpm for 60 seconds and then at a spinning rate of 2500 rpm for 10 seconds. The film formed by the spin coating of Solution D on a terminal portion was removed using ethanol, and drying was performed by heating for 2 hours in a vacuum oven in which the temperature was set at 110° C. while the pressure was reduced with a rotary pump, whereby a PEDOT/PSS film with a thickness of 50 nm was formed as the first layer 2103.

In the light-emitting element B, molybdenum oxide was vacuum evaporated to form a film having a thickness of 20 nm as the first layer 2103.

In the light-emitting element A, as a solution used for forming a second layer 2104 which serves as a layer containing a light-emitting substance, 0.15 g of an anthracene derivative (0.15 g of CzPA in the light-emitting element A, 0.15 g of 2CzPPA in the light-emitting element B, 0.15 g of 2PCzPA in the light-emitting element C, and 0.15 g of 2CzPA in the light-emitting element D) and 0.031 g of 2PCAPA were measured and put in a sample bottle. Into this bottle, 15 mL of dehydrated toluene (product of Kanto Chemical Co., Inc.) was added under an environment of low moisture concentration (less than 0.1 ppm) and low oxygen concentration (less than or equal to 10 ppm), and the sample bottle was stirred overnight with the lid closed, whereby each solution for forming the second layer 2104 which serves as a layer containing a light-emitting substance was prepared.

In the light-emitting element B, for a solution used for forming the second layer 2104 which serves as a layer containing a light-emitting substance, 0.085 g of 2PCzPA and 0.083 g of 2CzPA as anthracene derivatives and 0.004 g of coumarin 6 as a light-emitting substance were measured and 17 mL of dehydrate ethyl acetate (product of Kanto Chemical Co., Inc.) was used as a solvent.

Each solution for forming the second layer 2104 which serves as a layer containing a light-emitting substance was dropped onto the substrate over which the first layer 2103 was formed, under an environment of a low moisture concentration (less than 0.1 ppm) and a low oxygen concentration (less than or equal to 10 ppm). The substrate was spin-coated at a spinning rate of 300 rpm for 3 seconds, at a spinning rate of 1000 rpm for 60 seconds, and then at a spinning rate of 2500 rpm for 10 seconds. The film formed by the spin coating of each solution on a terminal portion was removed using toluene, and drying was performed by heating for one hour in a vacuum oven in which the temperature was set at 110° C. while the pressure was reduced with a rotary pump, whereby the second layer 2104 was formed. After that, the substrate was disposed in a vacuum evaporation apparatus in which the pressure was reduced so that a surface on which the film was to be formed faced downward.

An Alq film was formed over the second layer 2104 to a thickness of 10 nm as a third layer 2105 which is to serve as an electron-transporting layer.

Similarly, a Bphen film was deposited over the third layer 2105 to a thickness of 20 nm as a fourth layer 2106 which serves as an electron-transporting layer. Further, lithium fluoride (LiF) was evaporated over the fourth layer 2106 to a thickness of 1 nm, whereby a fifth layer 2107 was formed as an electron-injecting layer. Lastly, as a second electrode 2108 which serves as a cathode, aluminum was deposited to a thickness of 200 nm, and thus the light-emitting elements A to E of this example were obtained. Note that in the above evaporation process, evaporation was all performed by a resistance heating method. Further, structural formulae of Alq, 2PCAPA, and Bphen are shown below.

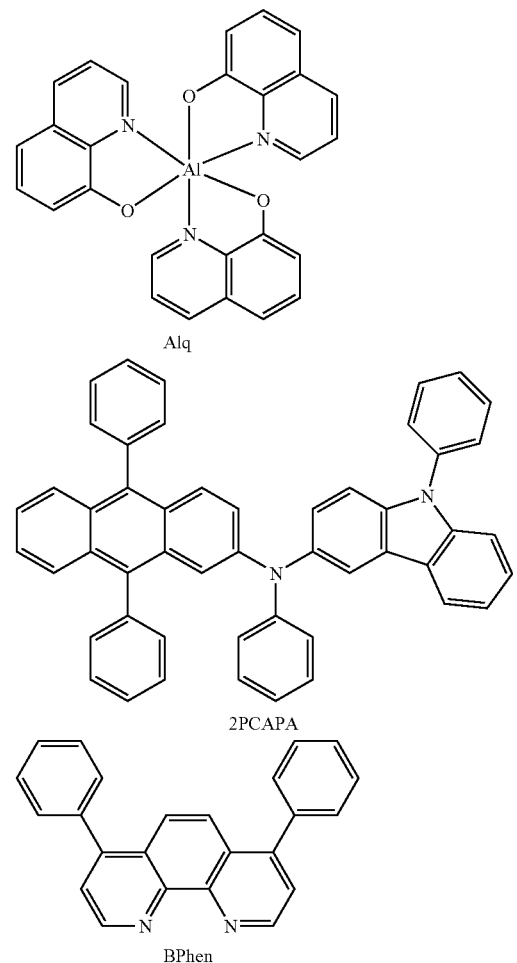

After the light-emitting elements A to E thus obtained were sealed in a glove box under a nitrogen atmosphere without being exposed to atmospheric air, the operating characteristics of the light-emitting elements were measured. Note that the measurement was carried out at room temperature (in the atmosphere kept at 25° C.).

Figure 13:
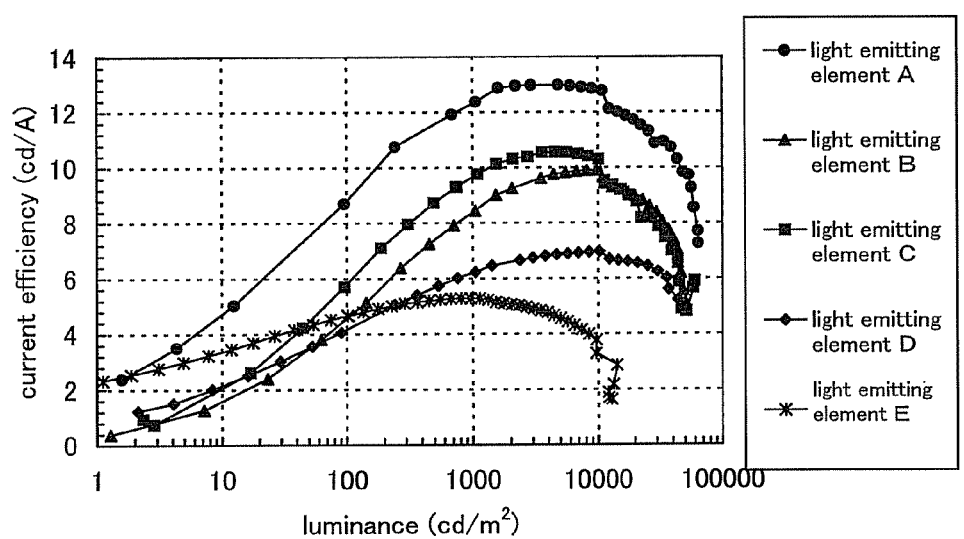
FIG. 13 is a graph showing luminance-current efficiency characteristics of the light emitting elements A to E in Example 2.
Figure 14:
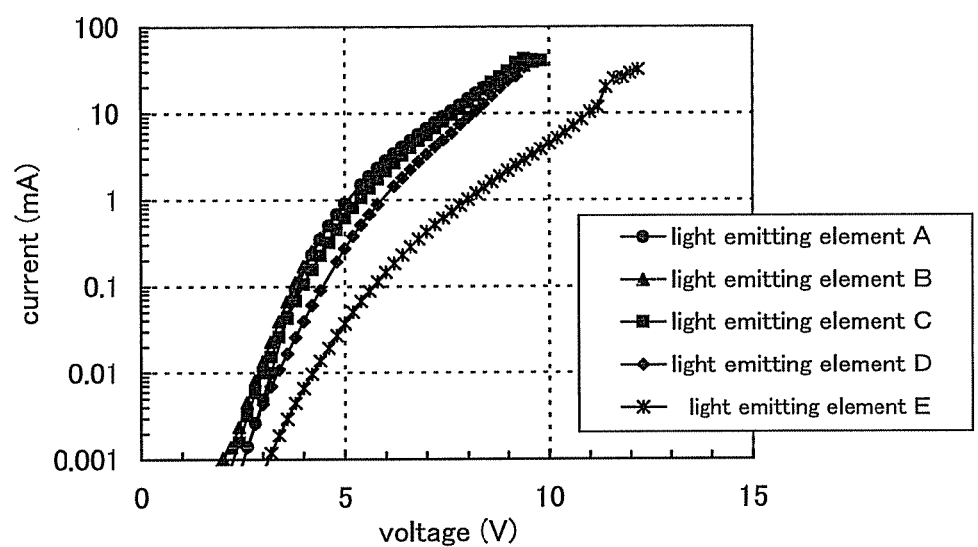
FIG. 14 is a graph showing current-voltage characteristics of the light emitting elements A to E in Example 2.
Figure 15:
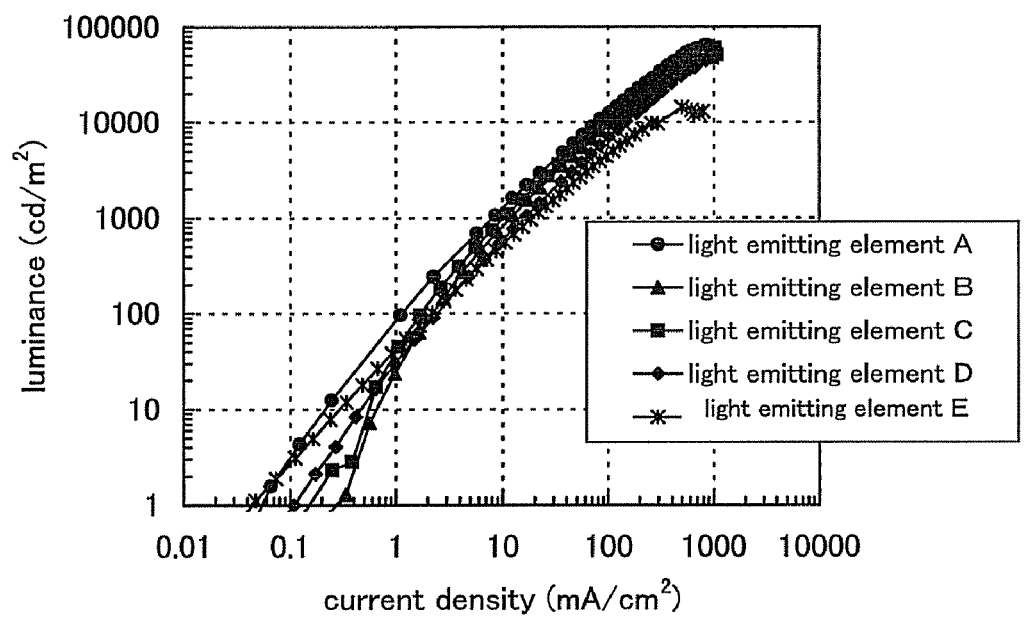
FIG. 15 is a graph showing current density-luminance characteristics of the light emitting elements A to E in Example 2.
Figure 16:
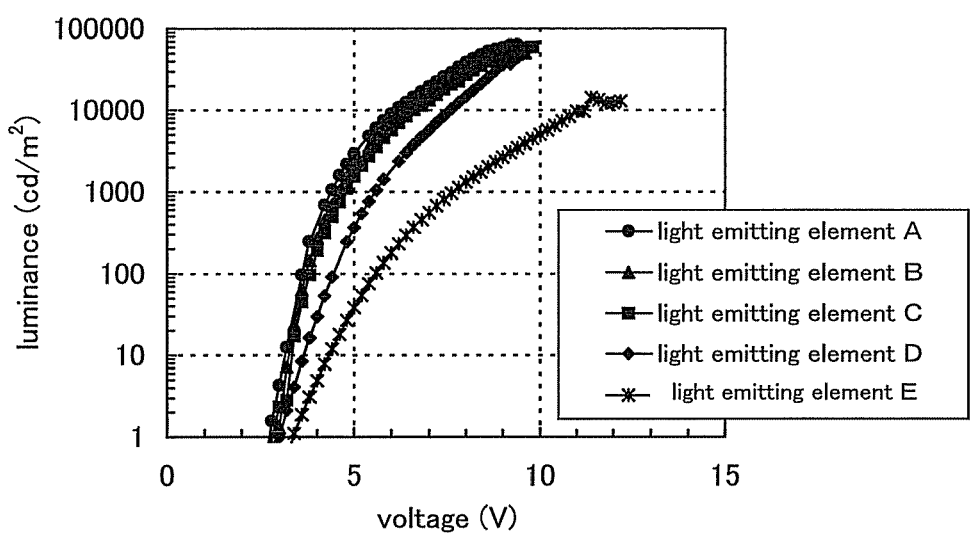
FIG. 16 is a graph showing voltage-luminance characteristics of the light emitting elements A to E in Example 2.
Figure 17A:
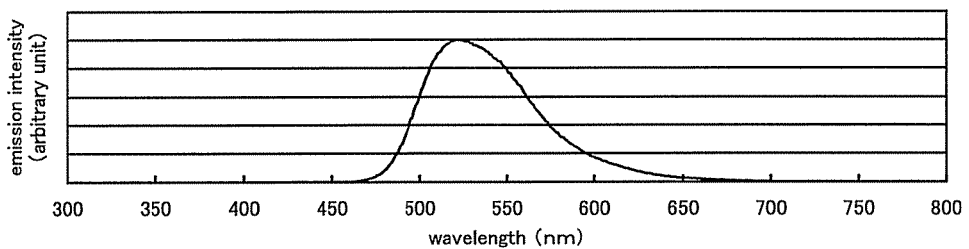
FIGS. 17A to 17E are graphs showing emission spectra of the light emitting elements A to E in Example 2.
Figure 17B:
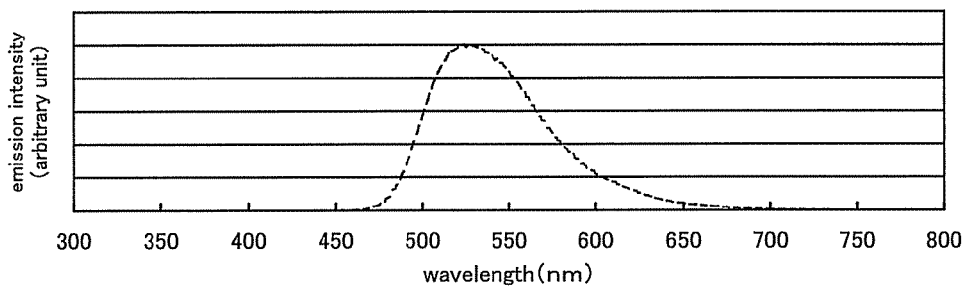
Figure 17C:
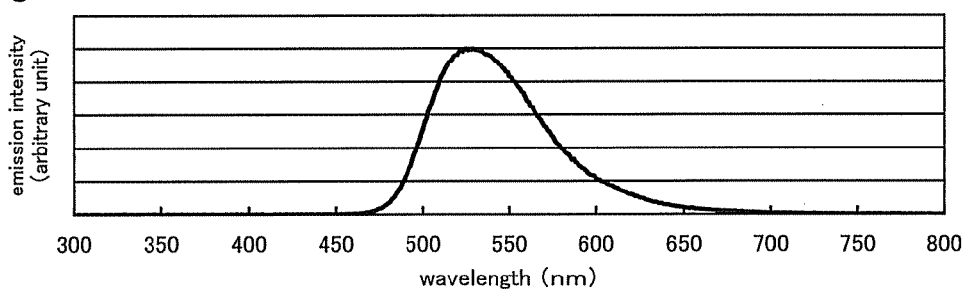
Figure 17D:
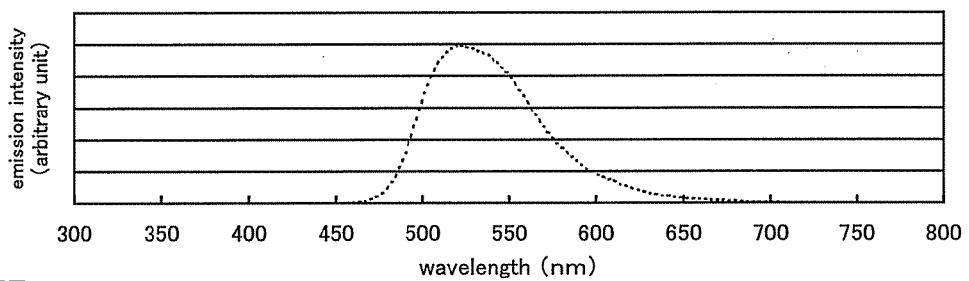
Figure 17E:
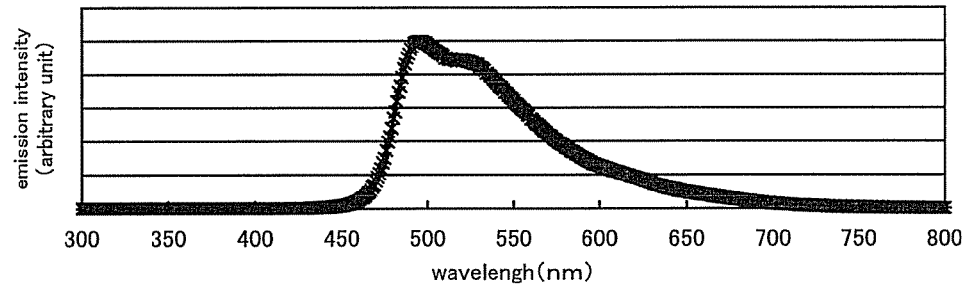

FIG. 13 shows luminance-current efficiency characteristics of the light-emitting elements A to E, FIG. 14 shows current-voltage characteristics thereof, FIG. 15 shows current density-luminance characteristics thereof and FIG. 16 shows voltage-luminance characteristics thereof. Further, FIGS. 17A to 17E show emission spectra of the light emitting elements A to E measured at a current of 1 mA, respectively.

Figure 18A:
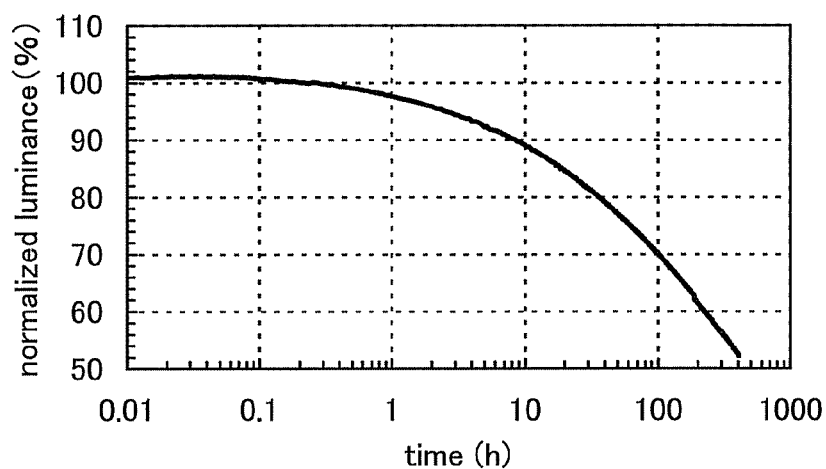
FIGS. 18A and 18B are graphs showing results of reliability test of the light emitting element A in Example 2.
Figure 18B:
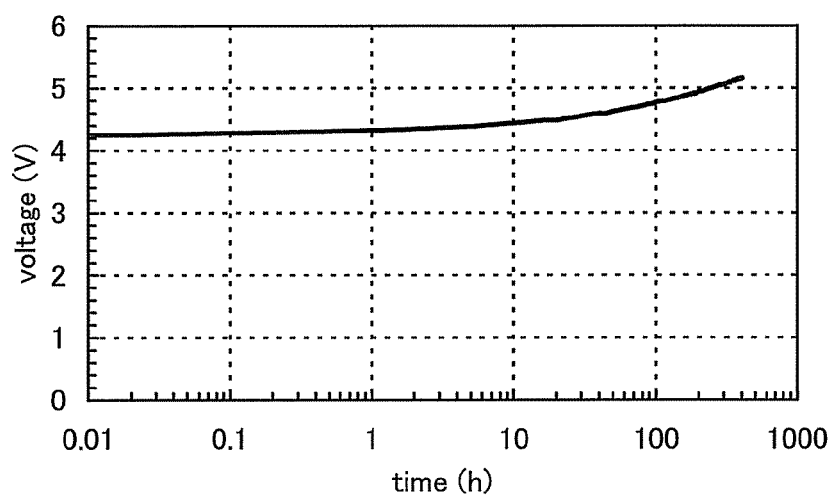
Figure 19A:
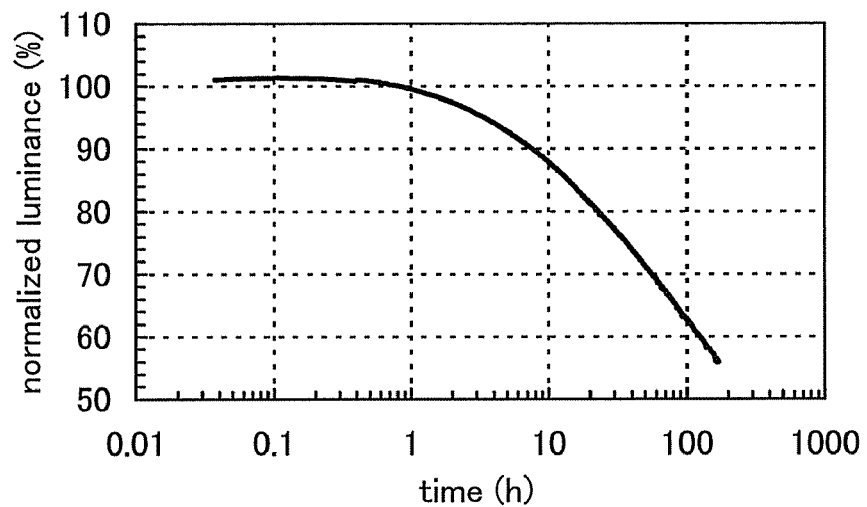
FIGS. 19A and 19B are graphs showing results of reliability test of the light-emitting element D in Example 2.
Figure 19B:
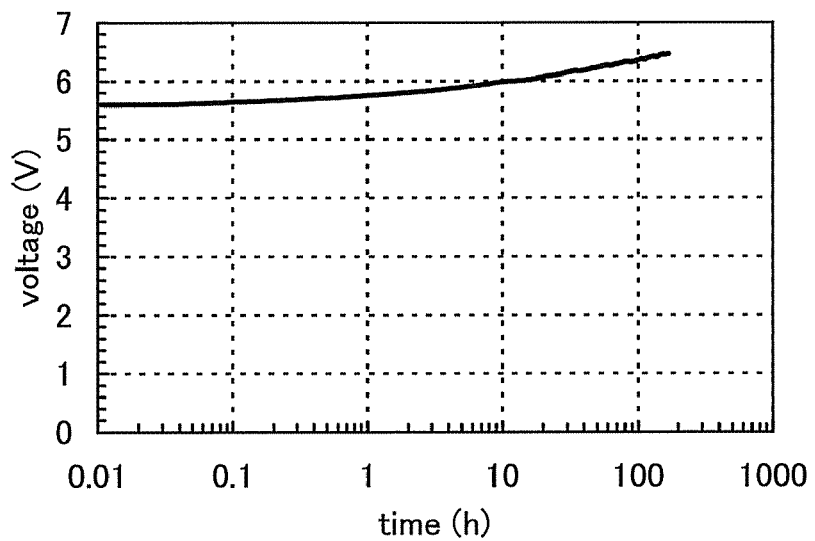

Further, a reliability test was performed on each of the manufactured light-emitting elements A and D as follows: the luminance was measured after every certain period of time passes while a current having the same value as the current which flows through the light-emitting elements A and D when the light-emitting elements A and D are made to emit light with a luminance of 1000 cd/m² in an initial state was continued to be made flow. FIGS. 18A and 18B show the results obtained by the reliability test of the light-emitting element A and FIGS. 19A and 19B show the results obtained by the reliability test of the light-emitting element D. FIG. 18A and FIG. 19A show a change in luminance over time, and FIG. 18B and FIG. 19B show a change in voltage over time. Note that in each of FIG. 18A and FIG. 19A, the horizontal axis represents current flow time (hour) and the vertical axis represents the proportion of luminance with respect to the initial luminance at each time, that is, normalized luminance (%). Further, in each of FIG. 18B and FIG. 19B, the horizontal axis represents current flow time (hour), and the vertical axis represents voltage.

According to this example, it was confirmed that the light-emitting element of the present invention has the characteristics as a light-emitting element and fully functions. Further, from the results of the reliability test, it was found that a highly reliable light-emitting element was obtained in which a short circuit due to defects of the film or the like is not caused even if the light-emitting element is made to emit light continuously.

EXAMPLE 3

9-phenyl-9'-[4-(10-phenyl-9-anthryl)phenyl]-3,3'-bi(9H-carbazole) abbn: PCCPA), 3,3'-(2-tert-butylanthracene-9,10'-diyldi-4,1-phenylene)bis(9-phenyl-9H-carbazole) (abbr.: PCzBPA), 9-phenyl-3-[4-(10-phenyl-9-anthryl)phenyl]-9H-carbazol (abbr.: PCzPA), 9-[3-(10-phenyl-9-anthryl)phenyl]-9H-carbazole (abbr.: mCzPA), 9-[4-(9,10-diphenyl-2-anthryl)phenyl]-9H-carbazole (abbr.: 2CzPPA), 9-(9,10-diphenyl-2-anthryl)-9H-carbazole (abbr.: 2CzPA), 3-(9,10-diphenyl-2-anthryl)-9-phenyl-9H-carbazole (abbr.: 2PCzPA), and 9-[9,10-bis(2-biphenyl)-2-anthryl]-9H-carbazole (abbr.: 2CzBPhA), which were used in Example 1, are novel materials or materials the synthesis methods of which are not disclosed; therefore, the synthesis methods thereof are described below.

SYNTHESIS EXAMPLE 1

A synthesis method of 9-phenyl-9'-[4-(10-phenyl-9-anthryl)phenyl]-3,3'-bi(9H-carbazole) (abbr.: PCCPA), which was used in Example 1, is described.

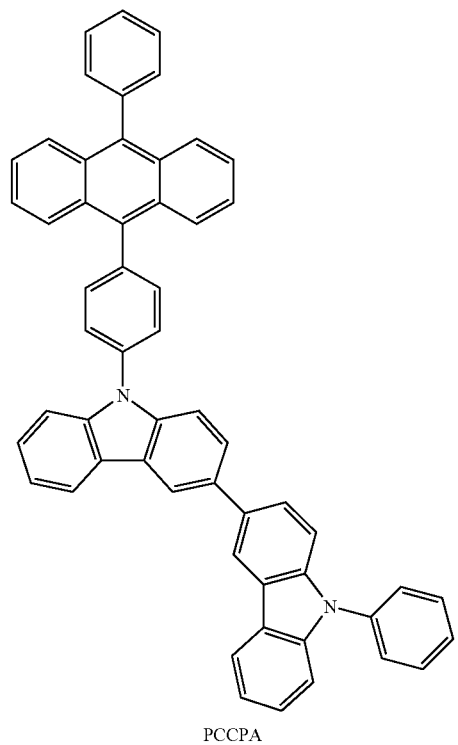

PCCPA

[Step 1] Synthesis of 9-phenyl-3,3'-bi(9H-carbazole) (abbr.: PCC)

Into a 200 mL three-neck flask were put 2.5 g (10 mmol) of 3-bromocarbazole, 2.9 g (10 mmol) of N-phenyl-9H-carbazol-3-boronic acid, and 152 ing (0.50 mmol) of tri(ortho-tolyl)phosphine. The air in the flask was replaced with nitrogen. 50 mL of ethylene glycol dimethyl ether and 10 mL of potassium carbonate solution (2 mol/L) were added to the mixture. This mixture was stirred to be degassed while the pressure was reduced. After the degassing, 50 mg (0.2 mmol) of palladium(II) acetate was added. The mixture was stirred at 80° C. for 3 hours under a nitrogen stream. After the stirring, about 50 mL of toluene was added to the mixture and the mixture was stirred for about 30 minutes, and then the mixture was washed with water and saturated saline in this order. After the washing, the organic layer was dried with magnesium sulfate. The mixture was gravity filtered, and the obtained filtrate was concentrated, so that an oily substance was obtained. The obtained oily substance was dissolved in toluene, and this solution was filtered through Florisil (a product of Wako Pure Chemical Industries, Ltd., Catalog No. 540-00135), alumina, and Celite (a product of Wako Pure Chemical Industries, Ltd., Catalog No. 531-16855). The obtained filtrate was concentrated to give 3.3 g of a white solid, which was the object of the synthesis, in a yield of 80%. A synthetic scheme of Step 1 is shown in the following (Z-1).

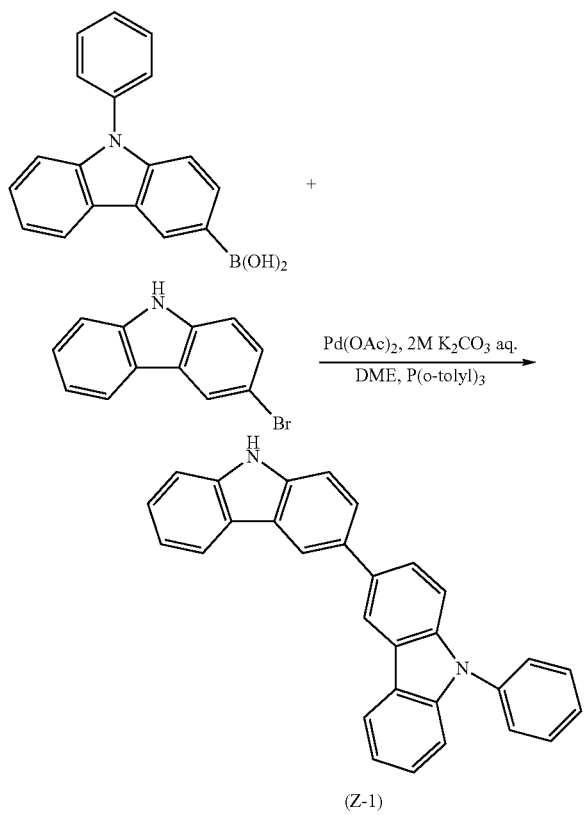

(Z-1)

The solid obtained in the above Step 1 was analyzed by nuclear magnetic resonance measurement (NMR). The measurement data are shown below. From the measurement data, it was found that the organic compound PCC represented by the structural formula (Z-1), which is used for part of the anthracene derivative, was obtained in this example.

$^1$H NMR (DMSO-$d_6$, 300 MHz): δ=7.16-7.21 (m, 1H), 7.29-7.60 (m, 8H), 7.67-7.74 (m, 4H), 7.81-7.87 (m, 2H), 8.24 (d, J=7.8 Hz, 1 H), 8.83 (d, J=7.8 Hz, 1H), 8.54 (d, J=1.5 Hz, 1H), 8.65 (d, J=1.5 Hz, 1H), 11.30 (s, 1H).

[Step 2] Synthesis of PCCPA 1.2 g (3.0 mmol) of 9-(4-bromophenyl)-10-phenylanthracene, 1.2 g (3.0 mmol) of PCC, and 1.0 g (10 mmol) of sodium tert-butoxide were put into a 100 mL three-neck flask. The air in the flask was replaced with nitrogen. 20 mL of toluene and 0.1 mL of tri(tert-butyl)phosphine (a 10 wt % hexane solution) were added to this mixture. This mixture was stirred to be degassed while the pressure was reduced. After the degassing, 96 mg (0.17 mmol) of bis(dibenzylideneacetone)palladium(0) was added to the mixture. This mixture was refluxed at 110° C. for 8 hours under a nitrogen stream. After the reflux, about 50 mL of toluene was added to this mixture. The mixture was stirred for about 30 minutes and then washed with water and saturated saline in this order. After the washing, the organic layer was dried with magnesium sulfate. The mixture was gravity filtered, and the obtained filtrate was concentrated, so that an oily substance was obtained. The obtained oily substance was purified by silica gel column chromatography (developing solvent, hexane:toluene=1:1). The obtained light-yellow solid was recrystallized from chloroform/hexane to give 1.2 g of a light-yellow powdered solid PCCPA, which was the object of the synthesis, in a yield of 54%. 2.4 g of the obtained light-yellow powdered solid was sublimated and purified by train sublimation. The conditions of sublimation purification were as follows: the pressure was 8.7 Pa, the argon gas flow rate was 3.0 mL/min, and the heating temperature of PCCPA was 350° C. After the sublimation purification, 2.2 g of a light-yellow solid PCCPA was recovered in a yield of 94%. A synthetic scheme of Step 2 is shown in the following (Z-2).

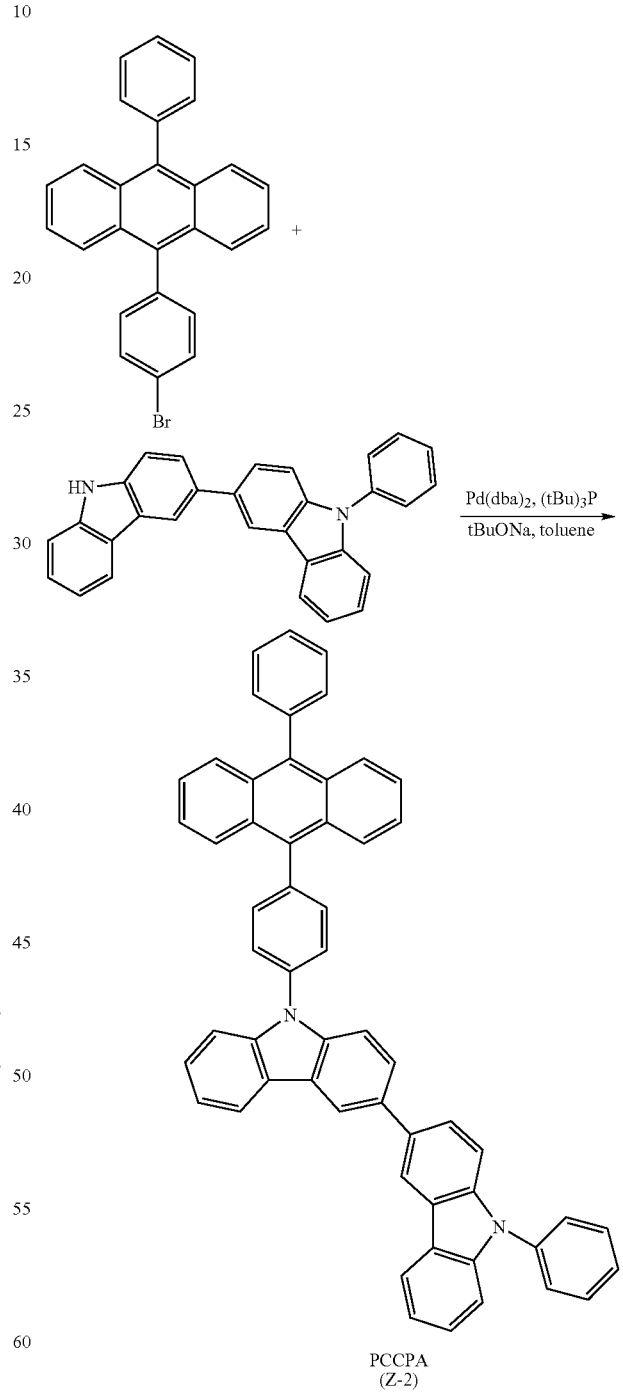

PCCPA
(Z-2)

Note that the solid obtained in the above Step 2 was analyzed by $^1$H NMR. The measurement data are shown below. From the measurement data, it was found that the anthracene derivative PCCPA was obtained in this example.

$^1$H NMR (CDCl$_3$, 300 MHz): δ=7.34-7.91 (m, 32H), 8.27 (d, J=7.2 Hz, 1H), 8.31 (d, J=7.5 Hz, 1H), 8.52 (dd, J$_1$=1.5 Hz, J$_2$=5.4 Hz, 2H).

SYNTHESIS EXAMPLE 2

Next, a synthesis method of 3,3'-(2-tert-buthylanthracene-9,10'-diyldi-4,1-phenylene)bis(9-phenyl-9H-carbazole) (abbr: PCzBPA), which was used in Example 1, is described.

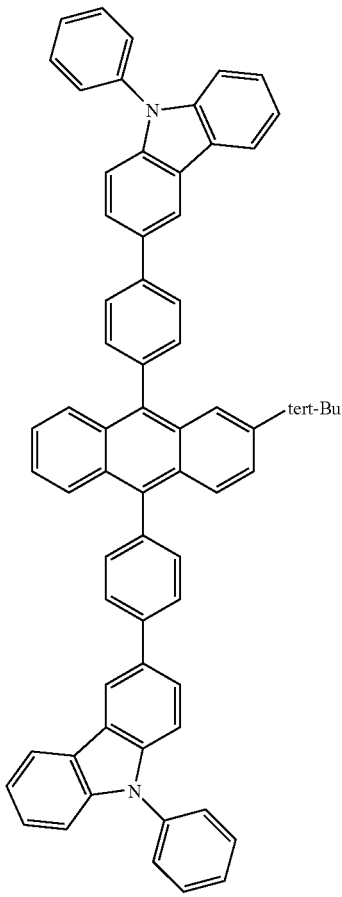

PCzBPA

[Step 1] Synthesis of 9,10-di(4-bromophenyl)-2-tert-butylanthracene (abbr.: BPA)

(1) Synthesis of 9,10-bis(4-bromophenyl)-2-tert-buthyl-9,10-dihydroxy-9,10-dihydroanthracene 1.6 mol/L of butyl lithium hexane solution (13 mL) was dropped into dehydrated ether solution (200 mL) of 1,4-dibromobenzene (5.0 g) at −78° C. under a nitrogen stream. After the dropping, the mixture was stirred for 1 hour at the same temperature. Then, dehydrated ether solution (40 mL) of 2.8 g (11 mmol) of 2-tert-butylanthraquinone was dropped into the mixture at −78° C., and after that, the temperature of the solution was slowly increased to room temperature. Then, the solution was stirred at room temperature for 24 hours, water was added therein, and extracted with ethyl acetate. Then, the organic layer thereof was washed with saturated saline, dried with magnesium sulfate, filtered, and concentrated. The obtained residue was purified with silica-gel chromatography (developing solvent hexane-ethyl acetate), whereby 5.5 g of 9,10-bis(4-bromophenyl)-2-tert-buthyl-9,10-dihydroxy-9,10-dihydroanthracene was obtained in a yield of 90% (synthesis scheme (Y-1)).

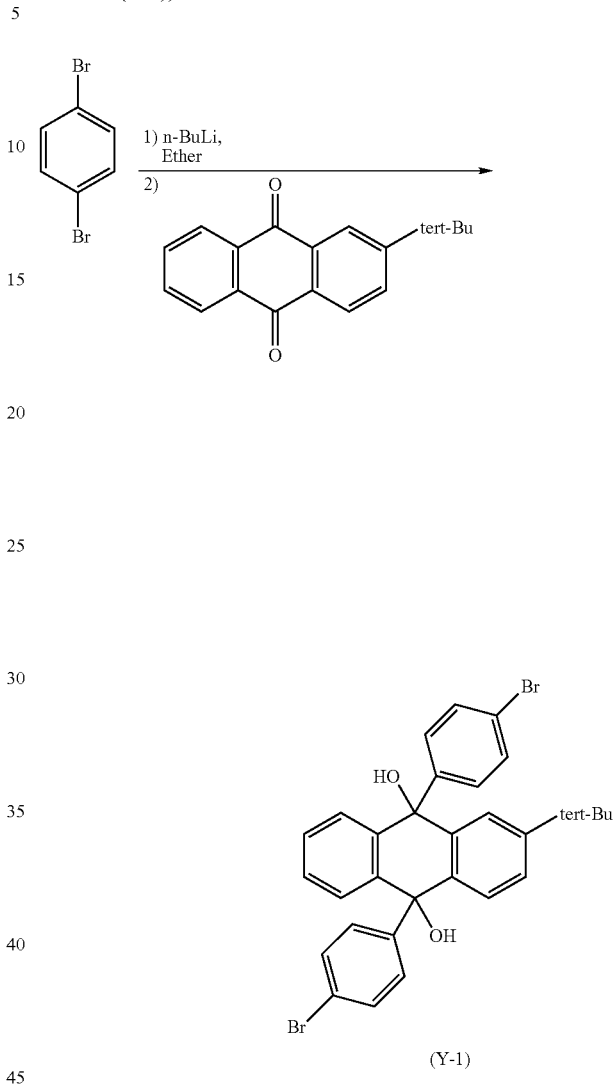

(Y-1)

Note that the solid obtained by the above Step 1(1) described in Synthesis Example 2 was analyzed by $^1$H NMR. The measurement data are shown below.

$^1$H NMR (300 MHz, CDCl$_3$): δ (ppm)=1.31 (s, 9H), 2.81 (s, 1H), 2.86 (s, 1H), 6.82-6.86 (m, 4H), 7.13-7.16 (m, 4H), 7.36-7.43 (m, 3H), 7.53-7.70 (m, 4H).

(2) Synthesis of 9,10-di(4-bromophenyl)-2-tert-butylanthracene (abbr.: BPA) 987 mg (1.6 mmol) of 9,10-bis(4-bromophenyl)-2-tert-buthyl-9,10-dihydroxy-9,10-dihydroanthracene obtained by the above Step 1(1) described in Synthesis Example 2, 664 mg (4.0 mmol) of potassium iodide, 1.48 g (14 mmol) of sodium phosphinate monohydrate, and 12 mL of glacial acetic acid were mixed. The mixture were refluxed under atmospheric air for 2 hours. After the reflux, the mixture was cooled down to room temperature, a generated precipitate was filtered, and the obtained solid was washed with about 50 mL of methanol. The obtained solid was dried, whereby 700 mg of milky white powder of 9,10-di(4-bromophenyl)-2-tert-butylanthracene (abbr.: BPA) was obtained in a yield of 82% (synthesis scheme (Y-2)).

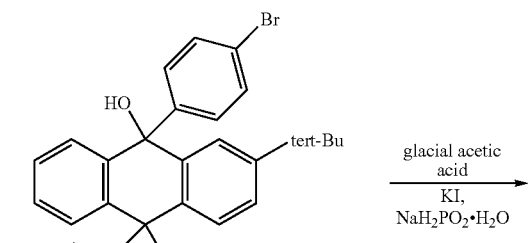

(Y-2)

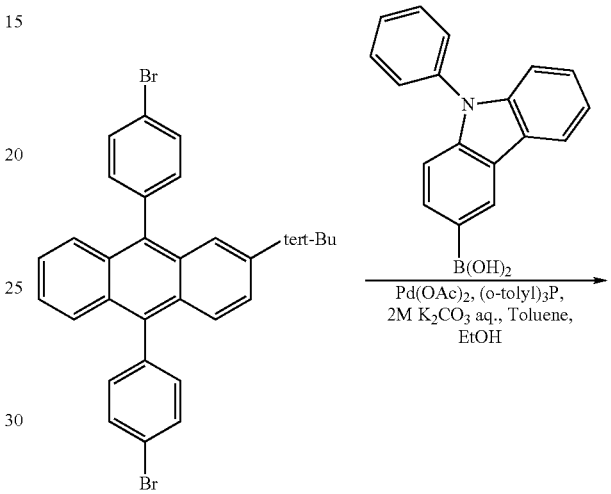

by Wako Pure Chemical Industries, Ltd., Catalog No. 531-16855), and the obtained filtrate was condensed. Then, using silica gel column chromatography (toluene:hexane=1:1), the obtained substance was purified. When ethyl acetate and methanol were added into the obtained solid and ultrasonic waves were applied thereto, 1.8 g of a light-yellow powder, 3,3'-(2-tert-buthylanthracene-9,10-diyldi-4,1-phenylene)bis(9-phenyl-9H-carbazole) (abbr.: PCzBPA), which was the object of the synthesis, was obtained in a yield of 67% (synthesis scheme (Y-3)).

(Y-3)

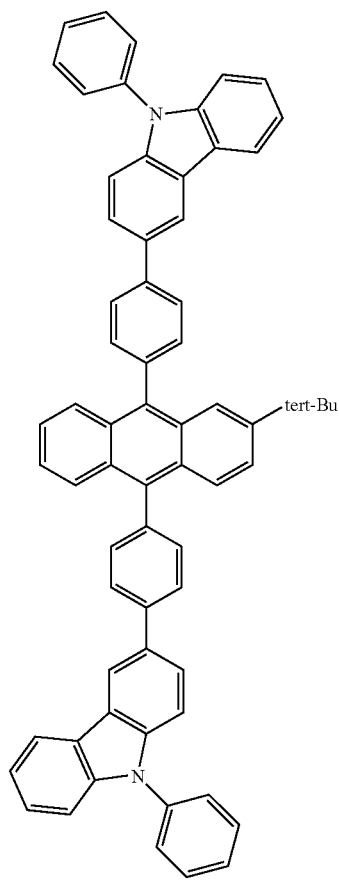

The solid obtained by the above Step 1(2) described in Synthesis Example 2 was measured by $^1$H NMR and $^{13}$C NMR. The measurement data are given below.

$^1$H NMR (300 MHz, CDCl$_3$): δ (ppm)=1.28 (s, 9H), 7.25-7.37 (m, 6H), 7.44-7.48 (m, 1H), 7.56-7.65 (m, 4H), 7.71-7.76 (m, 4H). $^{13}$C NMR (74 MHz, CDCl$_3$): δ (ppm)=30.8, 35.0, 120.8, 121.7, 121.7, 124.9, 125.0, 125.2, 126.4, 126.6, 126.6, 128.3, 129.4, 129.7, 129.9, 131.6, 131.6, 133.0, 133.0, 135.5, 135.7, 138.0, 138.1, 147.8.

[Step 2] Synthesis of 3,3'-(2-tert-buthylanthracene-9,10-diyldi-4,1-phenylene)bis(9-phenyl-9H-carbazole) (abbr.: PCzBPA)

In a 200 mL three-neck flask were heated 1.6 g (3.0 mmol) of 9,10-bis(4-bromophenyl)-2-tert-buthylanthracene (abbr.: BPA) obtained by the above Steps 1(1) and 1(2) described in Synthesis Example 2, 1.7 g (6.0 mmol) of 9-phenyl-9H-carbazol-3-boronic acid, 13 mg (60 μmol) of palladium(II) acetate (abbr.: Pd(OAC)$_2$), 36 mg (120 μmol) of tris(o-tolyl)phosphine (abbr.: P(o-tolyl)$_3$), 5 mL (10 mmol) of potassium carbonate solution (2.0 mol/L), 20 mL of toluene, and 5 mL of ethanol in a nitrogen atmosphere for 5.5 hours at 90° C. After the temperature of this mixture was cooled to room temperature, 200 mL of toluene was added, and then, the mixture was filtered through Florisil (produced by Wako Pure Chemical Industries, Ltd., Catalog No. 540-00135), silica gel, and Celite (produced by Wako Pure Chemical Industries, Ltd., Catalog No. 531-16855). The obtained filtrate was washed with water, and magnesium sulfate was added therein, so that the filtrate was dried. This mixture was filtered through Florisil (produced by Wako Pure Chemical Industries, Ltd., Catalog No. 540-00135), silica gel, alumina, and Celite (produced PCzBPA was analyzed by $^1$H NMR. The measurement data is given below.

$^1$H MR (300 MHz, CDCl$_3$): δ (ppm)=1.31 (s, 9H), 7.32-7.90 (m, 31H), 7.99 (t, J=7.8, 4H), 8.25-8.29 (m, 2H), 8.57 (d, J=8.1, 2H).

SYNTHESIS EXAMPLE 3

Next, a synthesis method of 9-phenyl-3-[4-(10-phenyl-9-anthryl)phenyl]-9H-carbazol (abbr.: PCzPA) which was used in Example 1 is described.

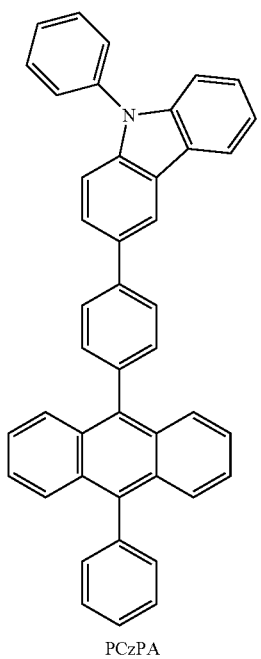

PCzPA

[Step 1] Synthesis of 9-(4-bromophenyl)-10-phenylanthracene (abbr.: PA)

(1) Synthesis of 9-phenylanthracene

Into a 200 mL three-neck flask were put 5.4 g (21 mmol) of 9-bromoanthracene, 2.6 g (21 mmol) of phenylboronic acid, 60 mg (0.2 mmol) of palladium(II) acetate (abbr.: Pd(OAc)$_2$), 10 mL (20 mmol) of potassium carbonate solution (2.0 mol/L), 260 mg (0.8 mmol) of tris(o-tolyl)phosphine (abbr.: P(o-tolyl)$_3$), and 20 mL of ethylene glycol dimethyl ether; and then the mixture was stirred at 80° C. under a nitrogen stream for 9 hours. After the stirring, a precipitated solid was collected by suction filtration, dissolved in toluene, and filtered through Florisil (produced by Wako Pure Chemical Industries, Ltd., Catalog No. 540-00135), Celite (produced by Wako Pure Chemical Industries, Ltd., Catalog No. 531-16855), and alumina. The obtained filtrate was washed with water and saturated saline, followed by drying with magnesium sulfate. This suspending solution was gravity filtered and the obtained filtrate was concentrated, whereby 22 g of a light-brown solid of 9-phenylanthracene, which was the object of the synthesis, was obtained in a yield of 85% (synthesis scheme (X-1)).

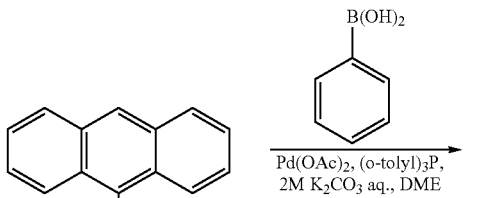

(X-1)

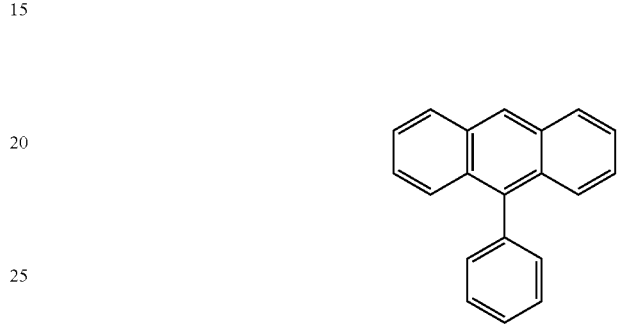

(2) Synthesis of 9-bromo-10-phenylanthracene 6.0 g (24 mmol) of 9-phenylanthracene obtained by the above Step 1(1) of Synthesis Example 3 was dissolved in 80 mL of carbon tetrachloride. Then, the solution was stirred while dropping a solution in which 3.8 g (21 mmol) of bromine was dissolved in 10 mL of carbon tetrachloride into the solution from a dropping funnel. After dropping, it was stirred for one hour at room temperature. After the stirring, sodium thiosulfate solution was added into the obtained solution. After that, the organic layer thereof was washed with aqueous sodium hydroxide and saturated saline in this order. Then, magnesium sulfate was added to the organic layer for drying. A solid obtained by gravity filtration of this mixture and concentration of the filtrate was dissolved in toluene, and this solution was filtered through Florisil (product of Wako Pure Chemical Industries, Ltd., Catalog No. 540-00135), Celite (product of Wako Pure Chemical Industries, Ltd., Catalog No. 531-16855), and alumina. The obtained filtrate was concentrated and recrystallized from a mixed solvent of dichloromethane and hexane, whereby 7.0 g of a light-yellow solid of 9-bromo-10-phenylanthracene, which was the object of the synthesis, was obtained in a yield of 89%. (synthesis scheme (X-2)).

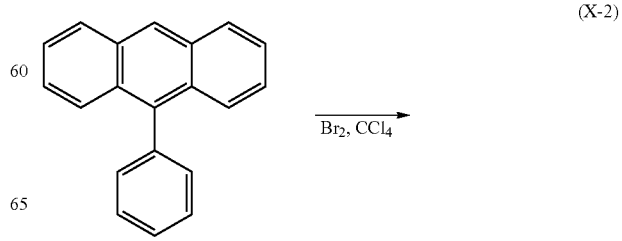

(X-2)

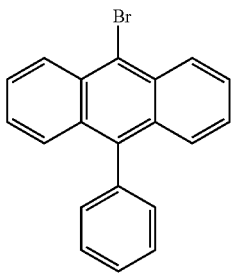

(3) Synthesis of 9-iodo-10-phenylanthracene

Under a nitrogen stream, 3.3 g (10 mmol) of 9-bromo-10-phenylanthracene obtained by the above Step 1(2) of Synthesis Example 3 was dissolved in 80 mL of tetrahydrofuran (abbr: THF) and the temperature of the solution was set at −78° C. Then, 7.5 mL (12 mmol) of n-butyllithium (abbr.: n-BuLi) (1.6 mol/L hexane solution) was dropped into this solution from a dropping funnel, and after the dropping, this mixture was stirred for 1 hour at the same temperature. After the stirring, a solution in which 5.0 g (20 mmol) of iodine was dissolved in 20 mL of THF was added therein, and this mixture was further stirred at −78° C. for 2 hours. After the stirring, the temperature of this solution was brought back to room temperature, and then sodium thiosulfate solution was added into this solution. After that, the organic layer thereof was washed with sodium thiosulfate solution and saturated saline in this order. Then, magnesium sulfate was added for drying. This mixture was filtered, the filtrate was concentrated, and the obtained solid was recrystallized from ethanol, whereby 3.1 g of a light-yellow solid of 9-iodo-10-phenylanthracene, which was the object of the synthesis, was obtained in a yield of 83%. (synthesis scheme (X-3))

(X-3)

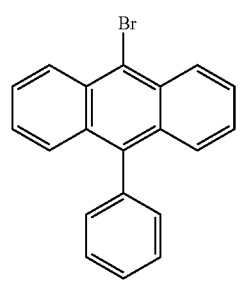

(4) Synthesis of 9-(4-bromophenyl)-1'-phenylanthracene (abbr.: PA)

A mixture of 1.0 g (2.6 mmol) of 9-iodo-10-phenylanthracene obtained by the above Step 1(3) of Synthesis Example 3, 540 mg (2.7 mmol) of p-bromophenylboronic acid, 46 mg (30 μmol) of tetrakis(triphenylphosphine)palladium(0) (abbr.: Pd(PPh$_3$)$_4$), 3.0 mL (6.0 mmol) of 2.0 mmol/L potassium carbonate solution, and 10 mLC of toluene was stirred under a nitrogen stream at 80° C. for 9 hours. After the stirring, toluene was added to this mixture, and the mixture was filtered through Florisil (produced by Wako Pure Chemical Industries, Ltd., Catalog No. 540-00135), Celite (produced by Wako Pure Chemical Industries, Ltd., Catalog No. 531-16855), and alumina. The obtained filtrate was washed with water and saturated saline and then magnesium sulfate was added therein for drying. This mixture was gravity filtered and the obtained filtrate was concentrated. The obtained solid was recrystallized from a mixed solvent of chloroform and hexane, whereby 560 mg of a light-brown solid of 9-(4-bromophenyl)-10-phenylanthracene (abbr.: PA), which was the object of the synthesis, was obtained in a yield of 45% (synthesis scheme (X-4)).

(X-4)

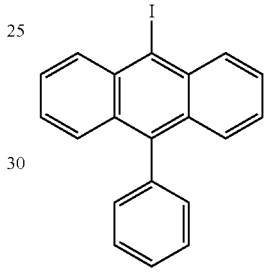 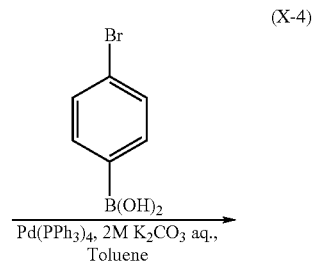

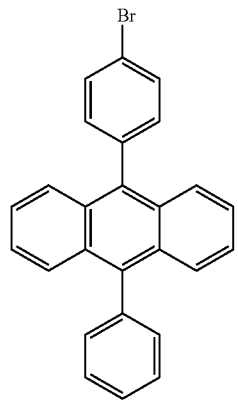

[Step 2] Synthesis of 4-(10-phenyl-9-anthryl)phenylboronic Acid

In a 500 mL three-neck flask were added 20 g (49 mmol) of 9-(4-bromophenyl)-10-phenylanthracene obtained by the above Steps 1(1) to 1(4) of Synthesis Example 3 and 300 mL of tetrahydrofuran (abbr.: THF), and the mixture was stirred under a nitrogen stream at −78° C. Then, 34 mL (54 mmol) of n-butyllithium (1.6 mol/L hexane solution) was dropped, and this mixture was stirred for 2 hours at the same temperature. After the stirring, 13 mL (110 mmol) of trimethyl borate was added to this solution, and the mixture was stirred for 24 hours at room temperature. After the stirring, this mixture was brought back to room temperature, 200 mL of (1.0 molL) hydrochloric acid was added therein, and this mixture was stirred for 1 hour. After that, the organic layer thereof was washed with water and separated into the organic layer and the aqueous layer, and the obtained aqueous layer was extracted with ethyl acetate. After this extracted solution was washed together with the organic layer with saturated saline, magnesium sulfate was added therein for drying. The mixture was subjected to suction filtration, and the obtained filtrate was concentrated to obtain a solid. The obtained solid was recrystallized from a mixed solvent of chloroform and hexane, whereby 15 g of a white powdered solid of 4-(10-phenyl-9-anthryl)phenylboronic acid, which was the object of the synthesis, was obtained in a yield of 84% (synthesis scheme (X-5)).

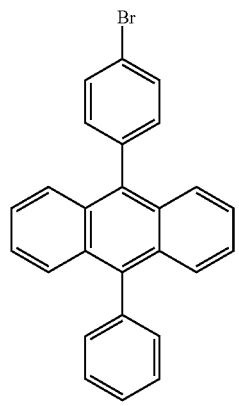
(X-5)

1) BuLi, THF
2) B(OMe)$_3$, THF
→

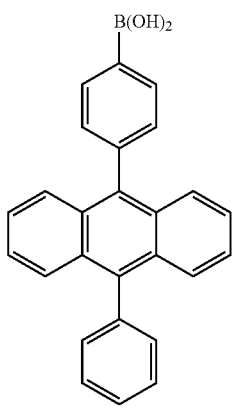

[Step 3] Synthesis of 3-bromo-9-phenyl-9H-carbazole

In a 1000 mL conical flask were added 24 g (100 mmol) of 9-phenyl-9H-carbazole, 18 g (100 mmol) of N-bromo succinimide, 450 mL of toluene, and 200 mL of ethyl acetate, and this solution was stirred at room temperature for 45 hours. After the stirring, the obtained mixture was washed with water, and then magnesium sulfate was added therein for drying. When this mixture was filtered and the obtained filtrate was concentrated and dried, 32 g of a brown oily substance of 3-bromo-9-phenylcarbazole, which was the object of the synthesis, was obtained in a yield of 99% (synthesis scheme (X-6)).

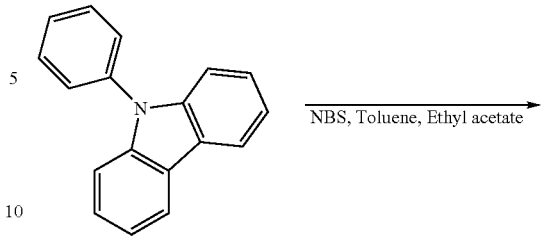
(X-6)

NBS, Toluene, Ethyl acetate →

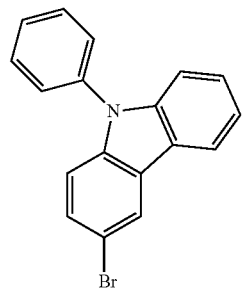

[Step 4] Synthesis of 9-phenyl-3-[4-(10-phenyl-9-anthryl)phenyl]-9H-carbazol (abbr.: PCzPA)]

In a 100 mL three-neck flask were heated 2.6 g (7.0 mmol) of 4-(10-phenyl-9-anthryl)phenylboronic acid obtained by the above Step 2 of Synthesis Example 3, 2.3 g (7.0 mmol) of 3-bromo-9-phenylcarbazole obtained by the above Step 3 of Synthesis Example 3, 2.0 mg (10 μmol) of palladium(II) acetate (abbr.: Pd(OAc)$_2$), 6.0 mg (20 μmol) of tris(o-tolyl) phosphine (abbr.: P(o-tolyl)$_3$), 5 mL (10 mmol) of potassium carbonate solution (2 mol/L), and 20 mL of ethyleneglycoldimethylether (abbr.: DME) under a nitrogen stream for 6.5 hours at 90° C. After this mixture was cooled to room temperature, 200 mL of toluene was added, and then the mixture was filtered through Florisil (produced by Wako Pure Chemical Industries, Ltd., Catalog No. 540-00135), alumina, and Celite (produced by Wako Pure Chemical Industries, Ltd., Catalog No. 531-16855). When the obtained filtrate was concentrated, acetone and methanol were added into the obtained substance and ultrasonic waves were applied to this solution, 3.8 g of a light-yellow powder of 9-phenyl-3-[4-(10-phenyl-9-anthryl)phenyl]-9H-carbazol (abbr.: PCzPA), which was the object of the synthesis, was obtained in a yield of 95% (synthesis scheme (X-7)).

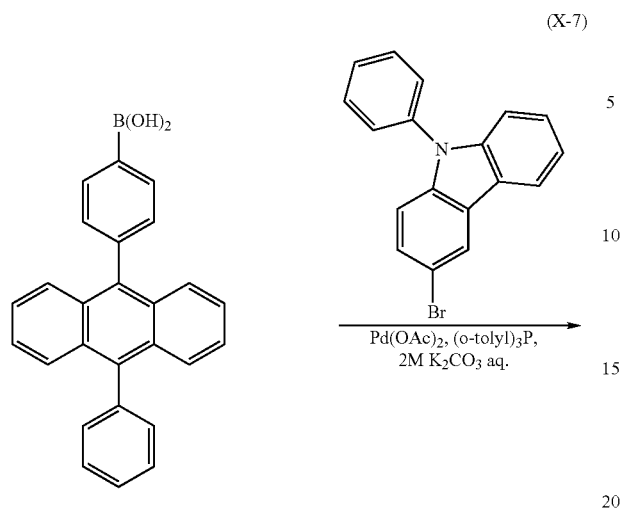
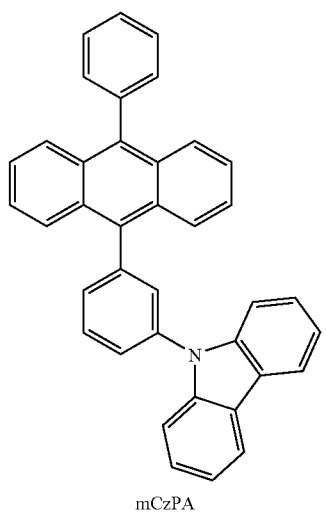

Note that PCzPA was measured by $^1$H NMR. The measurement data are shown below.

$^1$H NMR (300 MHz, CDCl$_3$): δ (ppm)=7.32-7.98 (m, 27H), 8.25 (d, J=7.8 Hz, 1H), 8.55 (d, J=1.5 Hz, 1H).

Synthesis Example 4

Next, a synthesis method of 9-[3-(10-phenyl-9-anthryl)phenyl]-9H-carbazole (abbr. mCzPA) which was used in Example 1 is described.

[Step 1] Synthesis of 9-(3-bromophenyl)-10-phenylanthracene (mPA unit)

A synthetic scheme of 9-(3-bromophenyl)-10-phenylanthracene (mPA unit) is shown in the following (J-3).

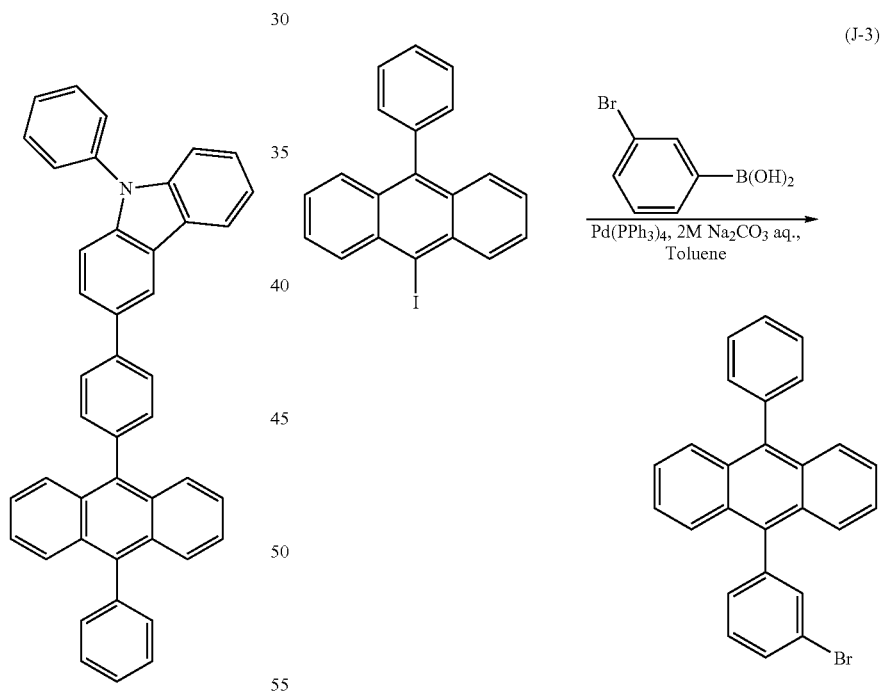

Into a 300 mL three-neck flask were put 2.5 g (6.6 mmol) of 9-iodo-10-phenylanthracene and 1.3 g (6.6 mmol) of 3-bromophenylboronic acid which were obtained through the Steps 1(1) to (3) of Synthesis Example 3. The air in the flask was replaced with nitrogen, and then 5.0 mL of a sodium carbonate solution (2.0 mol/L) and 40 mL of toluene were added thereto. This mixture was stirred to be degassed while the pressure was reduced. After the degassing, 0.38 g (0.33 mmol) of tetrakis(triphenylphosphine)palladium(0) was put into this mixture, and this mixture was stirred under a nitrogen stream at 100° C. for 15 hours. After the stirring, the aqueous layer of this mixture was extracted with toluene and the extracted solution and the organic layer were washed together with saturated saline. The organic layer was dried with magnesium sulfate and this mixture was gravity filtered. After the obtained filtrate was concentrated, it was subjected to suction filtration through Celite (Wako Pure Chemical Industries, Ltd., catalog No.: 531-16855), alumina, and Florisil (Wako Pure Chemical Industries, Ltd., catalog No.: 540-00135). When the obtained filtrate was concentrated, a light-brown oily substance was obtained. The obtained oily substance was recrystallized from toluene/hexane to give 1.3 g of a light-yellow powder, which was the object of the synthesis, in a yield of 50%.

[Step 2] Synthesis of 9-[3-(10-phenyl-9-anthryl)phenyl]-9H-carbazole (abbr. mCzPA)

A synthetic scheme of 9-[3-(10-phenyl-9-anthryl)phenyl]-9H-carbazole (abbr. mCzPA) is shown in the following (J-4).

(J-4)

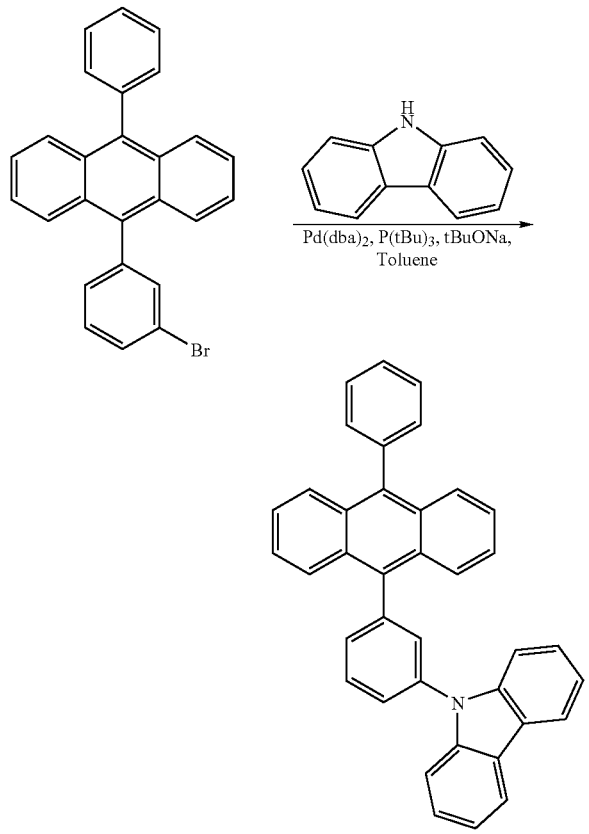

Into a 200 mL three-neck flask were put 1.3 g (3.3 mmol) of 9-(3-bromophenyl)-10-phenylanthracene (abbr: mPA), 0.55 g (3.3 mmol) of 9H-carbazole, and 0.63 g (6.6 mmol) of sodium tert-butoxide. After the air in the flask was replaced with nitrogen, 40 mL of toluene and 0.40 mL of tri(tert-butyl) phosphine (10 wt % hexane solution) were added to this mixture. This mixture was stirred to be degassed while the pressure was reduced. After the degassing, 95 mg (0.17 mmol) of bis(dibenzylideneacetone)palladium(0) was added to this mixture. This mixture was stirred under a nitrogen stream at 110° C. for 8 hours. After the stirring, this mixture was subjected to suction filtration through Celite (Wako Pure Chemical Industries, Ltd., catalog No.: 531-16855), alumina, and Florisil (Wako Pure Chemical Industries, Ltd., catalog No.: 540-00135). The obtained filtrate was concentrated to give a light-yellow oily substance. The obtained oily substance was recrystallized from toluene/hexane to give 1.2 g of a light-yellow solid, which was the object of the synthesis, in a yield of 71%.

The results of mass spectrometry of the obtained compound are shown below.

ESI MS:m/z=496 [M+H]+

The obtained substance was analyzed by $^1$H NMR. It was confirmed that this compound was 9-[3-(10-phenyl-9-anthryl)phenyl]-9H-carbazole (abbr. mCzPA). The measurement data is shown below.

Figure 20A:
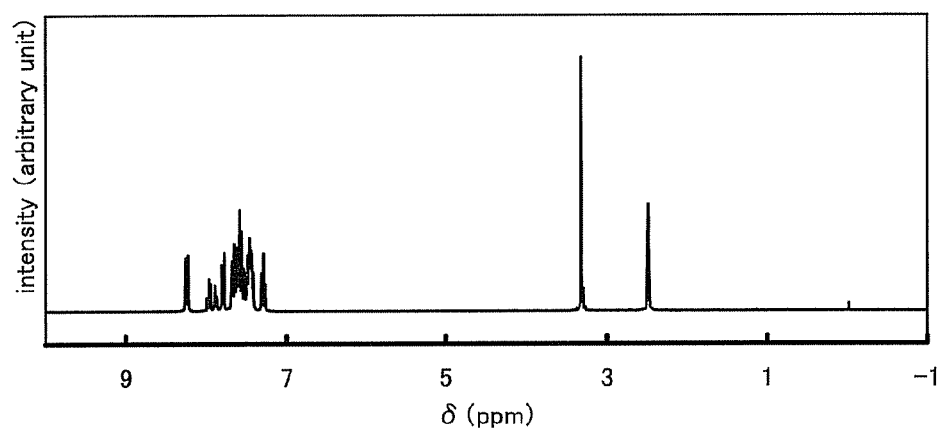
FIGS. 20A and 20B are $^1$H NMR charts of 9-[3-(10-phenyl-9-anthryl)phenyl]-9H-carbazole (abbr.: mCzPA)
Figure 20B:
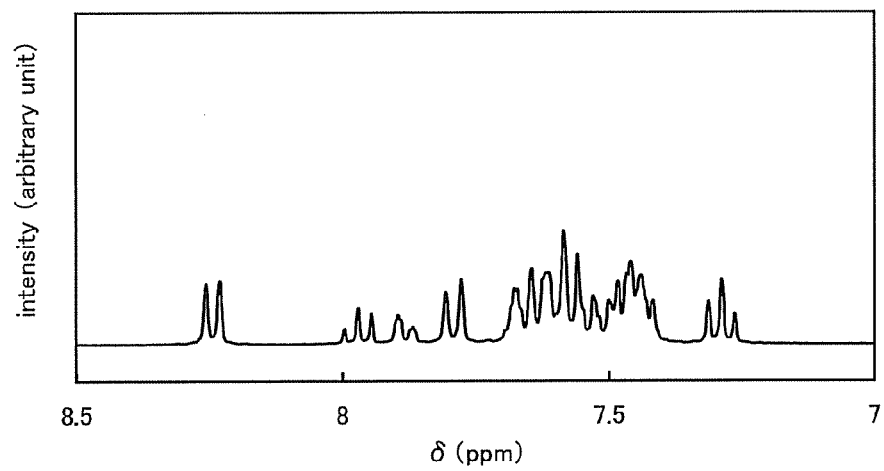

$^1$H NMR (DMSO-$d_6$, 300 MHz): δ=7.30 (t, J=4.5 Hz, 2H), 7.43-7.69 (m, 17H), 7.80 (d, J=8.7 Hz, 2H), 7.89 (d, J=7.8 Hz, 1H), 7.98 (t, J=7.5 Hz, 1H), 8.26 (d, J=10.2 Hz, 2H). The $^1$H NMR chart is shown in FIGS. 20A and 20B. Note that FIG. 20B is a chart in which the range of 7.0 ppm to 8.5 ppm in FIG. 20A is enlarged.

Figure 21:
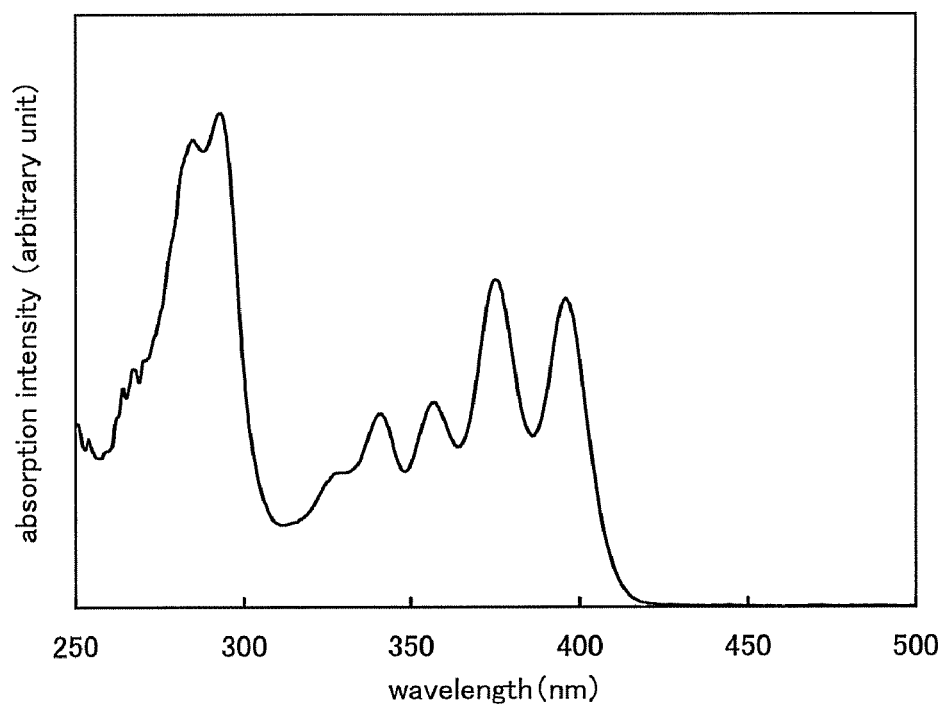
FIG. 21 is a graph showing an absorption spectrum of a toluene solution of 9-[3-(10-phenyl-9-anthrylphenyl]-9H-carbazole (abbr: mCzPA)
Figure 22:
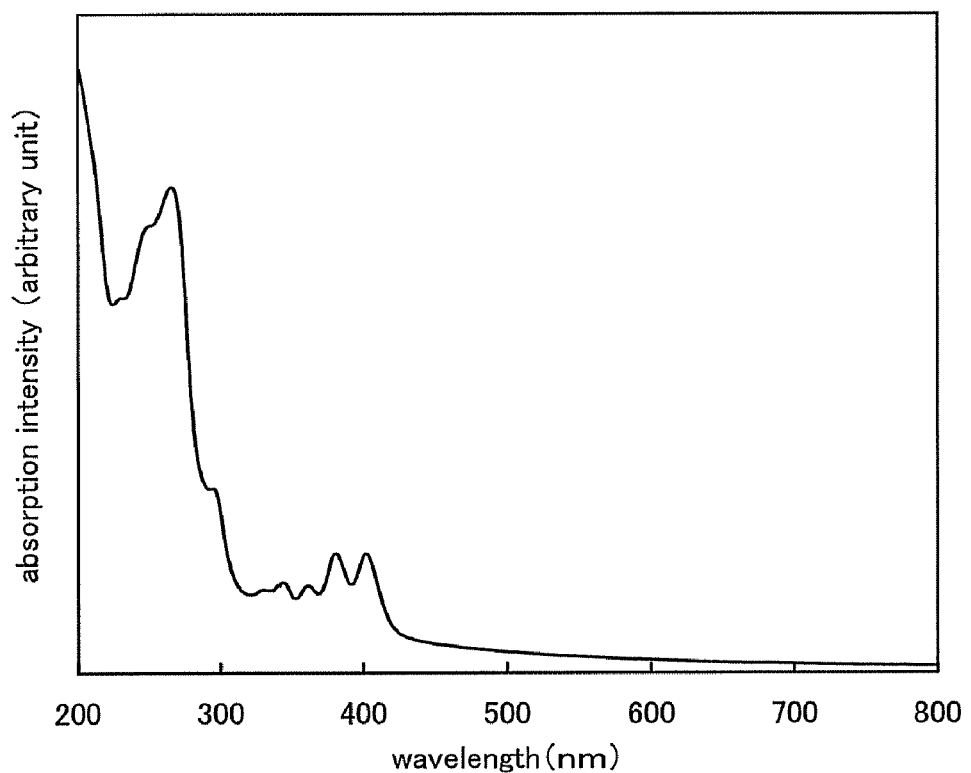
FIG. 22 is a graph showing an absorption spectrum of a thin film of 9-[3-(10-phenyl-9-anthryl)phenyl]-9H-carbazole (abbr.: mCzPA)
Figure 23:
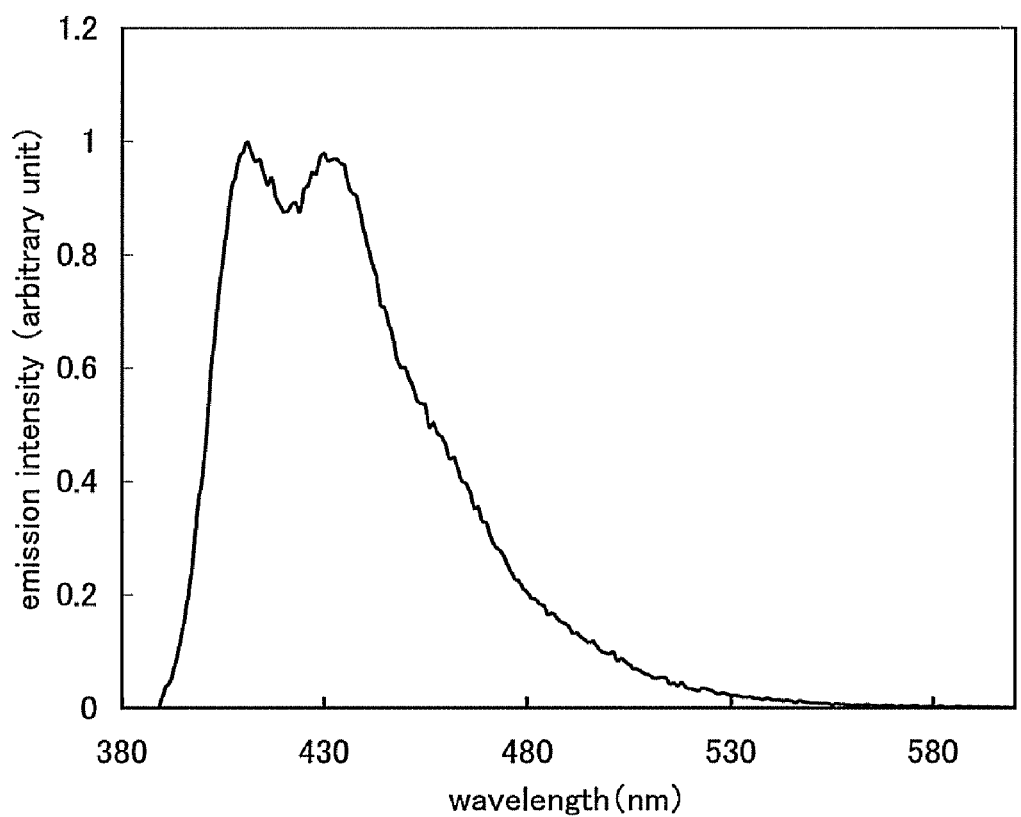
FIG. 23 is a graph showing an emission spectrum of a toluene solution of 9-[3-(10-phenyl-9-anthryl)phenyl]-9H-carbazole (abbr.: mCzPA)
Figure 24:
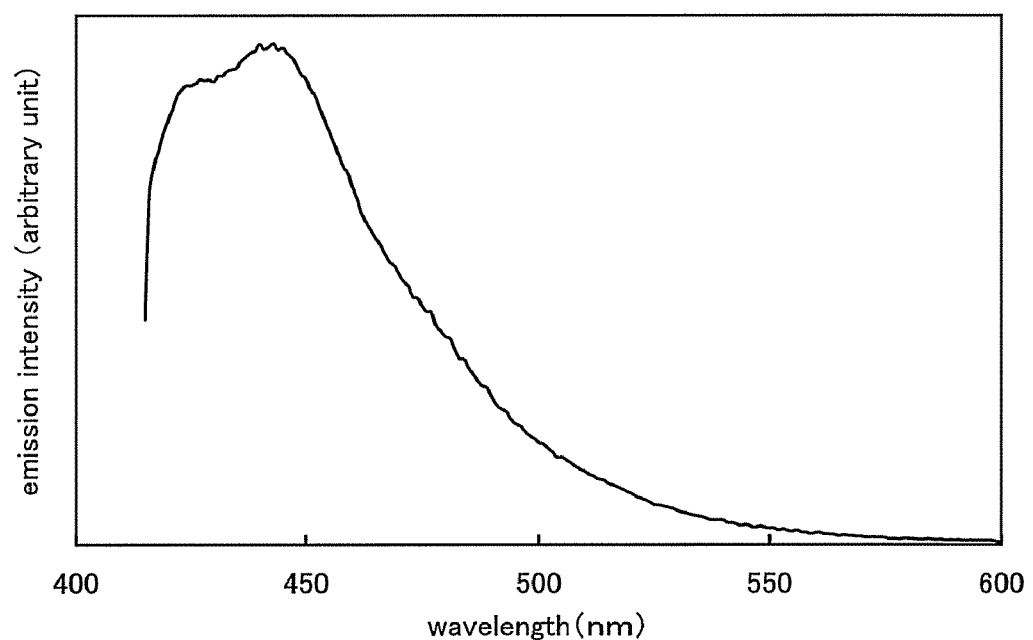
FIG. 24 is a graph showing an emission spectrum of a thin film of 9-[3-(10-phenyl-9-anthryl)phenyl]-9H-carbazole (abbr.: mCzPA)

FIG. 21 shows an absorption spectrum of a toluene solution of mCzPA. FIG. 22 shows an absorption spectrum of a thin film of mCzPA. An ultraviolet-visible spectrophotometer (V-550, manufactured by JASCO Corporation) was used for the measurement. The solution was put in a quartz cell. The thin film was formed by evaporation over a quartz substrate to form a sample. As for the spectrum of the solution, the absorption spectrum which was obtained by subtracting the absorption spectrum of the quartz cell including only toluene is shown in FIG. 21 and as for the spectrum of the thin film, the absorption spectrum which was obtained by subtracting the absorption spectrum of the quartz substrate is shown in FIG. 22. In each of FIG. 21 and FIG. 22, the horizontal axis shows wavelength (nm), and the vertical axis shows absorption intensity (arbitrary unit). In the case of the toluene solution, an absorption was observed at around 396 nm, 375 nm, 357 nm, and 341 nm. In the case of the thin film, an absorption was observed at around 402 nm, 381 nm, 361 nm, 344 nm, 331 nm, and 294 nm. In addition, an emission spectrum of the toluene solution of mCzPA (excitation wavelength: 375 nm) is shown in FIG. 23, while that of the thin film of mCzPA (excitation wavelength: 400 nm) is shown in FIG. 24. In FIGS. 23 and 24, the horizontal axis indicates wavelength (nm) and the vertical axis indicates light emission intensity (arbitrary unit). In the case of the toluene solution, the maximum emission wavelength was 411 nm (excitation wavelength: 375 nm), and in the case of the thin film, the maximum emission wavelength was 443 nm (excitation wavelength: 400 nm).

The measurement results of the thin film of mCzPA by photoelectron spectrometry (AC-2, product of Riken Keiki Co., Ltd.) in the atmosphere indicated that the HOMO level of mCzPA was −5.82 eV. Moreover, the absorption edge was obtained from Tauc plot, with an assumption of direct transition, using data on the absorption spectrum of the thin film of mCzPA in FIG. 22. When the absorption edge was estimated as an optical energy gap, the energy gap was 2.96 eV. The LUMO level, which was estimated from the HOMO level and the energy gap, was −2.86 eV.

Synthesis Example 5

Next, a synthesis method of 9-[4-(9,10-diphenyl-2-anthryl)phenyl]-9H-carbazole (abbr.: 2CzPPA) which was used in Example 1 is described.

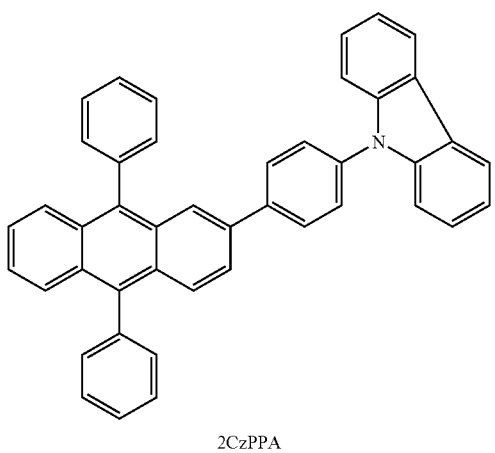

2CzPPA

[Step 1] Synthesis of 9-[4-(9,10-diphenyl-2-anthryl)phenyl]-9H-carbazole (abbr.: 2CzPPA)

A synthetic scheme of 2CzPPA is shown in the following (E-1).

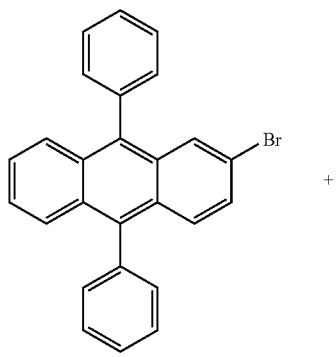

+

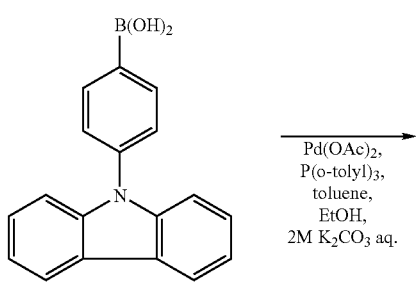

$\xrightarrow{\text{Pd(OAc)}_2,\ \text{P(o-tolyl)}_3,\ \text{toluene},\ \text{EtOH},\ \text{2M K}_2\text{CO}_3\ \text{aq.}}$ (E-1)

-continued

In a 100 mL three neck flask were put 2.0 g (4.9 mmol) of 2-bromo-9,10-diphenylanthracene, 1.4 g (4.9 mmol) of 4-(9H-carbazol-9-yl)phenylboronic acid, and 0.15 g (0.50 mmol) of tri(ortho-tolyl)phosphine, and the air in the flask was replaced with nitrogen. To this mixture were added 15 mL of toluene, 15 mL of ethanol, and 10 mL of a potassium carbonate solution (2.0 mol/L). This mixture was degassed while being stirred under reduced pressure. After the degassing, the air in the flask was replaced with nitrogen. 23 mg (0.10 mmol) of palladium(II) acetate was added to this mixture. This mixture was refluxed at 100° C. for 20 hours. After the reflux, after this mixture was cooled to room temperature, and then about 50 mL of toluene was added thereto, and the mixture was filtered through a filter paper. The obtained mixture was washed with water, and the aqueous layer was extracted with toluene. The extracted solution was washed together with the organic layer with saturated saline, and the organic layer was dried with magnesium sulfate. This mixture was gravity filtered. The obtained filtrate was concentrated to give a light-yellow solid. This solid was washed with toluene to give 1.5 g of a light-yellow powdered solid which was the object of the synthesis in a yield of 54%.

Then, 1.5 g of the obtained light-yellow powdered solid was sublimated and purified by train sublimation. The sublimation purification conditions were such that 2CzPPA was heated at 260° C. while flowing argon gas at a flow rate of 3.0 mL/min. After the sublimation purification, 1.4 g of a light-yellow solid of 2CzPPA was recovered in a yield of 94%.

By nuclear magnetic resonance (NMR) measurement, it was confirmed that this compound was 9-[4-(9,10-diphenyl-2-anthryl)phenyl]-9H-carbazole (abbr.: 2CzPPA).

The $^1$H NMR data of 2CzPPA are shown as follows: $^1$H NMR (CCl$_3$, 300 MHz): δ 7.30 (d, J=6.3 Hz, 2H), 7.33-7.75 (m, 21H), 7.77 (d, J=8.1 Hz, 2H), 7.85 (d, J=9.0 Hz, 1H), 8.01 (d, J=2.1 Hz, 1H), 8.15 (d, J=7.8 Hz, 2H).

Synthesis Example 6

Next, a synthesis method of 9-(9,10-diphenyl-2-anthryl)-9H-carbazole (abbr.: 2CzPA) which was used in Example 1 is described.

[Step 1] Synthesis of 9-(9,10-diphenyl-2-anthryl)-9H-carbazole (abbr: 2CzPA)

First, 1.5 g (3.7 mmol) of 2-bromo-9,10-diphenylanthracene, which was used in Step 1 of Synthesis Example 5, 610 mg (3.7 mmol) of 9H-carbazole, and 1.5 g (16 mmol) of sodium tert-butoxide were put into a 100 mL three-neck flask, and the air in the flask was replaced with nitrogen. 20 mL of toluene and 0.10 mL of tri(tert-butyl)phosphine (10 wt % hexane solution) were added to this mixture. This mixture was degassed while being stirred under reduced pressure, and after the degassing, 58 mg (0.10 mmol) of bis(dibenzylideneacetone)palladium(0) was added. This mixture was refluxed at 110° C. for 5 hours. After the reflux, this mixture was cooled to room temperature and about 20 mL of toluene was added to this mixture. The mixture was then filtered through alumina, Celite (produced by Wako Pure Chemical Industries, Ltd., Catalog No. 531-16855), and Florisil (produced by Wako Pure Chemical Industries, Ltd., Catalog No. 540-00135). The obtained filtrate was concentrated to give a light-brown oily substance. This oily substance was purified by silica gel column chromatography (a developing solvent was a mixed solvent of hexane:toluene=6:4). The obtained light-yellow solid substance was recrystallized from ethanol, so that 1.7 g of a light-yellow powdered solid was obtained in a yield of 93%. At a pressure of 8.7 Pa and with an argon gas flowing at a flow rate of 3.0 mL/min, 1.6 g of the obtained light-yellow powdered solid substance was heated at 230° C. so as to be sublimated and purified (a train sublimation method). After the sublimation purification, 1.5 g of a light-yellow solid substance was recovered in a yield of 93%. A synthesis scheme of Step 1 is shown in (F-3) given below.

The obtained light-yellow solid was analyzed by nuclear magnetic resonance measurement ($^1$H NMR). Then, it was confirmed that this light-yellow solid was 9-(9,10-diphenyl-2-anthryl)-9H-carbazole (abbr. 2CzPA), which was the object of the synthesis. The measurement data is shown below.

$^1$H NMR (CDCl$_3$, 300 MHz) δ=7.37-7.44 (m, 8H), 7.51-7.66 (m, 11H), 7.73-7.76 (m, 2H), 7.88 (d, J=1.8 Hz, 1H), 7.91 (d, J=9.3 Hz, 1H), 8.11 (d, J=7.8 Hz, 2H).

Synthesis Example 7

Next, a synthesis method of 3-(9,10-diphenyl-2-anthryl)-9-phenyl-9H-carbazole (abbr.: 2PCzPA) which was used in Example 1 is described.

[Step 1] Synthesis of 2PCzPA

A synthetic scheme of 2PCzPA is shown in the following (G-4).

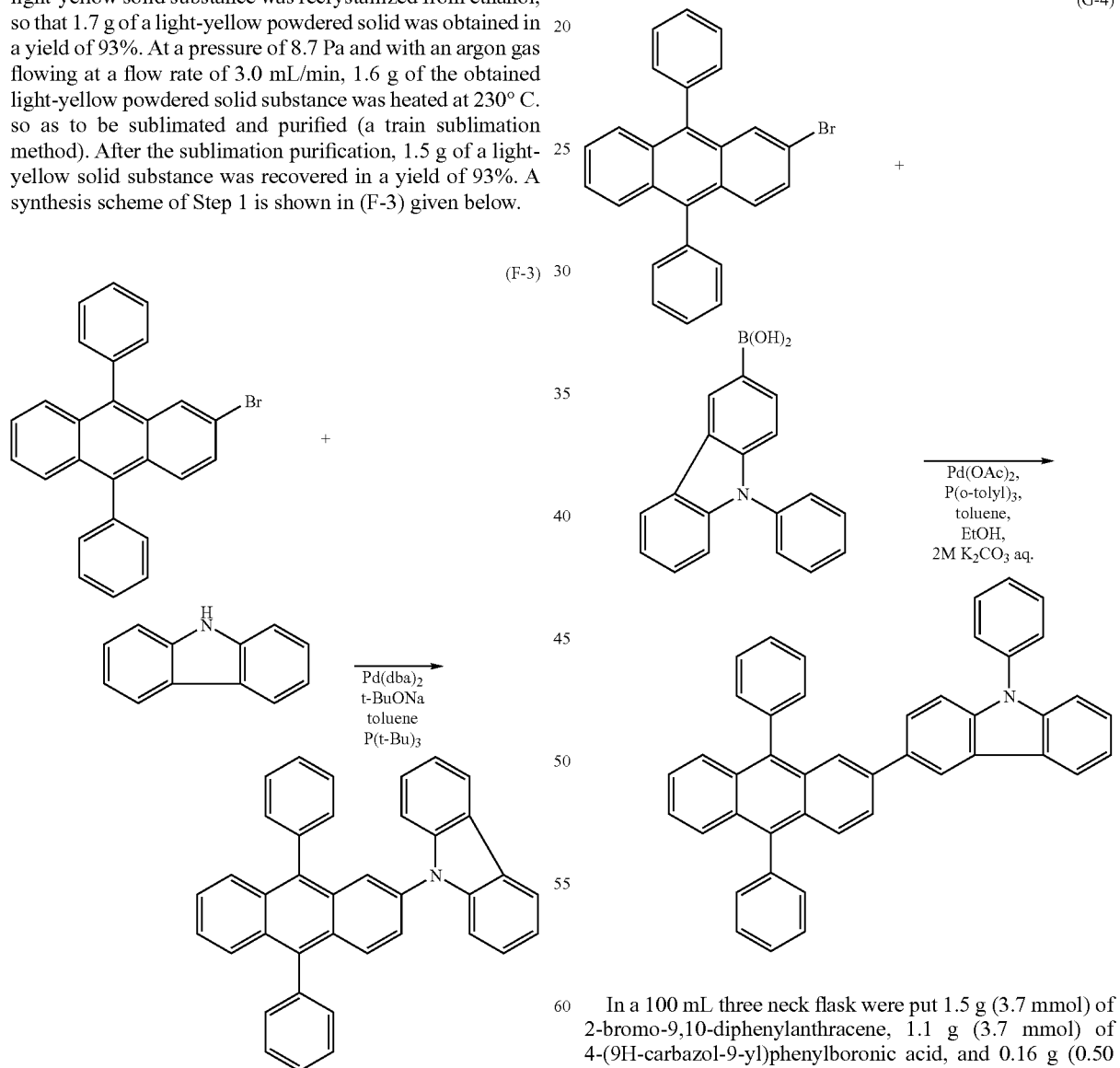

In a 100 mL three neck flask were put 1.5 g (3.7 mmol) of 2-bromo-9,10-diphenylanthracene, 1.1 g (3.7 mmol) of 4-(9H-carbazol-9-yl)phenylboronic acid, and 0.16 g (0.50 mmol) of tri(ortho-tolyl)phosphine, and the air in the flask was replaced with nitrogen. To this mixture were added 20 mL of toluene, 10 mL of ethanol, and 13 mL of an aqueous potassium carbonate solution (2.0 mol/L). This mixture was degassed while being stirred under reduced pressure. After the degassing, the air in the flask was replaced with nitrogen. 28 mg (0.10 mmol) of palladium(II) acetate was added to this mixture. This mixture was refluxed at 110° C. for 12 hours. After the reflux, this mixture was cooled to room temperature, and then about 20 mL of toluene was added thereto, and the mixture was filtered through Celite (a product of Wako Pure Chemical Industries, Ltd., Catalog No. 531-16855). The organic layer of the obtained mixture was washed with water and saturated saline, and dried with magnesium sulfate. This mixture was gravity filtered. The obtained filtrate was concentrated to give a brown oily substance. This oily substance was purified by silica gel column chromatography (developing solvent hexane:toluene=7:3). The obtained light-yellow solid was recrystallized from ethanol to give 1.2 g of a light-yellow powdered solid in a yield of 58%.

Then, 1.2 g of the obtained light-yellow powdered solid was sublimated and purified by train sublimation. For sublimation purification conditions, 2PCzPA was heated at 280° C. under a pressure of 8.7 Pa with argon gas at a flow rate of 3.0 mL/min. After the sublimation purification, 0.83 g of a light-yellow solid of 2PCzPA was recovered in a yield of 74%.

By nuclear magnetic resonance (NMR) measurement it was confirmed that the obtained light-yellow solid was 3-(9,10-diphenyl-2-anthryl)-9-phenyl-9H-carbazole (abbr.: 2PCzPA).

The $^1$H NMR data of 2PCzPA are shown as follows: $^1$H NMR (CDCl$_3$, 300 MHz): δ 7.30-7.34 (m, 3H), 7.41-7.49 (m, 4H), 7.53-7.65 (m, 15H), 7.70-7.74 (m, 2H), 7.79-7.84 (m, 2H), 7.98 (s, 1H), 8.15 (d, J=7.8 Hz, 1H), 8.31 (d, J=2.1 Hz, 1H).

Synthesis Example 8

Next, a synthesis method of 9-[9,10-bis(2-biphenyl)-2-anthryl]-9H-carbazole (abbr.: 2CzBPhA) which was used in Example 1 is described.

[Step 1] Synthesis of 9-[9,10-his(2-biphenyl)-2-anthryl]-9H-carbazole (abbr.: 2CzBPhA)

A synthesis scheme of 2CzBPhA is shown in the following (H-1).

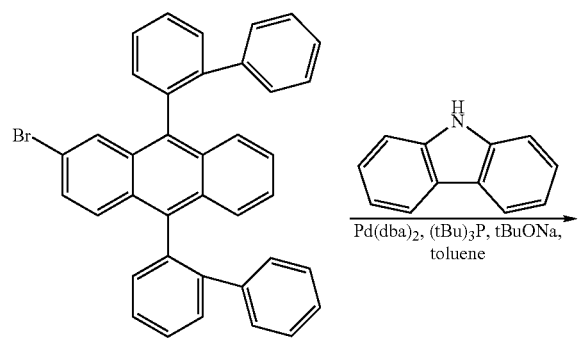

(H-1)

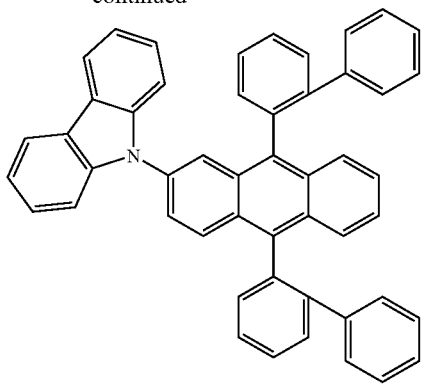

First, 2.0 g (3.5 mmol) of 2-bromo-9,10-bis(2-biphenyl) anthracene, which was synthesized in accordance with PCT International Publication No. 2007/125934, 0.60 g (3.5 mmol) of 9H-carbazole, and 2.0 g (21 mmol) of sodium tert-butoxide were put into a 100 mL three-neck flask, and the air in the flask was replaced with nitrogen. To this mixture, 30 mL of toluene and 0.1 mL of tri(tert-butyl)phosphine (10% hexane solution) were added. The mixture was stirred to be degassed while the pressure was reduced. After the degassing, 20 mg (0.035 mmol) of bis(dibenzylideneacetone)palladium (0) was added to the mixture, and then this mixture was stirred at 100° C. for 3 hours. After the stirring, the precipitated solid was collected by suction filtration. The obtained solid was dissolved in toluene and this solution was washed with water and saturated saline in this order. Then, the organic layer was dried with magnesium sulfate. The mixture was gravity filtered and the obtained filtrate was concentrated to give a solid. The solid was dissolved in toluene, and the solution was subjected to suction filtration through Florisil (product of Wako Pure Chemical Industries, Ltd., Catalog No. 540-00135), Celite (product of Wako Pure Chemical Industries, Ltd., Catalog No. 531-16855), and alumina. The obtained filtrate was then concentrated. The obtained solid was recrystallized from dichloromethane/hexane, whereby 2.0 g of a light-yellow powdered solid which was the object of the synthesis was obtained in a yield of 83%.

Then, 500 mg of 2CzBPhA was sublimated and purified by train sublimation. In the sublimation and purification, the material was heated at 350° C. under a pressure 10 of 200 Pa with argon gas flowing at a flow rate of 15.0 mL/min. After the sublimation and purification, 450 mg of 2CzBPhA was recovered in a yield of 90%.

In addition, the thermophysical property of 2CzBPhA was measured using a differential scanning calorimeter (DSC, product of PerkinElmer, Inc., Pyris 1). As a result, the crystallization temperature (Tg) proved to be 102° C.

Figure 25:
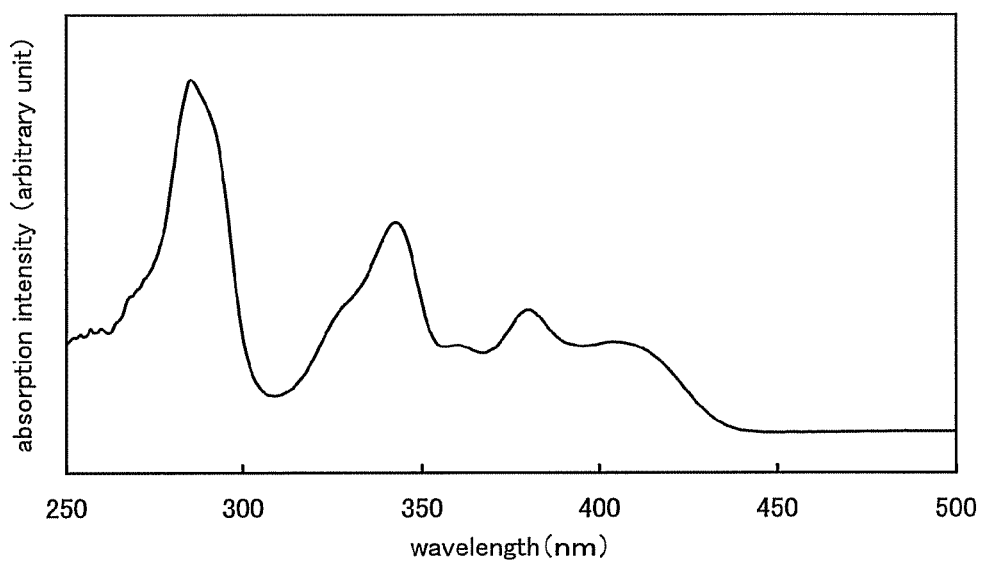
FIG. 25 is a graph showing an emission spectrum of a toluene solution of 9-[9,10-bis(2-biphenyl)-2-anthryl]-9H-carbazole (abbr.: 2CzBPhA)
Figure 26:
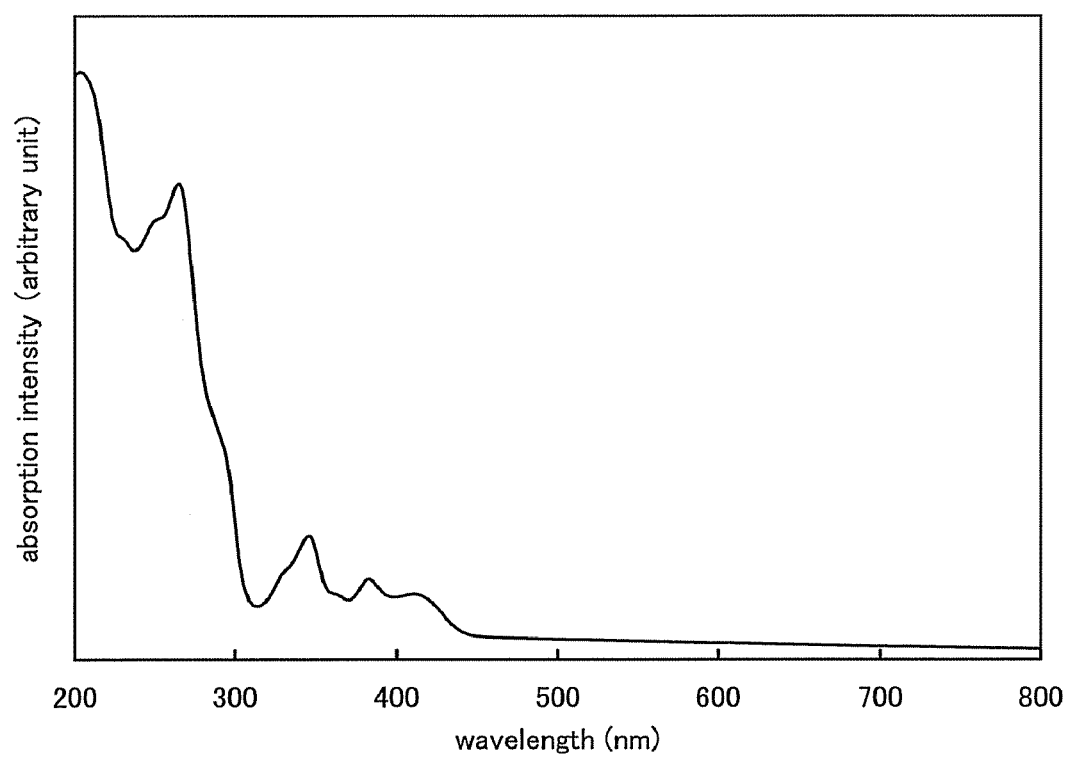
FIG. 26 is a graph showing an emission spectrum of a thin film of 9-[9,10-bis(2-biphenyl)-2-anthryl]-9H-carbazole (abbr.: 2CzBPbA)
Figure 27:
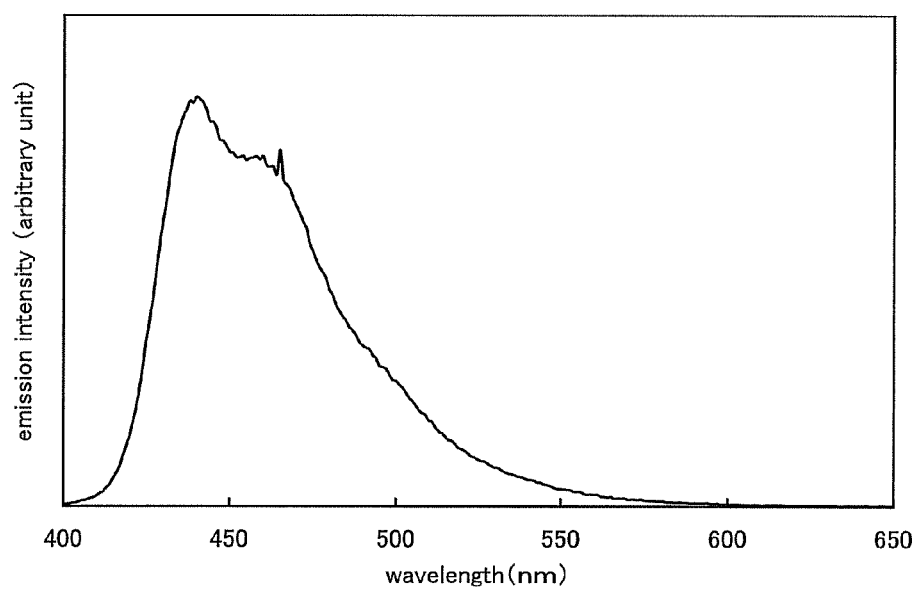
FIG. 27 is a graph showing an emission spectrum of a toluene solution of 9-[9,10-bis(2-biphenyl)-2-anthryl]-9H-carbazole (abbr.: 2CzBPhA)
Figure 28:
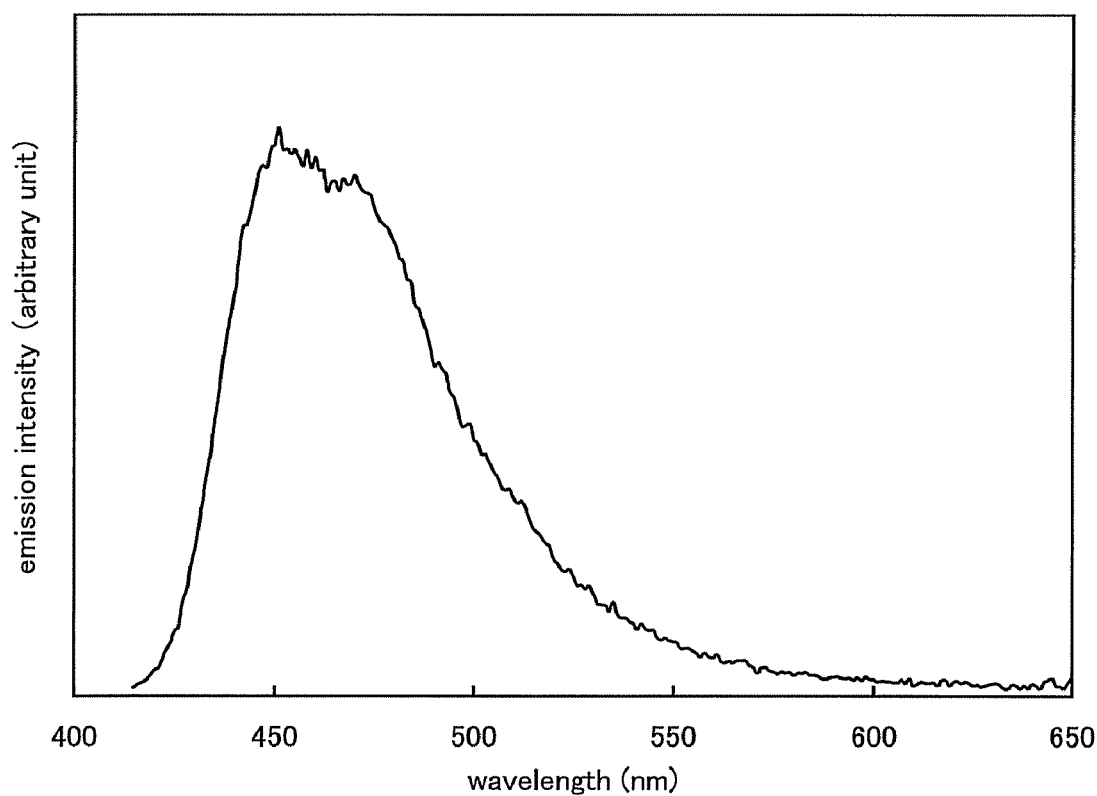
FIG. 28 is a graph showing an emission spectrum of a thin film of 9-[9,10-bis(2-biphenyl)-2-anthryl]-9H-carbazole (abbr.: 2CzBPhA)

In addition, FIG. 25 shows an absorption spectrum of a toluene solution of 2CzBPhA. FIG. 26 shows an absorption spectrum of a thin film of 2CzBPhA. An ultraviolet-visible spectrophotometer (V-550, manufactured by JASCO Corporation) was used for the measurement. The solution was put in a quartz cell. The thin film was formed by evaporation over a quartz substrate to form a sample. As for the spectrum of the solution, the absorption spectrum which was obtained by subtracting the absorption spectrum of the quartz cell including only toluene is shown in FIG. 25. As for the spectrum of the thin film, the absorption spectrum which was obtained by subtracting the absorption spectrum of the quartz substrate is shown in FIG. 26. In each of FIG. 25 and FIG. 26, the horizontal axis shows wavelength (nm), and the vertical axis shows absorption intensity (arbitrary unit). In the case of the toluene solution, the absorption was observed at around 341 nm, 379 nm, and 406 nm. In the case of the thin film, the absorption was observed at around 411 nm. Moreover, FIG. 27 shows an emission spectrum of a toluene solution of 2CzBPhA (excitation wavelength: 330 nm). FIG. 28 shows an emission spectrum of a thin film of 2CzBPhA (excitation wavelength: 411 nm). In each of FIGS. 27 and 28, a horizontal axis shows wavelength (nm) and a vertical axis shows emission intensity (an arbitrary unit). In the case of the toluene solution, the maximum emission wavelengths were 441 nm and 460 nm (excitation wavelength: 330 nm), and in the case of the thin film, the maximum emission wavelength was 451 nm n (excitation wavelength: 411 nm).

The measurement results on the thin film of 2CzBPhA using a photoelectron spectrometer (AC-2, product of Riken Keiki Co., Ltd.) in the atmosphere indicated that the HOMO level thereof was −5.57 eV. Moreover, the absorption edge was obtained from Tauc plot, with an assumption of direct transition, using data on the absorption spectrum of the thin film of 2CzBPhA in FIG. 26. Using the energy of that absorption edge as an optical energy gap, the energy gap of 2CzBPhA was found to be 2.82 eV. The LUMO level, which was estimated from the 1OMO level and the energy gap, was −2.75 eV.

Further, the oxidation-reduction reaction characteristics of 2CzBPhA were measured. The oxidation-reduction reaction characteristics were measured by cyclic voltammetry (CV). Note that an electrochemical analyzer (ALS model 600A, a product of BAS Inc.) was used for the measurement.

The solution used for the CV measurement was prepared in such a manner that a supporting electrolyte of tetra-n-butylammonium perchlorate (n-Bu$_4$NClO$_4$) (product of Tokyo Chemical Industry Co., Ltd., catalog number. T0836) was dissolved in a solvent, which is dehydrated dimethylformamide (DMF) (product of Sigma-Aldrich Corp., 99.8%, catalog number: 22705-6), at a concentration of 100 mmol/L and the measurement target was further dissolved therein at a concentration of 1 mmol/L. Further, a platinum electrode (a PTE platinum electrode, product of BAS Inc.) was used as a working electrode; a platinum electrode (a VC-3 Pt counter electrode (5 cm), product of BAS Inc.) was used as an auxiliary electrode; and an Ag/Ag$^+$ electrode (an RE5 nonaqueous solvent reference electrode, product of BAS Inc.) was used as a reference electrode. The measurement was carried out at room temperature.

The oxidation reaction characteristic of 2CzBPhA was examined by 100 cycles of measurements; one cycle is a scan in which the potential of the working electrode with respect to the reference electrode is changed from −0.03 V to 1.20 V and then changed from 1.20 V to −0.03 V. Note that the scanning speed of the CV measurement was set at 0.1 V/s.

The oxidation reaction characteristic of 2CzBPhA was examined by 100 cycles of measurements; one cycle is a scan in which the potential of the working electrode with respect to the reference electrode is changed from −0.41 V to −2.30 V and then changed from −2.30 V to −0.41 V. Note that the scanning speed of the CV measurement was set at 0.1 V/s.

Figure 29:
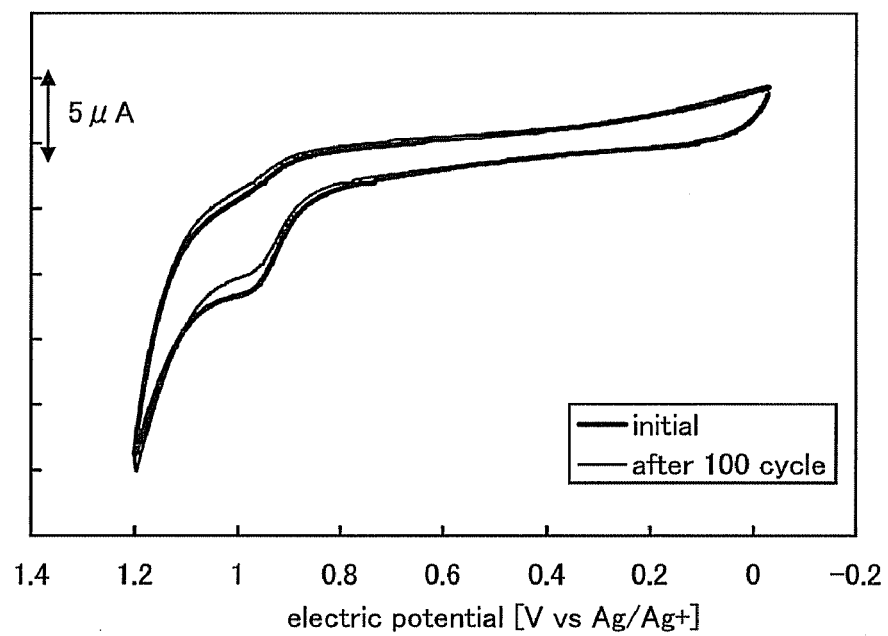
FIG. 29 is a graph showing CV measurement results of 9-[9,10-bis(2-biphenyl)-2-anthryl]-9H-carbazole (abbr.: 2CzPhA)
Figure 30:
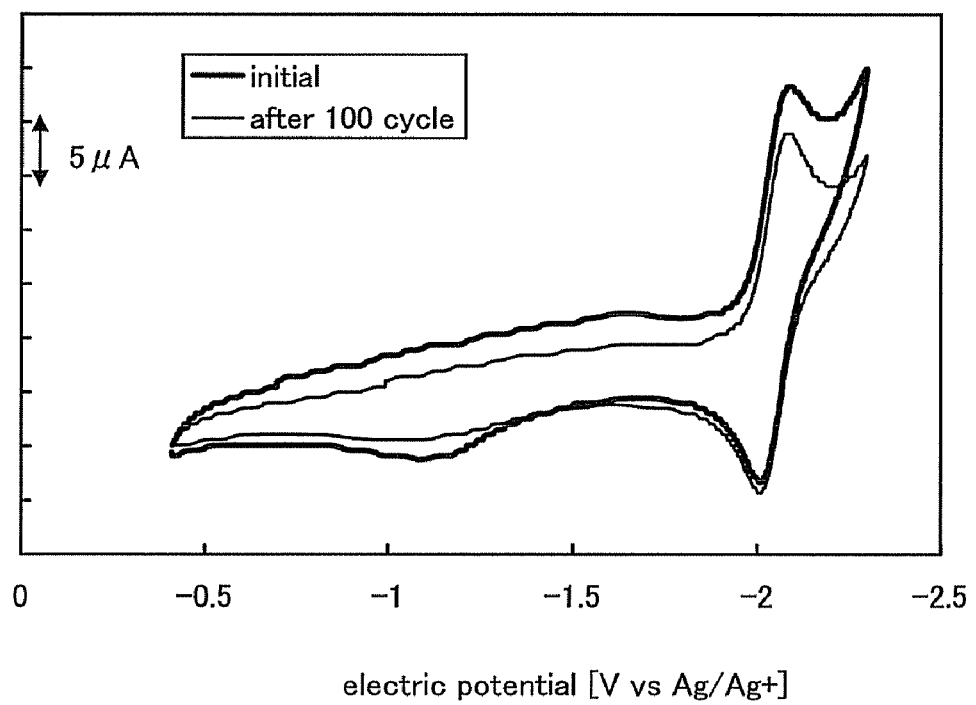
FIG. 30 is a graph showing CV measurement results of 9-[9,10-bis(2-biphenyl)-2-anthryl]-9H-carbazole (abbr.: 2CzBPhA).

FIG. 29 shows CV measurement results on the oxidation reaction characteristic of 2CzPBPhA and FIG. 30 shows CV measurement results on the reduction reaction characteristic of 2CzBPhA. In each of FIG. 29 and FIG. 30, the horizontal axis shows potential (V) of the work electrode with respect to the reference electrode, while the vertical axis shows a value (μA) of current flowing between the working electrode and the auxiliary electrode. According to FIG. 29, a current indicating oxidation was observed at around +0.96 V (vs. Ag/Ag$^+$ electrode). According to FIG. 30, a current indicating reduction was observed at around −2.08 V (vs. Ag/Ag$^+$ electrode).

This application is based on Japanese Patent Application serial no. 2008-130159 filed with Japan Patent Office on May 16, 2008, the entire contents of which are hereby incorporated by reference.

What is claimed is:

1. A composition comprising:
   an anthracene derivative which is represented by a general formula (G31-1); and
   a solvent,

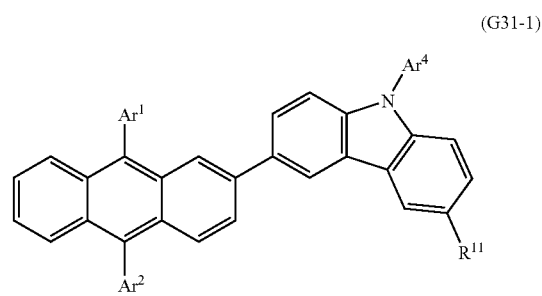

(G31-1)

wherein Ar$^1$ and Ar$^2$ each represent a substituted or unsubstituted aryl group having 6 to 13 carbon atoms, Ar$^4$ represents a substituted or unsubstituted aryl group having 6 to 13 carbon atoms, and R$^{11}$ represents hydrogen, an alkyl group having 1 to 4 carbon atoms, or a substituted or unsubstituted aryl group having 6 to 13 carbon atoms.

2. A composition comprising:
   an anthracene derivative which is represented by a general formula (G31-2); and
   a solvent,

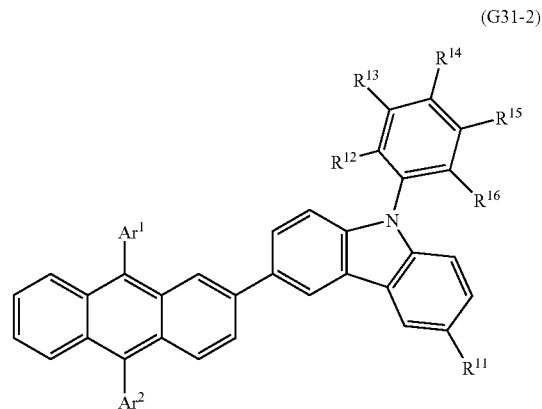

(G31-2)

wherein Ar$^1$ and Ar$^2$ each represent a substituted or unsubstituted aryl group having 6 to 13 carbon atoms, R$^{11}$ represents hydrogen, an alkyl group having 1 to 4 carbon atoms, or a substituted or unsubstituted aryl group having 6 to 13 carbon atoms, and R$^{12}$ to R$^{16}$ each represent hydrogen, an alkyl group having 1 to 4 carbon atoms, or a substituted or unsubstituted aryl group having 6 to 10 carbon atoms.

3. A composition comprising:
an anthracene derivative which is represented by a general formula (G31-3); and
a solvent,

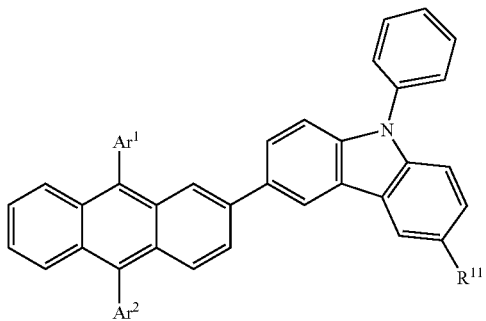

(G31-3)

wherein $Ar^1$ and $Ar^2$ each represent a substituted or unsubstituted aryl group having 6 to 13 carbon atoms, and $R^{11}$ represents hydrogen, an alkyl group having 1 to 4 carbon atoms, or a substituted or unsubstituted aryl group having 6 to 13 carbon atoms.

4. The composition according to claim 1, wherein the solvent has an aromatic ring.

5. The composition according to claim 2, wherein the solvent has an aromatic ring.

6. The composition according to claim 3, wherein the solvent has an aromatic ring.

7. A method for manufacturing a thin film, wherein the composition according to claim 1 is applied to a substrate and the solvent is removed.

8. A method for manufacturing a thin film, wherein the composition according to claim 2 is applied to a substrate and the solvent is removed.

9. A method for manufacturing a thin film, wherein the composition according to claim 3 is applied to a substrate and the solvent is removed.

10. A method for manufacturing a thin film, wherein the composition according to claim 1 is applied to a substrate and the solvent is removed by heat treatment.

11. A method for manufacturing a thin film, wherein the composition according to claim 2 is applied to a substrate and the solvent is removed by heat treatment.

12. A method for manufacturing a thin film, wherein the composition according to claim 3 is applied to a substrate and the solvent is removed by heat treatment.

13. A method for manufacturing a light-emitting element comprising the steps of:
forming a first electrode;
forming a layer containing a light-emitting substance by application of the composition according to any one of claims 1 to 3 to the first electrode and then removal of the solvent; and
forming a second electrode over the layer containing a light-emitting substance.

14. The method for manufacturing a light-emitting element according to claim 13, wherein a functional layer is formed by a coating method on at least one side of the first electrode side and the second electrode side of the layer containing a light-emitting substance.

15. The method for manufacturing a light-emitting element according to claim 13, wherein a functional layer is formed by an evaporation method on at least one side of the first electrode side and the second electrode side of the layer containing a light-emitting substance.

* * * * *

UNITED STATES PATENT AND TRADEMARK OFFICE
CERTIFICATE OF CORRECTION

PATENT NO. : 8,231,942 B2
APPLICATION NO. : 12/466910
DATED : July 31, 2012
INVENTOR(S) : Satoko Shitagaki et al.

It is certified that error appears in the above-identified patent and that said Letters Patent is hereby corrected as shown below:

Column 120, Line 4; Change "PNCZPA" to --bNCzPA--.

Column 127, Line 3; Change "A to B" to --A to E--.

Column 127, Line 29; Change "light-emitting element B" to --light-emitting element E--.

Column 127, Line 48; Change "light-emitting element B" to --light-emitting element E--.

Column 129, Line 48; Change "abbn: PCCPA)" to --(abbr: PCCPA)--.

Column 130, Line 43; Change "152 ing" to --152 mg--.

Column 130, Line 50; Change "palladium(11)" to --palladium(II)--.

Column 140, Line 65; Change "(1.0 molL)" to --(1.0 mol/L)--.

Column 142, Line 49; Change "(10 μmol)" to --(10 mmol)--.

Column 142, Line 50; Change "(20 μmol)" to --(20 mmol)--.

Column 146, Lines 12-13; Change "9-[3-(10-phenyl-9-antbryl)phenyl]-9H-carbazole" to
--9-[3-(10-phenyl-9-anthryl)phenyl]-9H-carbazole--.

Column 148, Line 51; Change "(CCl$_3$, 300MHz)" to --(CDCl$_3$, 300MHz)--.

Column 151, Lines 45-46; Change "9-[9,10-his(2-biphenyl)-2-anthryl]-9H-carabazole" to
--9-[9,10-bis(2-biphenyl)-2-anthryl]-9H-carabazole--.

Signed and Sealed this
Sixteenth Day of October, 2012

David J. Kappos
*Director of the United States Patent and Trademark Office*

CERTIFICATE OF CORRECTION (continued)
U.S. Pat. No. 8,231,942 B2

Column 153, Line 24; Change "10MO" to --HOMO--.

Column 153, Line 60; Change "2CzPBPhA" to --2CzBPhA--.